(12) United States Patent
Johnson et al.

(10) Patent No.: US 10,973,847 B2
(45) Date of Patent: Apr. 13, 2021

(54) CORE-TO-SURFACE POLYMERIZATION FOR THE SYNTHESIS OF STAR POLYMERS AND USES THEREOF

(71) Applicant: Massachusetts Institute of Technology, Cambridge, MA (US)

(72) Inventors: Jeremiah A. Johnson, Boston, MA (US); Matthew R. Golder, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/024,665

(22) Filed: Jun. 29, 2018

(65) Prior Publication Data

US 2019/0030067 A1  Jan. 31, 2019

Related U.S. Application Data

(60) Provisional application No. 62/528,013, filed on Jun. 30, 2017.

(51) Int. Cl.
*A61K 31/787* (2006.01)
*C08F 291/06* (2006.01)
(Continued)

(52) U.S. Cl.
CPC .......... *A61K 31/787* (2013.01); *C08F 291/06* (2013.01); *C08G 61/08* (2013.01); *C08G 77/442* (2013.01); *C08G 83/002* (2013.01); *C08F 232/08* (2013.01); *C08G 2261/135* (2013.01); *C08G 2261/148* (2013.01); *C08G 2261/1426* (2013.01); *C08G 2261/1432* (2013.01); *C08G 2261/3225* (2013.01); *C08G 2261/354* (2013.01); *C08G 2261/418* (2013.01); *C08G 2261/522* (2013.01); *C08G 2261/76* (2013.01);
(Continued)

(58) Field of Classification Search
None
See application file for complete search history.

(56) References Cited

U.S. PATENT DOCUMENTS 4,359,425 A  11/1982  Totani et al.
5,811,515 A  9/1998  Grubbs et al.
(Continued)

FOREIGN PATENT DOCUMENTS

CN  101412792 A  4/2009
KR  20120113694 A  10/2012
(Continued)

OTHER PUBLICATIONS

International Search Report and Written Opinion for PCT/US2017/055145, dated Jan. 23, 2018.
(Continued)

*Primary Examiner* — Aradhana Sasan
*Assistant Examiner* — Quanglong N Truong
(74) *Attorney, Agent, or Firm* — Wolf, Greenfield & Sacks, P.C.

(57) ABSTRACT

Disclosed are methods, compositions, reagents, systems, and kits to prepare star polymers, as well as compositions and uses thereof. Various embodiments show that synthesis of these polymers contain low metal concentration to provide polymers for diverse biomedical applications including in vivo applications.

27 Claims, 25 Drawing Sheets

(51) Int. Cl.
    *C08G 77/442*       (2006.01)
    *C08G 61/08*        (2006.01)
    *C08G 83/00*        (2006.01)
    *C08F 232/08*      (2006.01)

(52) U.S. Cl.
    CPC ...... *C08G 2261/94* (2013.01); *C08L 2310/00* (2013.01)

(56) References Cited

U.S. PATENT DOCUMENTS

| | | |
|---|---|---|
| 8,067,505 B2 | 11/2011 | Harris et al. |
| 9,381,253 B2 | 7/2016 | Johnson et al. |
| 9,447,129 B2 | 9/2016 | Johnson et al. |
| 9,822,216 B2 | 11/2017 | Mahanthappa et al. |
| 10,023,536 B2 | 7/2018 | Johnson et al. |
| 10,105,449 B2 | 10/2018 | Johnson et al. |
| 10,153,513 B2 | 12/2018 | Grubbs et al. |
| 10,159,749 B2 | 12/2018 | Johnson et al. |
| 2002/0183473 A1 | 12/2002 | Matyjaszewski et al. |
| 2002/0198328 A1 | 12/2002 | L'Alloret |
| 2003/0065023 A1 | 4/2003 | Swindell et al. |
| 2005/0109976 A1 | 5/2005 | Fuchs et al. |
| 2011/0243848 A1* | 10/2011 | Appel ............... A61K 49/0036 424/9.1 |
| 2011/0300219 A1 | 12/2011 | Lippard et al. |
| 2013/0296491 A1 | 11/2013 | Xia et al. |
| 2013/0324666 A1 | 12/2013 | Yan et al. |
| 2014/0142249 A1 | 5/2014 | Cho et al. |
| 2014/0308234 A1 | 10/2014 | Johnson et al. |
| 2015/0225438 A1 | 8/2015 | Johnson et al. |
| 2016/0024246 A1 | 1/2016 | Mahanthappa et al. |
| 2016/0289392 A1 | 10/2016 | Grubbs et al. |
| 2016/0296631 A1 | 10/2016 | Johnson et al. |
| 2016/0361702 A1 | 12/2016 | Cohen et al. |
| 2017/0000909 A1 | 1/2017 | Gianneschi et al. |
| 2017/0073311 A1 | 3/2017 | Johnson et al. |
| 2017/0348431 A1 | 12/2017 | Johnson et al. |
| 2018/0030213 A1 | 2/2018 | Johnson et al. |
| 2018/0036415 A9 | 2/2018 | Johnson et al. |
| 2018/0094099 A1 | 4/2018 | Johnson et al. |
| 2019/0030067 A1 | 1/2019 | Johnson et al. |
| 2019/0038751 A1 | 2/2019 | Johnson et al. |
| 2019/0038782 A1 | 2/2019 | Johnson et al. |
| 2019/0054187 A1 | 2/2019 | Johnson et al. |
| 2019/0192672 A1 | 6/2019 | Appel et al. |

FOREIGN PATENT DOCUMENTS

| | | |
|---|---|---|
| WO | WO 2010/047765 A2 | 4/2010 |
| WO | WO 2013/169739 A1 | 11/2013 |
| WO | WO 2014/169073 A1 | 10/2014 |
| WO | WO 2016/023036 A1 | 2/2016 |

OTHER PUBLICATIONS

International Search Report for PCT/US2017/48641, dated Nov. 9, 2017.
International Preliminary Report on Patentability for Application No. PCT/US2017/48641 dated Mar. 7, 2019.
International Search Report and Written Opinion for Application No. PCT/US2018/040496 dated Jan. 14, 2019.
International Preliminary Report on Patentability for PCT/US2017/055145, dated Apr. 18, 2019.
International Preliminary Report on Patentability for PCT/US2017/064784, dated Jun. 20, 2019.
Bates et al., Polarity-switching top coats enable orientation of sub-10-nm block copolymer domains Science. Nov. 9, 2012;338(6108):775-9. doi: 10.1126/science.1226046.
Bohbot-Raviv et al., Discovering new ordered phases of block copolymers Phys Rev Lett. Oct. 16, 2000;85(16):3428.
Cheng et al., Well-defined diblock macromonomer with a norbornene group at block junction: anionic living linking synthesis and ring-opening metathesis polymerization. Macromol. Mar. 4, 2010;43(7):3153-5.
Dalsin et al., Bottlebrush block polymers: Quantitative theory and experiments. ACS Nano. Nov. 6, 2015;9(12):12233-45.
Davis et al., Atom transfer radical polymerization of tert-butyl acrylate and preparation of block copolymers. Macromol. May 30, 2000;33(11):4039-47.
Frechet. Functional polymers and dendrimers: reactivity, molecular architecture, and interfacial energy. Science. Mar. 25, 1994;263(5154):1710-5.
Godugu et al., Abstract 2139: Effect of telmisartan on triple negative breast cancer (TNBC) and lung cancer tumor progression and intratumoral distribution of nanoparticles. Cancer Res. 2013;73(8). 4 pages.
Grahovac et al. Abstract B41: The angiotensin receptor blocker telmisartan inhibits the growth of pancreatic ductal adenocarcinoma and improves survival. Cancer Res. 2016;76(24). 4 pages.
Grason et al., Geometric theory of diblock copolymer phases. Phys Rev Lett. Jul. 31, 2003;91(5):058304.
Hawker et al., Preparation of polymers with controlled molecular architecture. A new convergent approach to dendritic macromolecules. J Am Chem Soc. Oct. 1990;112(21):7638-47.
Heroguez et al., Novel Styrene—Butadiene Copolymers by Ring-Opening Metathesis Polymerization. Macromol. Oct. 3, 2000;33(20):7241-8.
Jakubowski et al., Activators regenerated by electron transfer for atom transfer radical polymerization of styrene. Macromol. Jan. 10, 2006;39(1):39-45.
Jeong et al., Highly tunable self-assembled nanostructures from a poly (2-vinylpyridine-b-dimethylsiloxane) block copolymer. Nano Lett. Sep. 27, 2011;11(10):4095-101.
Jiang et al., Morphology and Phase Diagram of Comb Block Copolymer A m+ 1 (BC) m. J Phys Chem B. May. 7, 2009;113(21):7462-7.
Jung et al., Orientation-controlled self-assembled nanolithography using a polystyrene—polydimethylsiloxane block copolymer. Nano Lett. Jul. 11, 2007;7(7):2046-50.
Kale et al., Supramolecular assemblies of amphiphilic homopolymers. Langmuir. May 19, 2009;25(17):9660-70.
Kawamoto et al., Loops versus branch functionality in model click hydrogels. Macromol. Dec. 1, 2015;48(24):8980-8.
Lee et al., Novel phase morphologies in a microphase-separated dendritic polymer melt. Macromol. Jan. 12, 2009;42(3):849-59.
Li et al., Crosslinking-induced morphology change of latex nanoparticles: A study of RAFT—mediated polymerization in aqueous dispersed media using amphiphilic double-brush copolymers as reactive surfactants. J Polym Sci Part A: Polym Chem. Nov. 15, 2014;52(22):3250-9.
Li et al., Dynamic cylindrical assembly of triblock copolymers by a hierarchical process of covalent and supramolecular interactions. J Am Chem Soc. Jan. 4, 2011;133(5):1228-31.
Li et al., Efficient synthesis of narrowly dispersed amphiphilic double-brush copolymers through the polymerization reaction of macromonomer micelle emulsifiers at the oil—water interface. Polym Chem. 2016;7(27):4476-85.
Li et al., Facile syntheses of cylindrical molecular brushes by a sequential RAFT and ROMP "grafting-through" methodology. J Polym Sci A Polym Chem. Oct. 15, 2009;47(20):5557-5563.
Li et al., Synthesis of Hetero-Grafted Amphiphilic Diblock Molecular Brushes and Their Self-Assembly in Aqueous Medium. Macromolecules. 2010;43(3):1182-1184.
Li et al., Well-defined amphiphilic double-brush copolymers and their performance as emulsion surfactants. Macromol. May 18, 2012;45(11):4623-9.
Luo et al., Toroidal structures from brush amphiphiles. Chem Commun. 2014;50(5):536-8.
Rangadurai et al., Temporal and triggered evolution of host—guest characteristics in amphiphilic polymer assemblies. J Am Chem Soc. Jun. 10, 2016;138(24):7508-11.
Rasmussen et al., Improved numerical algorithm for exploring block copolymer mesophases. J Polym Sci Part B: Poly Phys. Aug. 15, 2002;40(16):1777-83.

(56) References Cited

OTHER PUBLICATIONS

Rzayev Synthesis of polystyrene—polylactide bottlebrush block copolymers and their melt self-assembly into large domain nanostructures. Macromol. Feb. 20, 2009;42(6):2135-41.
Sides et al., Parallel algorithm for numerical self-consistent field theory simulations of block copolymer structure. Polymer. Sep. 1, 2003;44(19):5859-66.
Sinturel et al., High χ—low N block polymers: how far can we go?. ACS Macro Lett. Sep. 2, 2015;4:1044-50.
Sowers et al., Redox-responsive branched-bottlebrush polymers for in vivo MRI and fluorescence imaging. Nat Commun. Nov. 18, 2014;5:5460.
Theodorakis et al., Interplay between chain collapse and microphase separation in bottle-brush polymers with two types of side chains Macromol. May 4, 2010;43(11):5137-48.
Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.
Yuan et al., One-pot syntheses of amphiphilic centipede-like brush copolymers via combination of ring-opening polymerization and "click" chemistry. Macromol. Jan. 27, 2010;43(4):1739-46.
Zhao et al., Polystyrene—Polylactide Bottlebrush Block Copolymer at the Air/Water Interface. Macromol. Sep. 28, 2009;42(22):9027-33.
Zheng et al., Morphology of ABC triblock copolymers. Macromol. Oct. 1995;28(21):7215-23.
Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.
International Search Report and Written Opinion dated Aug. 29, 2014 for Application No. PCT/US2014/33554.
Anderson, Late Transition Metal Complexes of Pentafluorophenylphosphino-Pincer Ligands. Doctoral Thesis. Victoria University of Wellington. 2012:ii, iii, 32.
Huynh, Novel Polymeric Micelles via RAFT Polymerization for Platinum Drug Delivery. Doctoral Thesis. The University of New South Wales. 2012:i, 57-58.
Johnson et al., Core-clickable PEG-branch-azide bivalent-bottlebrush polymers by ROMP: grafting-through and clicking-to. J Am Chem Soc. Jan. 26, 2011;133(3):559-66. doi: 10.1021/ja108441d. Epub Dec. 13, 2010.
Johnson et al., Drug-loaded, bivalent-bottle-brush polymers by graft-through ROMP. Macromolecules. Dec. 28, 2010;43(24):10326-10335.
Johnson et al., Efficient Synthesis of Doxorubicin Releasing Brush Polymers by Graft-Through Romp. Polymer Preprints. 2010;51(2):96-97.
Li et al., Surface Properties of Bottlebrush Polymer Thin Films. Macromolecules. 2012;45(17):7118-7127.
Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.
International Preliminary Report on Patentability for PCT/US2014/033554, dated Oct. 22, 2015.
Extended European Search Report for EP 14782253.0, dated Nov. 11, 2016.
International Search Report and Written Opinion for PCT/US2017/036447, dated Sep. 7, 2017.
International Preliminary Report on Patentability for PCT/US2017/036447, dated Dec. 20, 2018.
International Search Report and Written Opinion for PCT/US2017/064784, dated Mar. 1, 2018.
International Search Report and Written Opinion for PCT/US2018/040488, dated Oct. 15, 2018.
International Search Report and Written Opinion for PCT/US2018/040494, dated Oct. 10, 2018.
Invitation to Pay Additional Fees for PCT/US2018/040496, dated Nov. 21, 2018.

Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels—Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. EpubSep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Bunco et al., Profluorescent Nitroxides as Sensitive Probes of Oxidative Change and Free Radical Reactions. Australian Journal of Chemistry 2010;64(4):373-389. https://doi.org/10.1071/CH10442.

(56) References Cited

OTHER PUBLICATIONS

Boase et al., Molecular imaging with polymers. Polym. Chem., 2012,3, 1384-1389. DOI: 10.1039/C2PY20132A.

Bobko et al., Reversible reduction of nitroxides to hydroxylamines: roles for ascorbate and glutathione. Free Radic Biol Med. Feb. 1, 2007;42(3):404-12. Epub Nov. 10, 2006.

Brasch et al., Work in progress: nuclear magnetic resonance study of a paramagnetic nitroxide contrast agent for enhancement of renal structures in experimental animals. Radiology. Jun. 1983;147(3):773-9.

Brasch, Work in progress: methods of contrast enhancement for NMR imaging and potential applications. A subject review. Radiology. Jun. 1983;147(3):781-8.

Brummelhuis et al., Stimuli-responsive star polymers through thiol—yne core functionalization/crosslinking of block copolymer micelles. Polym. Chem., 2011;2:1180-1184. DOI: 10.1039/C1PY00002K.

Budil et al., Nonlinear-Least -Squares Analysis of Slow-Motion EPR Spectra in One and Two Dimensions Using a Modified Levenberg—Marquardt Algorithm. Elsevier. Journal of Magnetic Resonance, Series A. Jun. 1996;120(2):155-189.

Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.

Bunzen et al., Self-assembly of M24L48 polyhedra based on empirical prediction. Angew Chem Int Ed Engl. Mar. 26, 2012;51(13):3161-3. doi: 10.1002/anie.201108731.

Burdynska et al., Synthesis of Star Polymers Using ARGET ATRP. Macromolecules, 2010;43(22):9227-9229. DOI: 10.1021/ma101971z.

Burnworth et al., Decoupling Optical Properties in Metallo-Supramolecular Poly (p-phenylene ethynylene)s. Macromolecules. 2008;41(6):2157-2163.

Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.

Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.

Burts et al., Using EPR to Compare PEG-branch-nitroxide "Bivalent-Brush Polymers" and Traditional PEG Bottle—Brush Polymers: Branching Makes a Difference. Macromolecules. 2012;45(20):8310-18.

Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.

Caiolfa et al., Polymer-bound camptothecin: initial biodistribution and antitumour activity studies. J Control Release. Mar. 1, 2000;65(1-2):105-19.

Campos-Fernandez et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernandez et al., Fine-tuning the ring-size of metallacyclophanes: a rational approach to molecular pentagons. J Am Chem Soc. Jan. 31, 2001;123(4):773-4.

Caravan et al., Gadolinium(III) Chelates as MRI Contrast Agents: Structure, Dynamics, and Applications. Chem Rev. Sep. 8, 1999;99(9):2293-352.

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheon et al., Synergistically integrated nanoparticles as multimodal probes for nanobiotechnology.Acc Chem Res. Dec. 2008;41(12):1630-40. doi: 10.1021/ar800045c.

Chifotides et al., Anion-.pi. interactions in supramolecular architectures. Acc Chem Res. Apr. 16, 2013;46(4):894-906. doi: 10.1021/ar300251k. Epub Mar. 11, 2013.

Choi et al., Self-confirming "AND" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Dag et al., Three-arm star ring opening metathesis polymers via alkyne-azide click reaction. J. Polym. Sci. A Polym. Chem., 47: 2344-2351. doi:10.1002/pola.23324.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.

Detape et al., Advanced multimodal nanoparticles delay tumor progression with clinical radiation therapy. J Control Release. Sep. 28, 2016;28;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan et al., The dawning era of polymer therapeutics. Nat Rev Drug Discov. May 2003;2(5):347-60.

Duncan, The dawning era of polymer therapeutics. Nat Rev Drug Discov. May 2003;2(5):347-60.

(56) References Cited

OTHER PUBLICATIONS

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular knots, links, and entanglements. Chem Rev. Sep. 14, 2014;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Fullenkamp et al., Mussel-Inspired Histidine-Based Transient Network Metal Coordination Hydrogels. Macromolecules. Jan. 18, 2013;46(3):1167-1174.

Gao et al., Development of star polymers as unimolecular containers for nanomaterials. Macromol Rapid Commun. May 14, 2012;33(9):722-34. doi: 10.1002/marc.201200005. Epub Mar. 14, 2012.

Gao et al., Modular Approaches to Star and Miktoarm Star Polymers by ATRP of Cross-Linkers. Macromol. Symp., 291-292: 12-16. doi:10.1002/masy.201050502.

Gao et al., Synthesis of Acid-Labile PEG and PEG-Doxorubicin-Conjugate Nanoparticles via Brush-First ROMP. ACS Macro Lett., 2014;3(9):854-857. DOI: 10.1021/mz5004097.

Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125. DOI: 10.1021/ma702560f.

Ge et al., A Pyrene-functionalized Polynorbornene for Ratiometric Fluorescence Sensing of Pyrophosphate. Chem. Asian J. 2016;11:687.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Glunde et al., Magnetic resonance spectroscopy in metabolic and molecular imaging and diagnosis of cancer. Chem Rev. May 12, 2010;110(5):3043-59. doi: 10.1021/cr9004007.

Goh et al., Highly efficient synthesis of low polydispersity core cross-linked star polymers by Ru-catalyzed living radical polymerization. Macromol Rapid Commun. Mar. 2, 2011;32(5)456-61. doi: 10.1002/marc.201000641. Epub Jan. 7, 2011.

Greenwald et al., Effective drug delivery by PEGylated drug conjugates. Adv Drug Deliv Rev. Feb. 10, 2003;55(2):217-50.

Grumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Haddleton et al., Well-defined oligosaccharide-terminated polymers from living radical polymerization. Biomacromolecules. 2000 Summer;1(2):152-6.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition—fragmentation chain transfer agents: Syntheses and polymerization. J. Polym. Sci. A Polym. Chem., 2004;42:5877-5890. doi:10.1002/pola.20434.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi:10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)—Dithiolane Gold Nanoparticles for T1-Weighted Magnetic Resonance Imaging of the Pancreas. Nano Lett. May 11 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

(56) References Cited

OTHER PUBLICATIONS

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.
Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.
Huinink et al., Topotecan versus paclitaxel for the treatment of recurrent epithelial ovarian cancer. J Clin Oncol. Jun. 1997;15(6):2183-93.
Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.
Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.
Hyodo et al., Probing the intracellular redox status of tumors with magnetic resonance imaging and redox-sensitive contrast agents. Cancer Res. Oct. 15, 2006;66(20):9921-8.
Iha et al., Applications of Orthogonal "Click" Chemistries in the Synthesis of Functional Soft Materials. Chem. Rev., 2009;109(11):5620-5686. DOI: 10.1021/cr900138t.
Inglis et al., Well-defined star shaped polymer-fullerene hybrids via click chemistry. Soft Matter, 2010;6:82-84. DOI: 10.1039/B920806M.
Jackson et al., pH triggered self-assembly of core cross-linked star polymers possessing thermoresponsive cores. Chem. Commun., 2011;47:6807-6809. DOI: 10.1039/C1CC11785H.
Jamieson et al., Structure, Recognition, and Processing of Cisplatin-DNA Adducts. Chem Rev. Sep. 8, 1999;99(9):2467-98.
Jesberger et al., Hyperbranched polymers as scaffolds for multifunctional reversible addition—fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.
Jokerst et al., Molecular imaging with theranostic nanoparticles. Acc Chem Res. Oct. 18, 2011;44(10):1050-60. doi: 10.1021/ar200106e. Epub Sep. 15, 2011.
Jokerst et al., Nanoparticle PEGylation for imaging and therapy. Nanomedicine (Lond). Jun. 2011;6(4):715-28. doi: 10.2217/nnm.11.19.
Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.
Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.
Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.
Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.
Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.
Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.
Kim et al., Anion-directed self-assembly of coordination polymer into tunable secondary structure. J Am Chem Soc. Jun. 9, 2004;126(22):7009-14.
Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi200-40219_113203.pdf Retrieved Apr. 24, 2015.
Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20,2002;124(46):13662-3.
Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.
Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.
Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.
Kreutzer et al., Water-Soluble, Unimolecular Containers Based on Amphiphilic Multiarm Star Block Copolymers. Macromolecules, 2006;39(13):4507-4516. DOI: 10.1021/ma060548b.
Kwon et al., Block copolymer micelles as long-circulating drug vehicles. Adv Drug Delivery Rev. 1995;16:295-309.
Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.
Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.
Lee et al., Mussel-Inspired Adhesives and Coatings. Annu Rev Mater Res. Aug. 1, 2011;41:99-132.
Lee et al., Single-molecule mechanics of mussel adhesion. Proc Natl Acad Sci U S A. Aug. 29, 2006;103(35):12999-3003. Epub Aug. 18, 2006.
Lee et al., Stimuli-responsive molecular brushes. Progress in Polymer Science (Oxford), 35(1-2), 24-44. DOI: 10.1016/j.progpolymsci.2009.11.002.
Leininger et al., Self-assembly of discrete cyclic nanostructures mediated by transition metals. Chem Rev. Mar. 8, 2000;100(3):853-908.
Li et al., A magnetic switch for spin-catalyzed interconversion of nuclear spin isomers. J Am Chem Soc. Mar. 31, 2010;132(12):4042-3. doi: 10.1021/ja910282p.
Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.
Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.
Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.
Li et al., Pinpointing the extent of electronic delocalization in the Re(I)-to-tetrazine charge—separated excited state using time-resolved infrared spectroscopy. J Am Chem Soc. Aug. 26, 2009;131(33):11656-7. doi: 10.1021/ja903901n.
Li et al., Polycatechol Nanoparticle MRI Contrast Agents. Small, 2016;12(5):668-677. https://doi.org/10.1002/smll.201502754.
Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.
Liang et al., the copper(I)-catalyzed alkyne-azide cycloaddition (CuAAC) "click" reaction and its applications. An overview. Coordination Chemistry Reviews Dec. 2011;255(23-24):2933-2945.
Liao et al., A Convergent Synthetic Platform for Single-Nanoparticle Combination Cancer Therapy: Ratiometric Loading

(56) References Cited

OTHER PUBLICATIONS and Controlled Release of Cisplatin, Doxorubicin, and Camptothecin. J. Am. Chem. Soc., 2014;136(16):5896-5899. DOI: 10.1021/ja502011g.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805. doi: 10.1021/acsnano.6b07196.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., a new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., Oximes as reversible links in polymer chemistry: dynamic macromolecular stars. Polym. Chem., 2014;5:6923-6931. DOI: 10.1039/C4PY01282H.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nair et al., Modulating mechanical properties of self-assembled polymer networks by mult-ifunctional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

(56) References Cited

OTHER PUBLICATIONS

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al., Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architecures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Rzayev et al., Molecular Bottlebrushes: New Opportunities in Nanomaterials Fabrication. ACS Macro Lett., 2012;1(9):1146-1149. DOI: 10.1021/m7300402x.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host—guest self—assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications2014;5:Article No. 5460.

(56) References Cited

OTHER PUBLICATIONS

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Thompson et al., Labelling polymers and micellar nanoparticles via initiation, propagation and termination with ROMP. Polym. Chem., 2014;5:1954-1964.

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

Tolmasoff et al., Superoxide dismutase: correlation with life-span and specific metabolic rate in primate species. Proc Natl Acad Sci U S A. May 1980;77(5):2777-81.

Tominaga et al., Finite, spherical coordination networks that self-organize from 36 small components. Angew Chem Int Ed Engl. Oct. 25, 2004;43(42):5621-5.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.

Valeur et al., Amide bond formation: beyond the myth of coupling reagents. Chem. Soc. Rev., 2009;38:606-631. DOI: 10.1039/B701677H.

Verduzco et al., Correction: Structure, function, self-assembly, and applications of bottlebrush copolymers. Chem Soc Rev. Nov. 7, 2015;44(21):7916. doi: 10.1039/c5cs90099a.

Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.

Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.

Wang et al., Advances of cancer therapy by nanotechnology. Cancer Res Treat. Mar. 2009;41(1):1-11. doi: 10.4143/crt.2009.41.1.1. Epub Mar. 31, 2009.

Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/o1502449r].

Wei et al., Exceedingly small iron oxide nanoparticles as positive MRI contrast agents. Proc. Natl. Acad. Sci. USA 2017;114(9):2325-2330.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Wong et al., Quantitative formation of core cross-linked star polymers via a one-pot two-step single electron transfer-living radical polymerization. Polym. Chem., 2013;4:4562-4565. DOI: 10.1039/C3PY00726J.

Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.

Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.

Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Xiao et al., the use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. EpubAug. 28, 2012.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

(56) References Cited

OTHER PUBLICATIONS

Xu et al., Scaling Laws in Supramolecular Polymer Networks. Macromolecules. 2011;44(13):5465-5472.

Xu et al., Strain Hardening and Strain Softening of Reversibly Cross-linked Supramoleecular Polymer Networks. Macromolecules. Sep. 27, 2011;44(18):7478-7488.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.

Yan et al., Particle carriers for combating multidrug-resistant cancer. ACS Nano. Nov. 26, 2013;7(11):9512-7. doi: 10.1021/nn405632s. Epub Nov. 11, 2013.

Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.

Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.

Yang et al., Luminescent chemodosimeters for bioimaging. Chem Rev. Jan. 9, 2013;113(1):192-270. doi: 10.1021/cr2004103. Epub Jun. 18, 2012.

Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.

Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.

Yoshizawa et al., Molecular architectures of multi-anthracene assemblies. Chem Soc Rev. Mar. 21, 2014;43(6):1885-98. doi: 10.1039/c3cs60315f.

You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.

Yount et al., Small-molecule dynamics and mechanisms underlying the macroscopic mechanical properties of coordinatively cross-linked polymer networks. J Am Chem Soc. Oct. 19, 2005;127(41):14488-96.

Yount et al., Strong means slow: dynamic contributions to the bulk mechanical properties of supramolecular networks. Angew Chem Int Ed Engl. Apr. 29, 2005;44(18):2746-8.

Yue et al., Macrocyclic and lantern complexes of palladium(II) with bis(amidopyridine) ligands: synthesis, structure, and host-guest chemistry. Inorg Chem. Nov. 29, 2004;43(24):7671-81.

Zhang et al., Active cross-linkers that lead to active gels. Angew Chem Int Ed Engl. Oct. 25, 2013;52(44):11494-8. doi: 10.1002/anie.201304437. Epub Sep. 12, 2013.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. 2012 Feb 20;51(4):2325-31. doi: 10.1021/ic202322f. Epub Feb. 8, 2012.

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., polyMOFs: A Class of Interconvertible Polymer-Metal-Organic-Framework Hybrid Engl. May 18, 2015;54(21):6152-7. doi: Apr. 29, 2015. Materials. Angew Chem Int Ed 10.1002/anie.201502733. Epub.

Zhang et al., Redox-Responsive, Core Cross-Linked Polyester Micelles. ACS Macro Lett., 2013;2(1):40-44. DOI: 10.1021/mz300522n.

Zhao et al., Rheological Behavoir of Shear-Responsive Metallo-Supramolecular Gels. Macromolecules. 2004;37(10):3529-3531.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.

Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.

Zhou et al., Counting primary loops in polymer gels. Proc Natl Acad Sci U S A. Nov. 20, 2012;109(47):19119-24. doi: 10.1073/pnas.1213169109. Epub Nov. 6, 2012.

Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.

International Preliminary Report on Patentability for PCT/US2018/040488, dated Jan. 9, 2020.

International Preliminary Report on Patentability for PCT/US2018/040494, dated Jan. 9, 2020.

International Preliminary Report on Patentability for PCT/US2018/040496, dated Jan. 9, 2020.

Bolton et al., Synthesis and Melt Self-Assembly of PS—PMMA—PLA Triblock Bottlebrush Copolymers. Macromolecules, 2014;47(9):2864-74. DOI: 10.1021/ma500625k.

Fenlon et al., The Thread & Cut Method: Syntheses of Molecular Knot Precursors. Eur J Org Chem. Jun. 2008;2008(18):3065-3068.

Gestwicki et al., Influencing receptor-ligand binding mechanisms with multivalent ligand architecture. J Am Chem Soc. Dec. 18, 2002;124(50):14922-33.

Hoogenboom et al., 1-Lactide Polymerization Utilizing a Hydroxy-Functionalized 3,6-Bis(2-pyridyl)pyridazine as Supramolecular (Co)initiator: Construction of Polymeric [2 ×2] Grids. Macromolecules, 2003;36(13):4743-9. DOI: 10.1021/ma034119e.

Hu et al., Enhancing Gelation of Doubly Thermosensitive Hydrophilic ABC Linear Triblock Copolymers in Water by Thermoresponsive Hairy Nanoparticles. Macromolecules. 2016;49(15):5502-13. DOI: 10.1021/acs.macromol.6b01156.

Runge et al., Synthesis and Self-Assembly of Bottlebrush Block Copolymers. PMSEPreprints. 2005;92:5-6.

Verduzco et al., Structure, function, self-assembly, and applications of bottlebrush copolymers. Chem. Soc. Rev. 2015;44:2405-20.

Zheng et al., Construction of Smart Supramolecular Polymeric Hydrogels Cross-linked by Discrete Organoplatinum(II) Metallacycles via Post-Assembly Polymerization. J. Am. Chem. Soc. 2016;138(14):4927-37. DOI: 10.1021/jacs.6b01089.

\* cited by examiner

BASP synthesis overview:

Evidence for Additional MM Incorporation by GPC:

Ruthenium is away from the core, accessible for surface functionalization utilizing surface caps:

CORE-TO-SURFACE POLYMERIZATION FOR THE SYNTHESIS OF STAR POLYMERS AND USES THEREOF

RELATED APPLICATIONS

This application claims priority under 35 U.S.C. § 119(e) to U.S. Provisional Application, U.S. Ser. No. 62/528,013, filed Jun. 30, 2017, which is incorporated herein by reference.

BACKGROUND OF THE INVENTION

The synthesis of macromolecules with complex polymer architectures and precisely defined dimensions and functionality has been revolutioned by the advent of efficient, functional-group-tolerant polymerization reactions.[1-12] For example, star polymers are a broad class of branched macromolecular architectures comprising polymer arms radiating from a central branching point, which can be an atom, molecule, or polymer. Based on the chemical compositions of the arms, star polymers can be classified into two broad categories: homo-arm (or regular) star polymers or miktoarm (or hetero-arm) star copolymers. Homo-arm star polymers consist of a symmetrical structure comprising radiating arms with identical chemical composition and similar molecular weight. In contrast, a miktoarm star molecule contains two or more different types of arms with different chemical compositions and/or molecular weights and/or different peripheral functionality. Star polymers can be further classified into more specific categories: homopolymer star, statistical copolymer star, block copolymer star, compositional miktoarm star, molecular weight miktoarm star, end-functional miktoarm star, small compound core strcutured core-structured star, macromolecule core-structured star, network core-structured star, core-functionalized star, arm-functionalized star, and end-functionalized star.

There are several approaches that can be employed for the synthesis of star polymers. The three main approaches are categorized into three types: core-first approach,[13-24] arm-first approach,[24-40] and grafting-onto approach.[41-49] These approaches are mediated by various polymerization methods including ring-opening polymerization, atom transfer radical polymerization, single electron transfer living radical polymerization, nitroxide-mediated living radical polymerization, reversible addition-fragmentation chain transfer radical polymerization, and ring-opening metathesis polymerization.[50] In particular, ring-opening metathesis polymerization (ROMP) has developed into a powerful synthetic platform for innovative polymeric materials of great interest in therapeutics, electronics, and other nanotechnologies. ROMP has been utilized to synthesize star polymers utilizing molybdenum-based catalysts[51-55] and ruthenium-based catalysts.[56-61]

SUMMARY OF THE INVENTION

The synthesis of polymeric drug delivery vehicles free of transition metal catalyst impurities remains a challenge. The construction of brush-arm star polymers (BASP) via ring-opening metathesis polymerization (ROMP) allows for the preparation of well-defined nanoparticles containing drug and/or diagnostic moieties through an "arm-first" approach. A typical ROMP-mediated BASP synthesis includes the following steps: a) a ROMP reaction of macromonomer (MM) to produce a living bottlebrush macroinitiator; b) a ROMP reaction of a crosslinker with the living bottlebrush macroinitiator to produce a living BASP (ROMP-in BASP); and c) a quenching reaction with an additive to end the ROMP reaction. The fate of the initiator at the end of the polymerization process, however, leaves high levels of ruthenium in the dense BASP microgel core that are difficult to remove. Through the additional step of adding macromonomer (same or different) to the living BASP of step b, a process called "core-to-surface" polymerization generates more dense BASP (ROMP-out BASP) that exhibit lower concentrations of ruthenium when compared to ROMP-in BASP. Furthermore, ROMP-out BASP (core-to-surface BASP) provide an opportunity for structural divergence through the incorporation of useful small and large molecules including, but not limited to, pharmaceutical agents (e.g., a therapeutic agent, a diagnostic agent, or a prophylactic agent), diagnostic agents, prophylactic agents, drugs, proteins, peptides, polynucleotides, imaging agents, biopolymers, polymers, small molecules, large molecules, amino acids, polysaccharides, and lipids on the nanoparticle surface. The incorporation of these small and large molecules can be achieved during the synthesis of ROMP-out BASP, wherein the molecule(s) are part of the macromonomer and/or attached to the surface of the ROMP-out BASP through one or more reactions. The methodology described herein to synthesize dense BASP illustrates the importance of the synthetic strategy in the context of low metal concentration as it pertains to medical applications and clinical use, as well as the advantages that core-to-surface BASP have for diverse biomedical applications.

Compositions, methods, reagents, systems, and kits that allow for the preparation and use of brush-arm star polymers are disclosed herein. In certain embodiments, the present disclosure provides a brush-arm star polymer in the form of a particle, such as a nanoparticle. In certain embodiments, the present disclosure provide star polymers formed from core-to-surface polymerization such as ring-opening metathesis polymerization-out brush-arm star polymers and brush-arm star polymer gels. In certain embodiments, the present disclosure provides star polymers formed from two or more of olefin metathesis polymerization reactions with a ruthenium complex; provided that the ruthenium concentration of the star polymer is less than about 450 ppm.

In certain embodiments, the star polymer comprises a polymeric core of repeating units covalently linked to backbone polymeric arms of repeating units each covalently linked to polymeric sidechains (see FIG. 1). In certain embodiments, the polymeric sidechains are each independently selected from the group consisting of polyethers, polyesters, polyacrylamides, polycarbonates, polysiloxanes, polyfluorocarbons, polysulfones, and polystyrenes.

In certain embodiments, the star polymer comprises backbone polymeric arms of Formula (I):

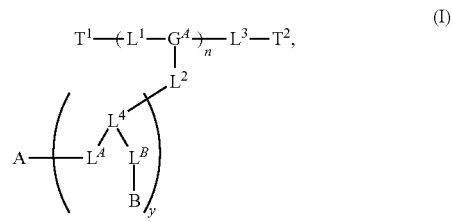

or a salt thereof, wherein:

$G^A$ is optionally substituted alkylene, optionally substituted heteroalkylene, optionally substituted carbocyclylene, optionally substituted heterocylylene, optionally substituted arylene, optionally substituted heteroarylene, or a combination thereof;

each of $L^1$, $L^2$, $L^3$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$ and $T^2$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio, a structure of Formula (I), or a bond to the polymer core as described herein;

n is an integer between 5 and 10000, inclusive;

y is an integer between 1 and 20, inclusive;

A is a polymeric sidechain having a number average molecular weight of about 1000 Da to about 100000 Da, or selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio; and B is hydrogen, an agent as described herein, or a polymeric sidechain having a number average molecular weight of about 1000 Da to about 100000 Da.

In certain embodiments, the star polymer comprises backbone polymeric arms of Formula (I-b):

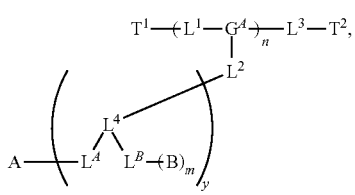

(I-b)

or a salt thereof, wherein:

$G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;

each of $L^1$, $L^2$, $L^3$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$ and $T^2$ is selected from the group consisting of hydrogen, halogen, optionally substituted alkyl, optionally substituted alkenyl, optionally substituted alkynyl, optionally substituted carbocyclyl, optionally substituted hetero-
cyclyl, optionally substituted aryl, optionally substituted heteroaryl, optionally substituted acyl, optionally substituted hydroxyl, optionally substituted amino, optionally substituted thio, a structure of Formula (I), and a bond to the polymeric core as described herein;

n is an integer between 5 and 10000, inclusive;

y is an integer between 1 and 20, inclusive;

A is a polymeric sidechain having a number average molecular weight of about 1000 Da to about 100000 Da, and selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio;

each B independently is hydrogen, an agent as described herein, or a polymeric sidechain having a number average molecular weight of about 1000 Da to about 100000 Da; and m is an integer between 2 and 10, inclusive.

In certain embodiments, the star polymer comprises a polymer core of Formula (II):

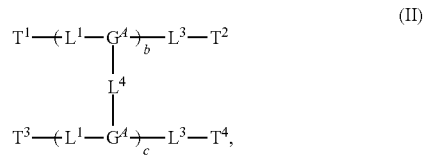

(II)

or a salt thereof, wherein:

$G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;

each of $L^1$, $L^3$, and $L^4$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$, $T^2$, $T^3$, and $T^4$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio, a structure of Formula (I), or a structure of Formula (II); and b and c are independently an integer between 1 and 10000, inclusive.

In certain embodiments, an agent is a pharmaceutical agent (e.g., a therapeutic agent, a diagnostic agent, or a prophylactic agent), diagnostic agent, prophylactic agent, drug, protein, peptide, polynucleotide, imaging agent, biopolymer, polymer, small molecule, large molecule, amino acid, polysaccharide, or lipid.

In certain embodiments, the present disclosure provides a method of preparing a star polymer. In certain embodiments, the method comprising the step of forming the star polymer via polymerization reactions. In certain embodiments, the method further comprises the step of purifying the star polymer via addition of an additive, dialysis, and/or lyophilization. In certain embodiments, the polymerization reactions are ring-opening metathesis polymerization (ROMP) reactions. In certain embodiments, the metal is ruthenium. In certain embodiments, the ruthenium concentration of the star polymer is less than about 450 ppm.

In certain embodiments, the present disclosure provides methods of preparing a ring-opening metathesis polymerization-in brush-arm star polymer (ROMP-in BASP), the method comprising the steps of: (a) providing a macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; and (e) reacting the polymer provided in step (c) and the crosslinker provided in step (d) under conditions suitable to yield a ROMP-in BASP. In certain embodiments, the method further comprises the step of purifying the ROMP-in BASP via addition of an additive, dialysis, and/or lyophilization. In certain embodiments, the reactive moiety of the macromonomer is an olefin. In certain embodiments, the reactive moiety of the macromonomer is a cyclic olefin. In certain embodiments, the reactive moiety of the crosslinker is an olefin. In certain embodiments, the reactive moiety of the crosslinker is a cyclic olefin. In certain embodiments, the polymerization reactions are ring-opening metathesis polymerization (ROMP) reactions. In certain embodiments, the metal is a transition metal complex. In certain embodiments, the metal is ruthenium. In certain embodiments, the ruthenium concentration of the star polymer is less than about 450 ppm.

In certain embodiments, the present disclosure provides a method of preparing a ring-opening metathesis polymerization-out brush-arm star polymer (ROMP-out BASP), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; (e) reacting the polymer provided in step (c) and the crosslinker provided in step (d) under conditions suitable to effect a polymerization reaction and yield a ROMP-in BASP; (f) providing a second macromonomer comprising one or more polymeric sidechains and one or more reactive moieties; and (g) reacting the ROMP-in BASP provided in step (e) and the macromonomer provided in step (f) under conditions suitable to effect a polymerization reaction and yield a ROMP-out BASP. In certain embodiments, the method further comprises the step of purifying the star polymer via addition of an additive, dialysis, and/or lyophilization. In certain embodiments, the first macromonomer is the same as the second macromonomer. In certain embodiments, the first macromonomer is different from the second macromonomer. In certain embodiments, the reactive moieties of the macromonomers are olefins. In certain embodiments, the reactive moieties of the macromonomers are cyclic olefins. In certain embodiments, the reactive moiety of the crosslinker is an olefin. In certain embodiments, the reactive moiety of the crosslinker is a cyclic olefin. In certain embodiments, the polymerization reactions are ring-opening metathesis polymerization (ROMP) reactions. In certain embodiments, the metal is a transition metal complex. In certain embodiments, the metal is ruthenium. In certain embodiments, the ruthenium concentration of the star polymer is less than about 450 ppm.

In certain embodiments, the present disclosure provides a method of preparing a brush-arm star polymer gel (BASP gel), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a first crosslinker comprising one or more reactive moieties; (e) reacting the polymer provided in step (c) and the crosslinker provided in step (d) under conditions suitable to effect a polymerization reaction and yield a ROMP-in BASP; (f) providing a second macromonomer comprising one or more polymeric sidechains and one or more reactive moieties; (g) reacting the ROMP-in BASP provided in step (e) and the macromonomer provided in step (f) under conditions suitable to effect a polymerization reaction and yield a ROMP-out BASP; (h) providing a second crosslinker comprising one or more reactive moieties; and (i) reacting the ROMP-out BASP provided in step (g) and the crosslinker provided in step (h) under conditions suitable to effect a polymerization reaction and yield a BASP gel. In certain embodiments, the method further comprises the step of purifying the BASP gel via addition of an additive, dialysis, and/or lyophilization. In certain embodiments, the first macromonomer is the same as the second macromonomer. In certain embodiments, the first macromonomer is different from the second macromonomer. In certain embodiments, the reactive moieties of the macromonomers are olefins. In certain embodiments, the first crosslinker is the same as the second crosslinker. In certain embodiments, the first crosslinker is different from the second macromonomer. In certain embodiments, the reactive moieties of the crosslinkers are olefins. In certain embodiments, the reactive moieties of the crosslinkers are cyclic olefins. In certain embodiments, the polymerization reactions are ring-opening metathesis polymerization (ROMP) reactions. In certain embodiments, the metal is a transition metal complex. In certain embodiments, the metal is ruthenium. In certain embodiments, the ruthenium concentration of the star polymer is less than about 450 ppm.

In certain embodiments, the present disclosure provides a method of preparing a surface-functionalized ring-opening metathesis polymerization-out brush-arm star polymer (ROMP-out BASP), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; (e) reacting the polymer provided in step (c) and the crosslinker provided in step (d) under conditions suitable to effect a polymerization reaction and yield a ROMP-in BASP; (f) providing a second macromonomer comprising one or more polymeric sidechains and one or more reactive moieties; (g) reacting the ROMP-in BASP provided in step (e) and the macromonomer provided in step (f) under conditions suitable to effect a polymerization reaction and yield a ROMP-out BASP; (h) providing a surface capping reagent comprising one or more reactive moieties; and (i) reacting the ROMP-out BASP with the surface capping reagent in step (h) under conditions suitable to effect a polymerization reaction and yield a surface-functionalized ROMP-out BASP. In certain embodiments, the method further comprises the step of purifying the surface-functionalized ROMP-out BASP via addition of an additive, dialysis, and/or lyophilization. In certain embodiments, the first macromonomer is the same as the second macromonomer. In certain embodiments, the first macromonomer is different from the second macromonomer. In certain embodiments, the reactive moieties of the macromonomers are olefins. In certain embodiments, the reactive moieties of the crosslinkers are olefins. In certain embodiments, the polymerization reactions are ring-opening metathesis polymerization (ROMP) reactions. In certain embodiments, the metal is a transition metal complex. In certain embodiments, the metal is ruthenium. In certain embodiments, the ruthenium concentration of the star polymer is less than about 450 ppm.

In certain embodiments, the macromonomer is of Formula (III):

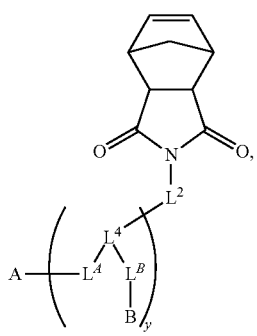

(III)

or a salt thereof, wherein:

each of $L^2$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

y is an integer between 1 and 20, inclusive;

A is a polymeric sidechain having a number average molecular weight of about 1000 Da to about 100000 Da, and selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio; and B is a hydrogen, pharmaceutical agent (e.g., a therapeutic agent, a diagnostic agent, or a prophylactic agent), a drug, a protein, a polynucleotide, an imaging agent, a biopolymer, a polymer, a small molecule, a large molecule, an amino acid, a polysaccharide, a lipid, or a polymeric sidechain having a number average molecular weight of about 1000 Da to about 100000 Da.

In certain embodiments, the macromonomer is of Formula (III-b):

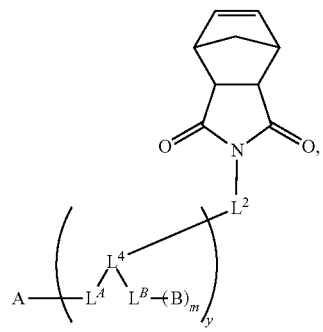

(III-b)

or a salt thereof, wherein:

each of $L^2$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

y is an integer between 1 and 20, inclusive;

A is a polymeric sidechain having a number average molecular weight of about 1000 Da to about 100000 Da, or selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio;

each B is independently hydrogen, pharmaceutical agent, a drug, a protein, a polynucleotide, an imaging agent, a biopolymer, a polymer, a small molecule, a large molecule, an amino acid, a polysaccharide, a lipid, or polymeric sidechain having a number average molecular weight of about 1000 Da to about 100000 Da; and m is an integer between 2 and 10, inclusive.

In certain embodiments, the crosslinker is of Formula (IV):

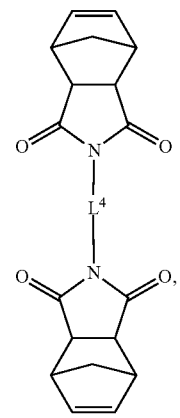

(IV)

or a salt thereof, wherein:

$L^4$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof.

In certain embodiments, the present disclosure provides compositions comprising a star polymer described herein. In certain embodiments, the composition further comprises a pharmaceutically acceptable excipient. In certain embodiments, the composition comprises a therapeutically effective amount of a star polymer described herein.

In certain embodiments, the present disclosure describes kits comprising a star polymer described herein, or a composition comprising a star polymer, and instructions for use.

In certain embodiments, the present disclosure describes methods of treating or preventing a disorder, disease, or condition comprising administering to a subject in need thereof a therapeutically effective amount of a star polymer or composition described herein.

In certain embodiments, the present disclosure provides compounds, polymers, particles, nanoparticles, compositions, and kits described herein for use in a method of the present disclosure.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, $\sim$ is a single bond where the stereochemistry of the moieties immediately attached thereto is not specified, --- is absent or a single bond, and $=$ or $\equiv$ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo.

In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$,

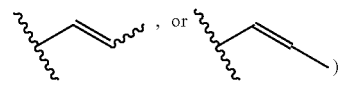

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-10}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$).

Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, —$NO_2$, —C(=O)$R^{aa}$, —$CO_2R^{aa}$, —C(=O)N($R^{bb}$)$_2$, —OC(=O)$R^{aa}$, —$OCO_2R^{aa}$, —OC(=O)N($R^{bb}$)$_2$, —$NR^{bb}C$(=O)$R^{aa}$, —$NR^{bb}CO_2R^{aa}$, or —$NR^{bb}C$(=O)N($R^{bb}$)$_2$. In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, or —$NO_2$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3$, —OP(=O)$_2R^{aa}$, —OP(=O)($R^{aa}$)$_2$, —OP(=O)($OR^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}C$(=O)N($R^{bb}$)$_2$, —$NR^{bb}C$(=$NR^{bb}$)N($R^{bb}$)$_2$, —$NR^{bb}SO_2R^{aa}$, —$NR^{bb}P$(=O)($OR^{cc}$)$_2$, and —$NR^{bb}P$(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —$SO_2N$($R^{bb}$)$_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$, —C(=$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$ (OR$^{cc}$), wherein R$^{aa}$ and R$^{cc}$ are as defined herein.

The term "phosphino" refers to the group —P(R$^{cc}$)$_3$, wherein R$^{cc}$ is as defined herein. An exemplary phosphino group is triphenylphosphine.

The term "phosphono" refers to the group —O(P=O)(OR$^{cc}$)R$^{aa}$, wherein R$^{aa}$ and R$^{cc}$ are as defined herein.

The term "phosphoramido" refers to the group —O(P=O)(NR$^{bb}$)$_2$, wherein each R$^{bb}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "heteroatom" refers to an atom that is not hydrogen or carbon. In certain embodiments, the heteroatom is a nitrogen, oxygen, or sulfur. In certain embodiments, the heteroatom is a nitrogen or oxygen. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymer" refers to a molecule including two or more (e.g., 3 or more, 4 or more, 5 or more, 10 or more) repeating units which are covalently bound together. In certain embodiments, a polymer comprises 3 or more, 5 or more, 10 or more, 50 or more, 100 or more, 500 or more, 1000 or more, 2000 or more, 3000 or more, 4000 or more, 5000 or more, 6000 or more, 7000 or more, 8000 or more, 9000 or more, or 10000 or more repeating units. In certain embodiments, a polymer comprises more than 5000 repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. A "graft polymer" is a segmented copolymer with a linear backbone of one composite and randomly distributed branches of another composite. The major difference between graft polymers and bottlebrush polymers (or brush-arm polymers) is the grafting density. The targeted graft density for bottlebrush polymers is that in at least one segment of the copolymer is one graft from each backbone monomer unit. A "star polymer" is a polymer that consists of several polymers chains connected at a core atom, core molecule, or core polymer. Polymers may be natural (such as biopolymers like naturally occurring polypeptides), or synthetic (e.g., non-naturally occurring). A polymer may have an overall molecular weight of 50 Da or greater, 100 Da or greater, 500 Da or greater, 1000 Da or greater, 2000 Da or greater, 5000 Da or greater, 10000 Da or greater, 20000 Da or greater, or 50000 Da or greater.

The terms "living polymer" and "living polymerization" refer a polymerization where the ability of a growing polymer chain to terminate has been removed. Chain termination and chain transfer reactions are absent, and the rate of the chain initiation is also much larger than the rate of chain propagation.

The terms "number average molecular weight," "number average molar mass," and "$M_n$" are measurements of the molecular mass of a polymer. The number average molecular mass is the ordinary arithmetic mean or average of the molecular masses of the individual polymers. It is determined by measuring the molecular mass of n polymer molecules, summing the masses, and dividing by n. For example, a polymer having 100 repeating units of a monomer with a molecular weight of 100 g/mol would have a number average molecular weight ($M_n$) of 10,000 g/mol [$M_n$=(100)*(100 g/mol)/(1)=10,000 g/mol)]. The number average molecular mass of a polymer can be determined by gel permeation chromatography, viscometry via the Mark-Houwink equation, colligative methods such as vapor pressure osmometry, end-group determination, or $^1$H NMR (nuclear magnetic resonance).

The term "monomer" refers to a molecule that may be covalently joined to other monomers to form a polymer. The process by which the monomers are combined to form a polymer is called polymerization. A macromolecule with a reactive moiety that enables it to act as a monomer is called a macromonomer. Molecules made of a small number of monomer units (up to a few dozen) are called oligomers.

Inductively coupled plasma mass spectrometry (ICP-MS) is a type of mass spectrometry which is capable of detecting metals and several non-metals at concentrations as low as one part in $10^{15}$ (part per quadrillion, ppq) on non-interfered low-background isotopes.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahydrofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. In certain embodiments, the animal is a mouse. In certain embodiments, the animal is a human. The animal may be a male or female at any stage of development. The animal may be a transgenic animal or genetically engineered animal. In certain embodiments, the subject is a non-human animal.

The term "administer," "administering," or "administration" refers to implanting, absorbing, ingesting, injecting, inhaling, or otherwise introducing a polymer described herein or generated as described herein, or a composition thereof, in or on a subject.

As used herein, the term "salt" refers to any and all salts, and encompasses pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents.

A "large organic molecule" or "large molecule" refers to an organic compound that is not a small molecule. In certain embodiments, the molecular weight of a large molecule is greater than about 2,000 g/mol, greater than about 3,000 g/mol, greater than about 4,000 g/mol, or greater than about 5,000 g/mol. In certain embodiments, the molecular weight of a large molecule is at most about 100,000 g/mol, at most about 30,000 g/mol, at most about 10,000 g/mol, at most about 5,000 g/mol, or at most about 2,000 g/mol. Combinations of the above ranges (e.g., greater than about 2,000 g/mol and at most about 10,000 g/mol) are also possible. In certain embodiments, the large molecule is a therapeutically active agent such as a drug (e.g., a molecule approved by the U.S. Food and Drug Administration as provided in the Code of Federal Regulations (C.F.R.)). The large molecule may also be complexed with one or more metal atoms and/or metal ions. In this instance, the large molecule is also referred to as an "large organometallic compound."

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the macromonomers or polymers disclosed herein comprise an agent(s), e.g., a first therapeutic agent (e.g., at least one (including, e.g., at least two, at least three).

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the polymer described herein incorporates one therapeutic agent or prodrug thereof. In some embodiments, the polymer described herein incorporates more than one therapeutic agents or prodrugs.

Exemplary agents, e.g., a therapeutic agents, in the BASPs include, but are not limited to, those found in *Harrison's Principles of Internal Medicine*, 13th Edition, Eds. T. R. Harrison et al. McGraw-Hill N.Y., N.Y.; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, exemplary therapeutic agents in the BASPs include, but are not limited to, one or more of the agents listed in Paragraph 0148 of U.S. Pat. No. 9,381,253, incorporated by reference herein.

In other embodiments, exemplary therapeutic agents in the BASPs include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenviroment modulators disclosed, e.g., in Paragraphs 113-121, of WO 2013/169739, incorporated herein by reference. In some embodiments, the BASP-composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics and immunotherapies) in a tumor or tumor vasculature, in the subject.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The term "imaging" refers to a technique and process of creating visual representations of the interior of a body or portion thereof (e.g., brain, heart, lung, liver, kidney, spleen, muscle, tissue, and tumor) for clinical analysis and medical intervention, as well as visualization of the function of organs and/or tissues. Medical imaging seeks to reveal internal structures hidden by the skin and bones, as well as to diagnose and sometimes treat disease. Medical imaging also establishes a database of normal anatomy and physiology to make it possible to identify abnormalities. Examples of imaging modalities include, but are not limited to, radiography, magnetic resonance imaging (MRI), nuclear medicine, ultrasound, elastography, tactile imaging, photoacoustic imaging, tomography, echocardiography, near-infrared fluorescence (NIRF) imaging, and magnetic particle imaging.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an at anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a P anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, and rutinose. Exemplary trisaccharides include, but are not limited to, isomaltotriose, nigerotriose, maltotriose, melezitose, maltotriulose, raffinose, and kestose.

The term "crosslinker" refers to a compound that allows for two or more molecules or polymers to be joined by a covalent bond. In certain embodiments, the crosslinker results in a covalent attachment between two polymers.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the invention. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "ring-opening metathesis polymerization (ROMP)" refers to a type of olefin metathesis chain-growth polymerization that is driven by the relief of ring strain in cyclic olefins (e.g. norbornene, cyclopentene). The catalysts used in the ROMP reaction include $RuCl_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium(II), dichloro[1,3-Bis(2-methylphenyl)-2-imidazolidinylidene](benzylidene)(tricyclohexylphosphine) ruthenium(II), dichloro[1,3-bis(2,4,6-trimethylphenyl)-2-imidazolidinylidene][3-(2-pyridinyl)propylidene]ruthenium(II), dichloro(3-methyl-2-butenylidene)bis (tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis (tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium(II) (Grubbs II), and dichloro[1,3-bis(2,4,6-trimethylphenyl)-2-imidazolidinylidene](benzylidene)bis(3-bromopyridine)ruthenium(II) (Grubbs III).

The term "effective metal concentration" or "metal concentration" is defined as the weight of metal (milligrams) per weight of polymer (kilograms) and is designated parts per million (ppm). In certain embodiments, the metal is selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, and meitnerium. In particular, the ruthenium concentration of a ruthenium complex is measured in the present disclosure.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject, with a prophylactically effective amount of an agent, who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

A "prophylactically effective amount" of an agent described herein is an amount sufficient to prevent a condition, or one or more symptoms associated with the condition or prevent its recurrence. A prophylactically effective amount of an agent means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "condition," "disease," and "disorder" are used interchangeably.

BRIEF DESCRIPTION OF THE DRAWINGS

The accompanying drawings, which constitute a part of this specification, illustrate several exemplary embodiments of the invention and together with the description, serve to explain certain principles of the invention. The embodiments disclosed in the drawings are exemplary and do not limit the scope of this disclosure.

DETAILED DESCRIPTION OF CERTAIN EMBODIMENTS

Figure 1:
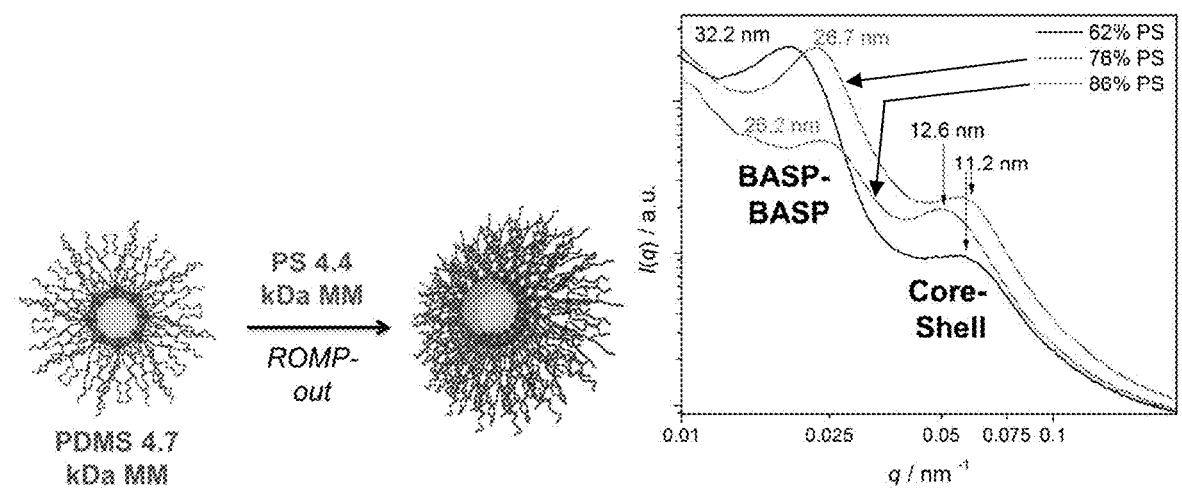
FIG. 1: Miktoarm star polymer (PS/PDMS) provides structural proof that the final star polymers contain macromonomers from two separate ROMP events. SAXS shows contrast between the BASP core/shell and between PS/PDMS. PS=polystyrene, PDMS=poly(dimethylsiloxane), SAXS=small-angle X-ray scattering.
Figure 2:
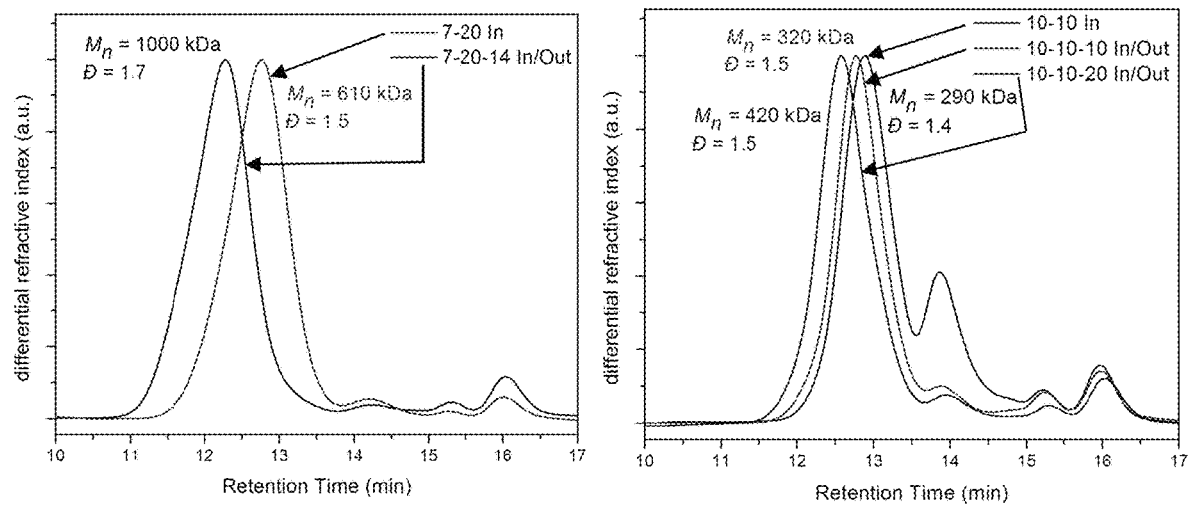
FIG. 2: Examples of GPC traces from BASP vs. core-to-surface BASPs. Increasing MM during the ROMP-out process leads to shorter GPC retention times. GPC=gel permeation chromatography, MM=macromonomer.
Figure 3:
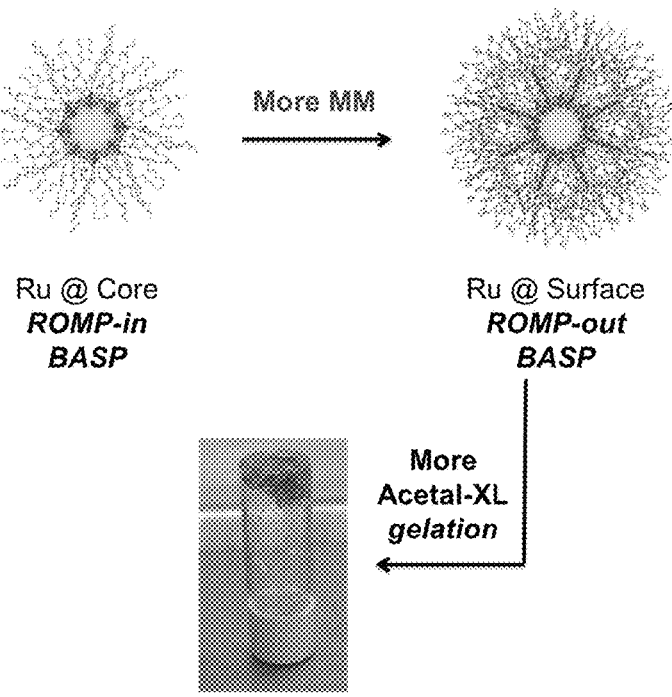
FIG. 3: Overview of ROMP-out process and "BASP protection" via gelation.
Figure 4:
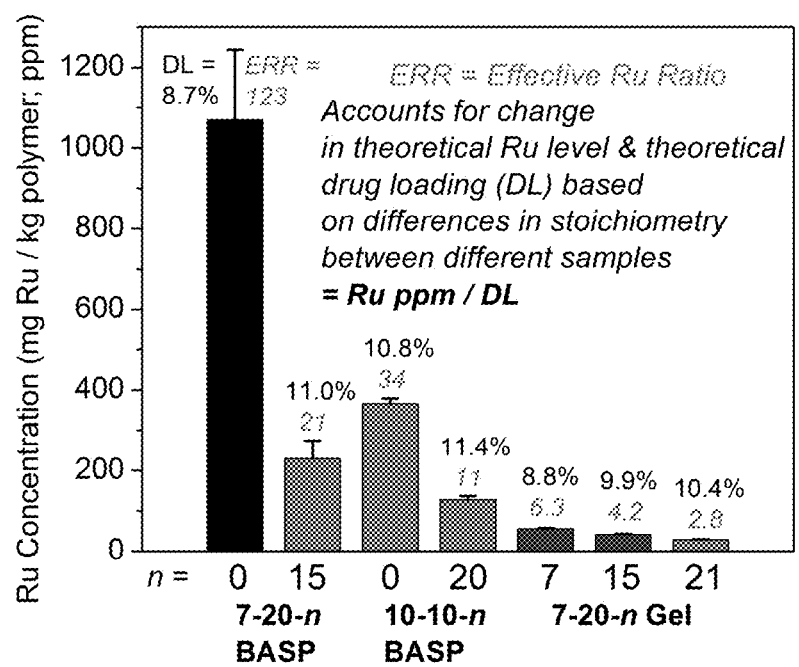
FIG. 4: Summary of residual ruthenium depending on reaction conditions (ROMP-in BASP, ROMP-out BASP, BASP gel). ROMP-in BASP=standard conditions (MM then Acetal-XL); ROMP-out BASP=MM then Acetal-XL then MM; BASP gel=ROMP-out BASP+Acetal-XL. Reactions to form BASPs were quenched, purified, and analyzed to determine the metal concentration.
Figure 5:
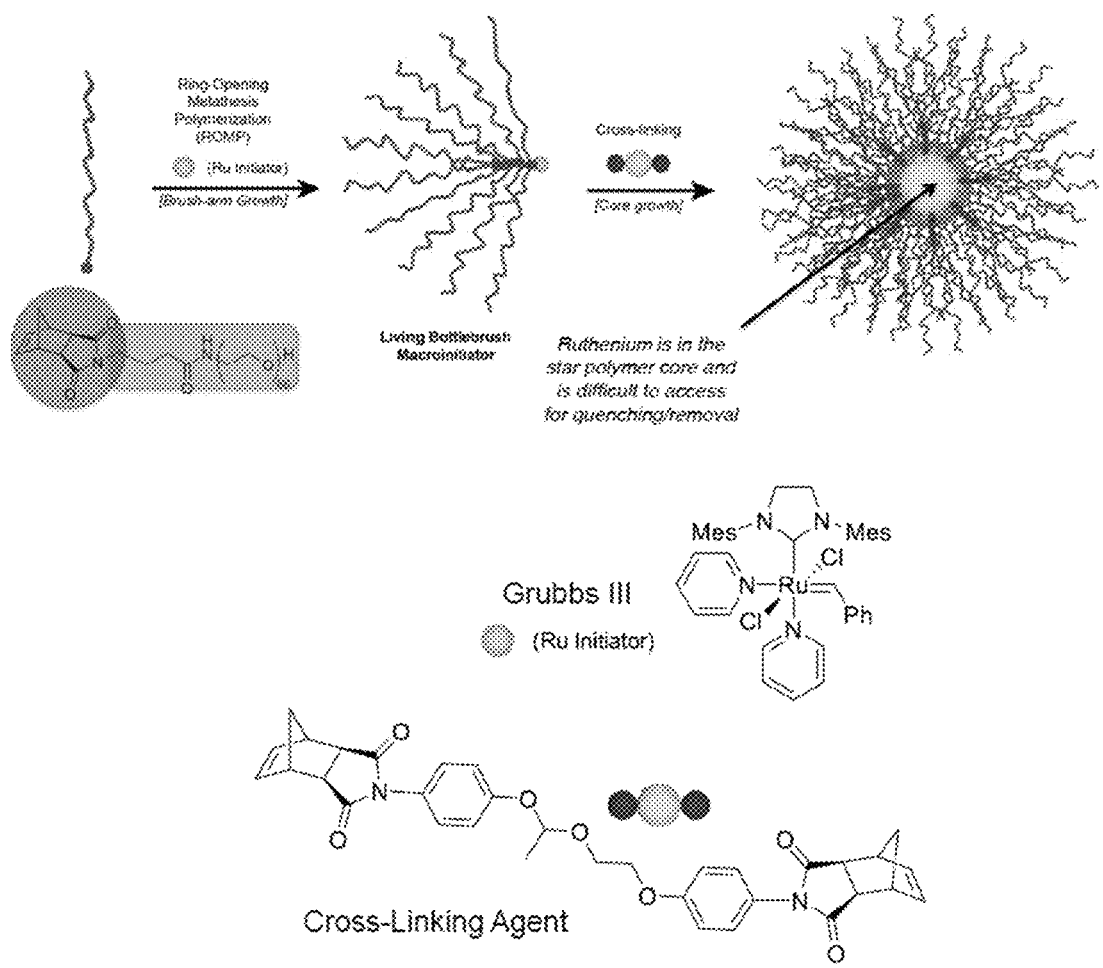
FIG. 5: BASP synthesis overview. It is essential to remove ruthenium (derived from Grubbs III initiator) from the polymer for translation of the technology to in vivo applications.
Figure 6:
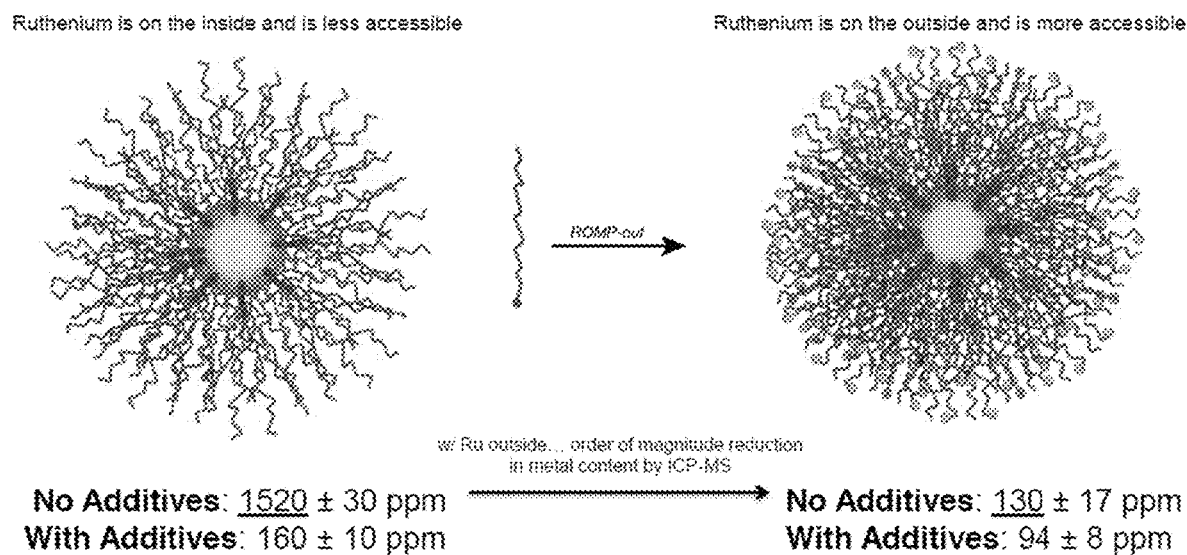
FIG. 6: ROMP-out as a means to make ruthenium more accessible for removal. Ruthenium concentration levels (ppm=mg Ru/kg BASP sample) reported as mean values from three ICP-MS trials with standard deviations given as error bars. Workup: dialysis (nanopure $H_2O$, 1 kDa MWCO RC) then lyophilization. Additives=trishydroxymethylphosphine (THMP) (100 equiv) and excess DMSO.
Figure 7:
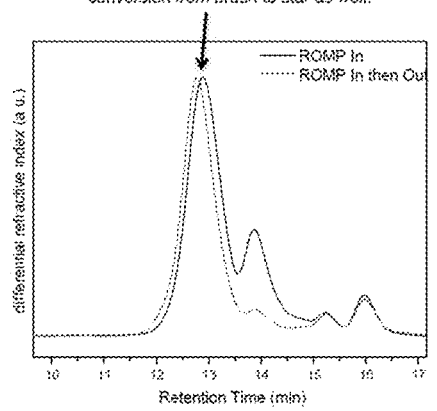
FIG. 7: Evidence for Additional MM Incorporation by GPC. BASP size by dynamic light scattering (~23 nm) is consistent with typical sizes observed for "ROMP-in" BASPs with the same stoichiometry (brush-length: 10 units, equivalents of cross-linker: 10).
Figure 7:
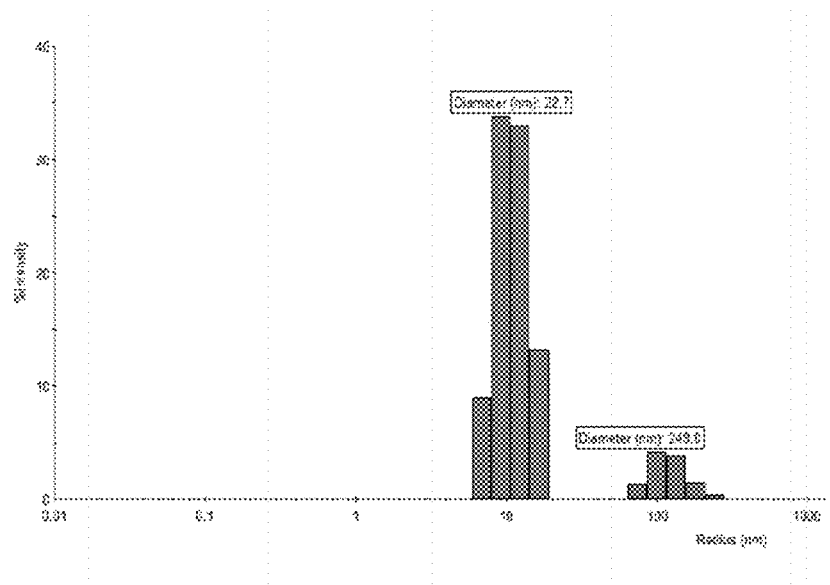
Figure 8:
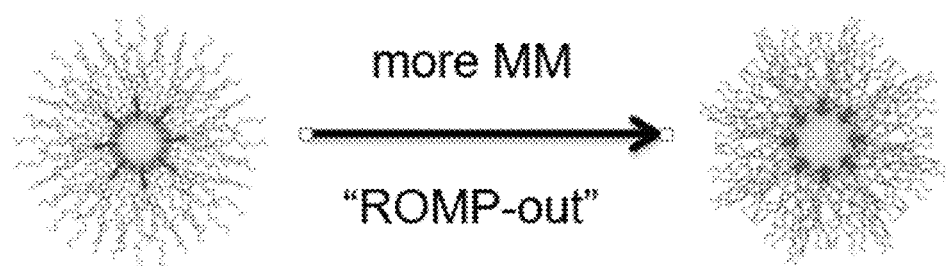
FIG. 8: ROMP-out BASP can be terminated with surface capping reagents (surface caps).
Figure 8:
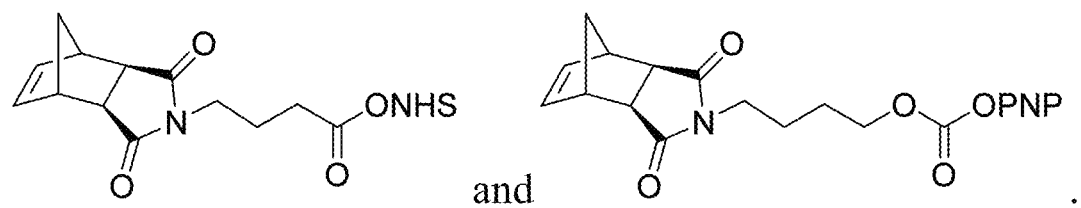
Figure 9:
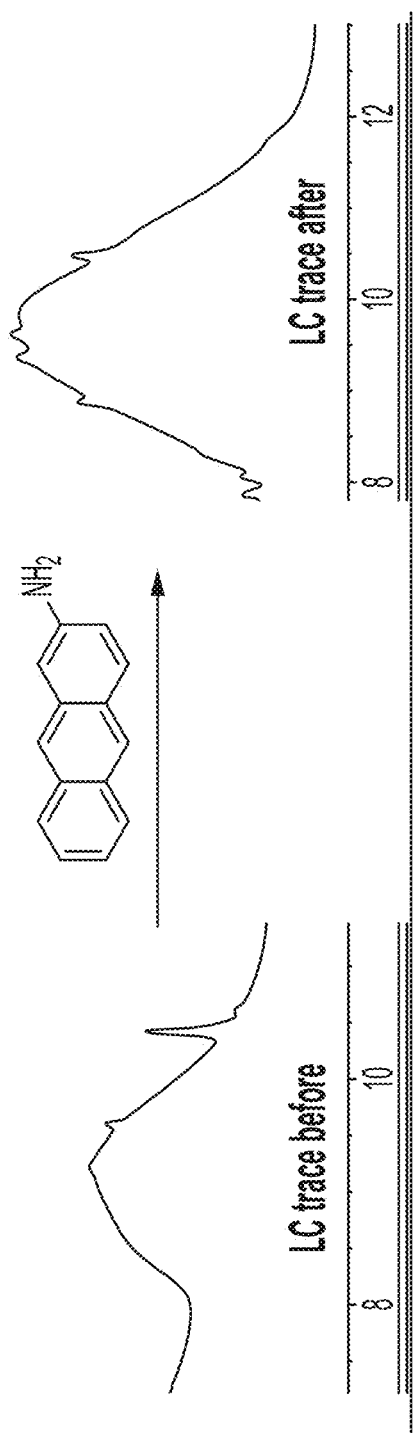
FIG. 9: Surface-functionalized ROMP-out BASPs can be treated with an appropriate nucleophile, such as aminoanthracene. Functionalization with nucleophile can be observed by a shift in the LC retention time.
Figure 10:
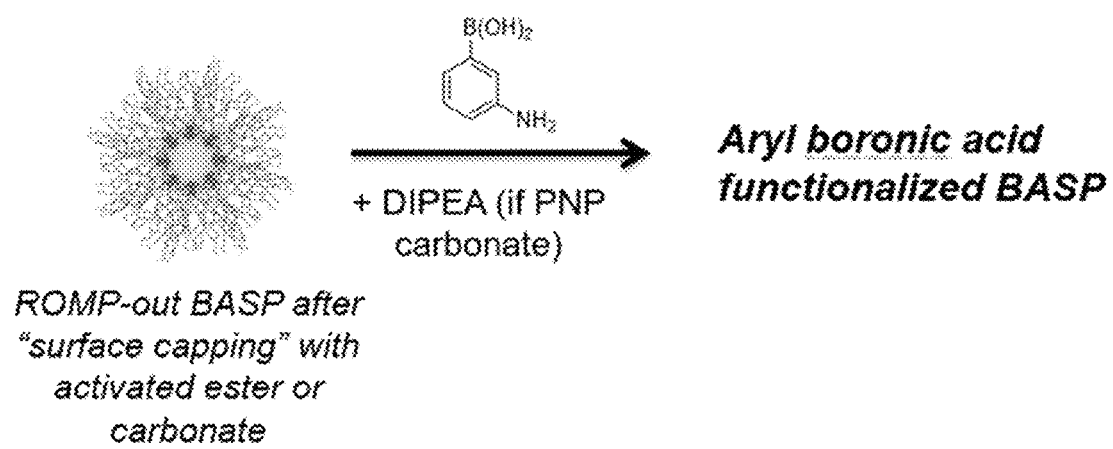
FIG. 10: Surface-functionalized ROMP-out BASPs functionalized by surface caps containing an activated ester or activated carbonate can undergo nucleophilic substitution with aryl boronic acids containing at least one amino group.
Figure 11:
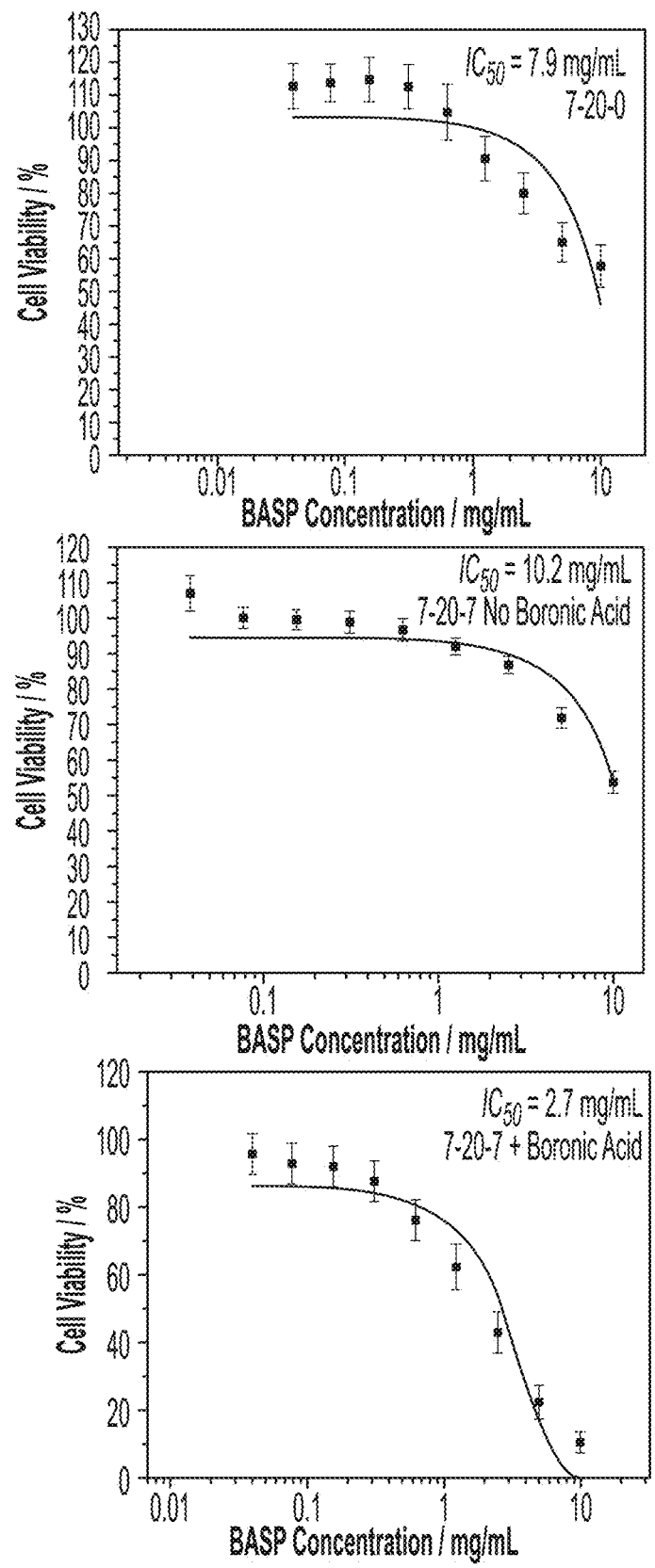
FIG. 11: Cellular internalization for ROMP-in BASP-7-20-0 (left), ROMP-out BASP-7-20-7 (middle), and surface-functionalized ROMP-out BASP-7-20-7 (right) functionalized with aryl boronic acid containing an amino group. The data indicates that the boronic acid surface-functionalized ROMP-out BASP provides higher cellular internalization than ROMP-in BASP and ROMP-out BASP not containing boronic acids on the surface. The notation used in the figures is $m_1$-n-$m_2$, where $m_1$ is equivalents of "ROMP-in" macromonomer relative to the metal complex capable of initiating ROMP (Grubbs III), n is equivalents of crosslinker, and $m_2$ equivalents of "ROMP-out" macromonomer
Figure 12:
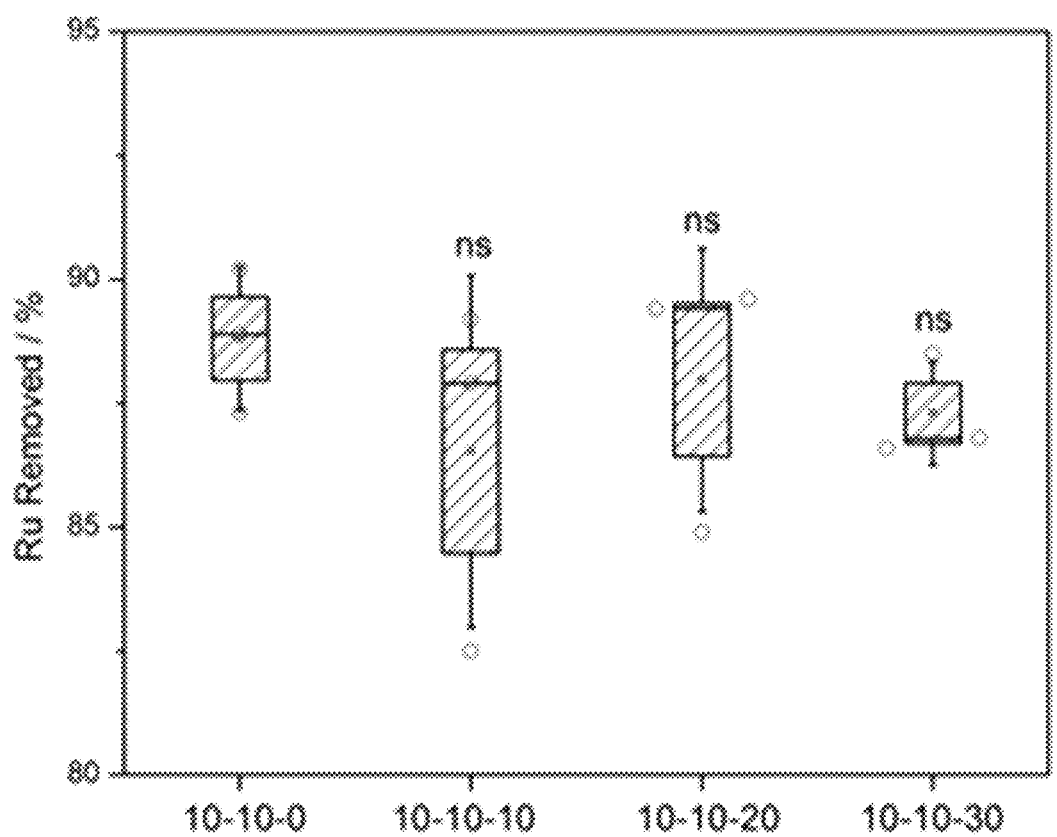
FIG. 12: ROMP-out BASP do not provide a statistically significant difference of removed ruthenium compared to ROMP-in BASP.
Figure 13:
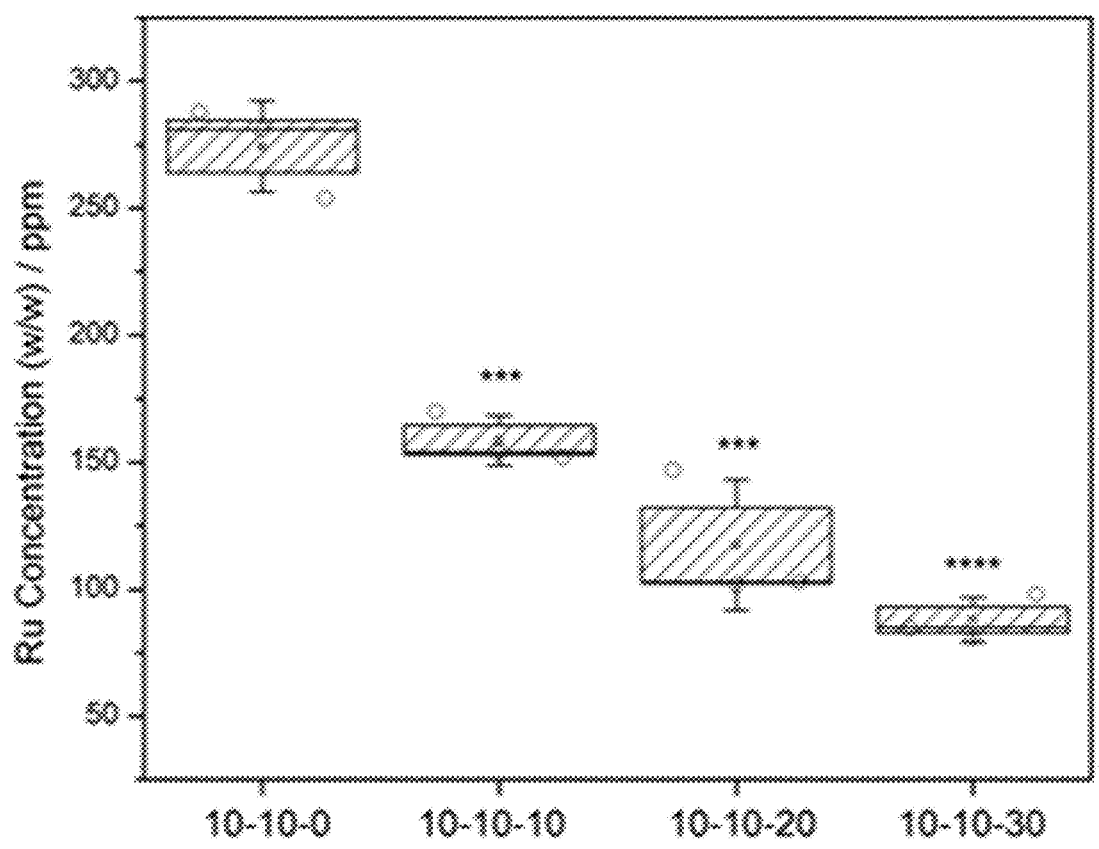
FIG. 13: ROMP-out BASP are denser than ROMP-in BASP, which results in the concentration of ruthenium being lower for ROMP-out BASP when compared to the ROMP-in BASP.
Figure 14A:
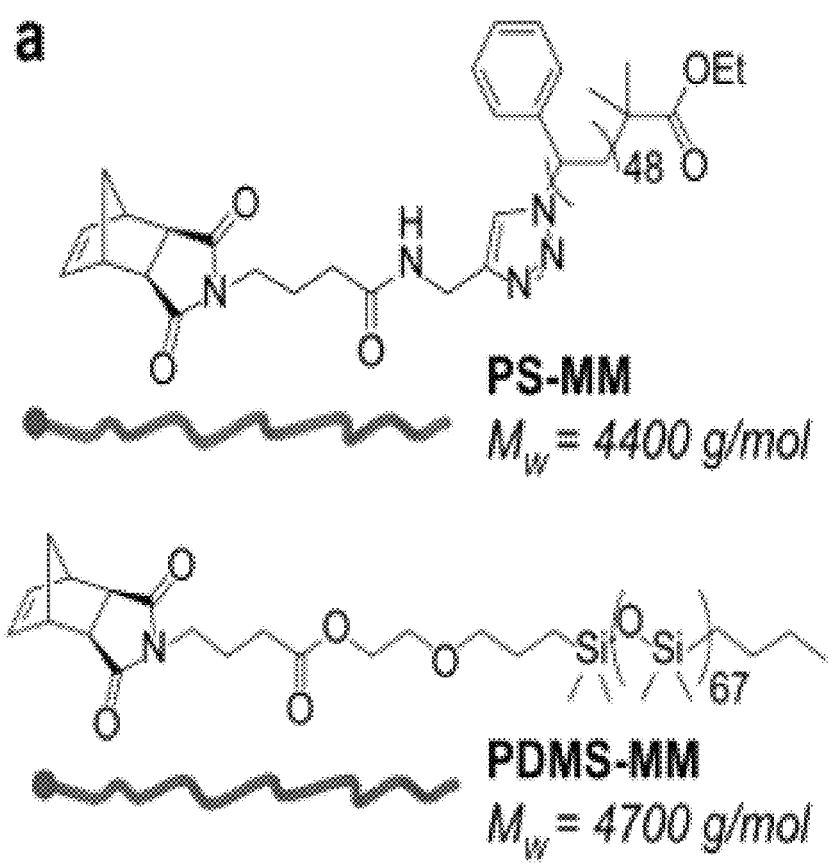
FIGS. 14A to 14D: 14A) The two macromonomers PS-MM and PDMS-MM are shown. 14B and 14D) ROMP-in BASP method is used to prepare PDMS-BASP and ROMP-out BASP method is used to prepare PDMS/PS-BASP. Small-angle X-ray scattering (SAXS) shows that PDMS-BASP contained a single peak, while PDMS/PS-BASP contained two peaks indicating that the PDMS and PS brushes lead to formation of Janus-type structures. 14C) The reaction of PDMS-BASP with PS-MM to generate PDMS/PS-BASP.
Figure 14B:
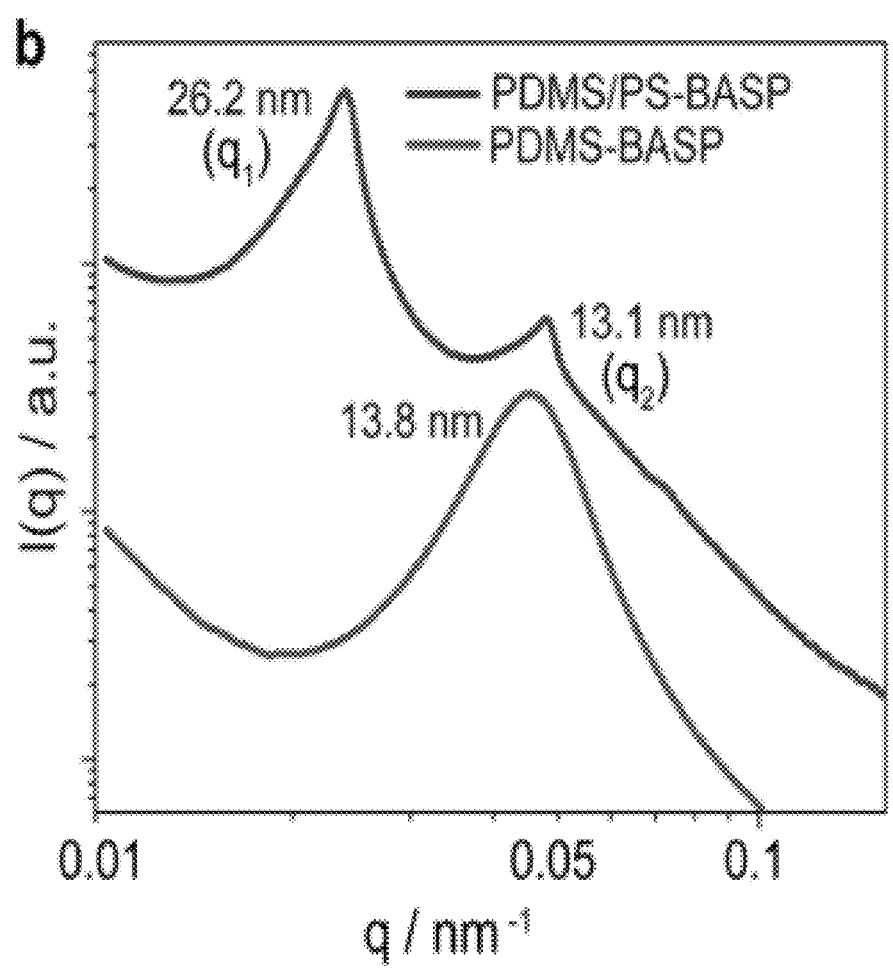
Figure 14C:
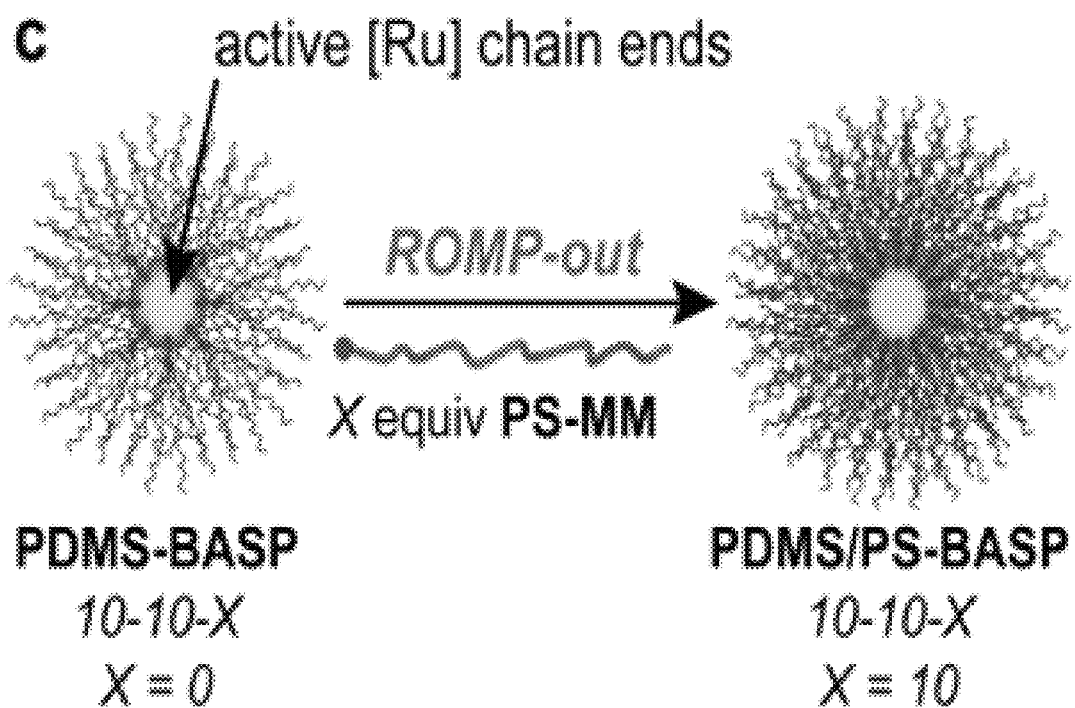
Figure 14D:
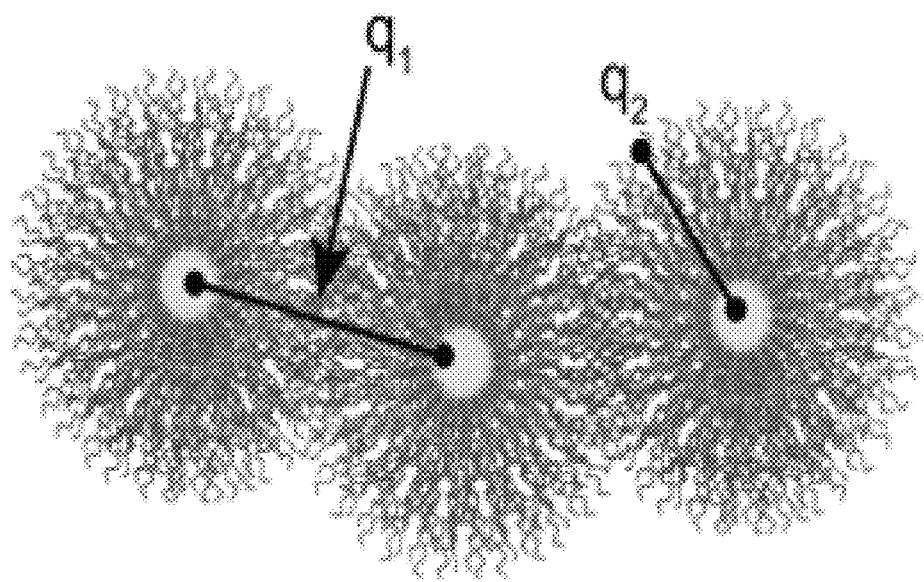
Figure 15A:
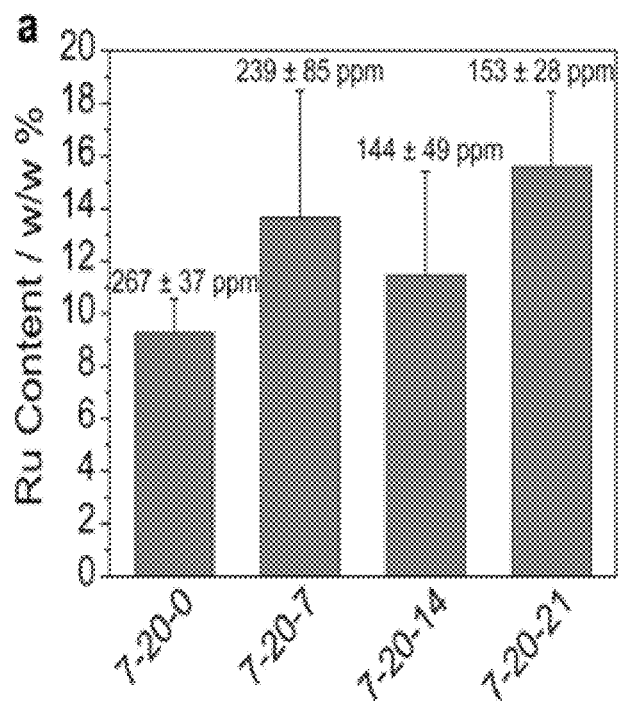
FIGS. 15A and 15B: There is no significant difference between ruthenium content (w/w %) in 10-10-0 BASPs compared to 7-20-0 BASPs; ≥ca. 90% of Ru is removed in both examples despite differences in stoichiometry. Ruthenium concentration does not change significantly in either family upon "ROMP-out" (X=10, 20, 30). However, the addition of more mass during ROMP-out effectively dilutes the total Ru concentration (ppm).
Figure 15B:
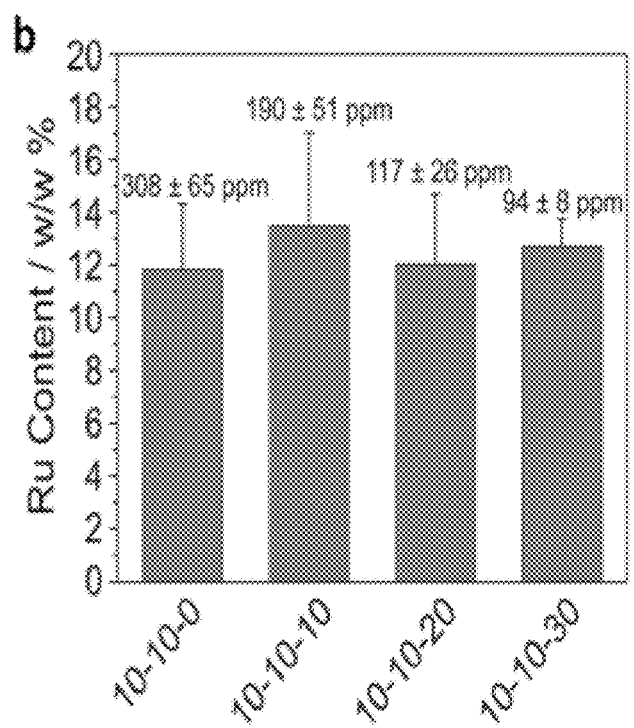
Figure 16A:
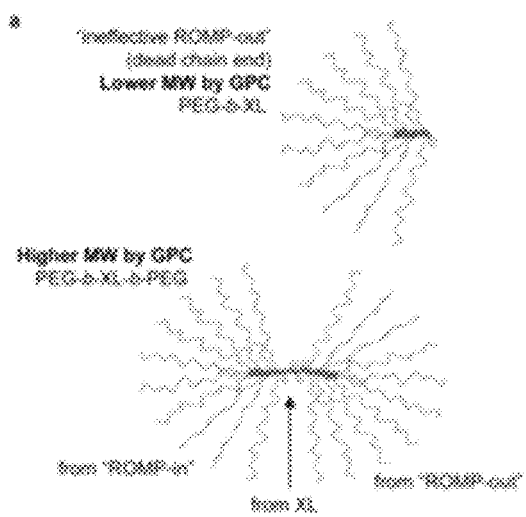
FIGS. 16A to 16C: ROMP-out efficiencies can be measured using GPC to determine the percentage of chain-ends extending during ROMP-out. For the 10-10-X series, 60-81% of chain ends are extended during "ROMP-out". For the 7-20-X series was less efficient during "ROMP-out", affording 47-73% extended chain ends.
Figure 16B:
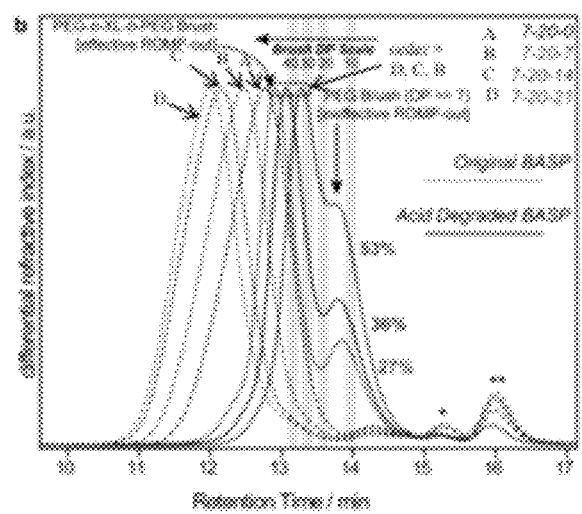
Figure 16C:
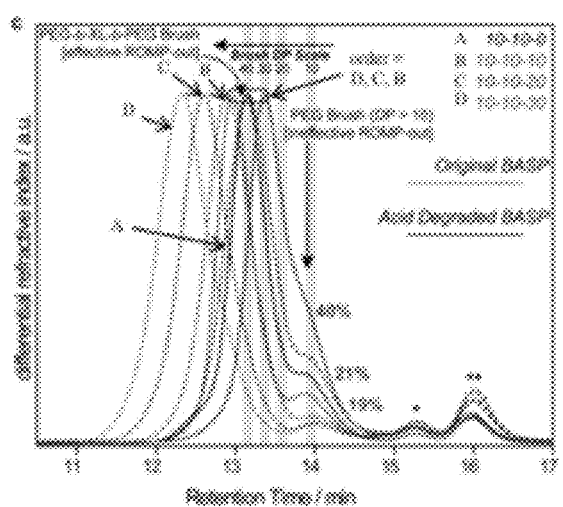

The present disclosure provides methods, compounds, particles (e.g., nanoparticles, microparticles), compositions, systems, reagents, and kits focused on the synthesis and uses of star polymers. In certain embodiments, the star polymers are brush-arm star polymers (BASPs). In certain embodiments, the brush-arm star polymers are comprised of brush-arm polymers containing polymeric sidechains covalently linked to a polymeric core via crosslinkers.

In certain embodiments, the present disclosure describes methods to prepare star polymers. In certain embodiments, the methods provide ROMP-in BASPs. In certain embodiments, the methods provide ROMP-out BASPs. In certain embodiments, the methods provide BASP gels. In certain embodiments, the methods utilize one or more olefin metathesis polymerization reactions to prepare the star polymers. In certain embodiments, the olefin metathesis polymerization reaction is performed with a metal complex. In certain embodiments, the methods comprise a purification step to remove the metal.

In certain embodiments, the present disclosure describes methods to prepare surface-functionalized ROMP-out BASP. In certain embodiments, a surface-functionalized ROMP-out BASP is formed from reacting a ROMP-out BASP with a surface capping reagent. In certain embodiments, a surface-functionalized ROMP-out BASP is formed from reacting a ROMP-out BASP capped by a surface capping reagent containing an activated ester or activated carbonate with a nucleophile.

Brush-Arm Star Polymers (BASPs)

One aspect of the present disclosure relates to star polymers (i.e., ROMP-in BASPs, ROMP-out BASPs, and BASP gels) formed from two or more olefin metathesis polymerization reactions with a metal complex; provided that the metal concentration of the star polymer is less than about 450 ppm. In certain embodiments, the metal of the metal complex is a transition metal. In certain embodiments, the transition metal is ruthenium. In certain embodiments, the ruthenium concentration of the star polymer is less than about 400 ppm. In certain embodiments, the ruthenium concentration of the star polymer is less than about 350 ppm. In certain embodiments, the ruthenium concentration of the star polymer is less than about 300 ppm. In certain embodiments, the ruthenium concentration of the star polymer is less than about 250 ppm. In certain embodiments, the ruthenium concentration of the star polymer is less than about 200 ppm. In certain embodiments, the ruthenium concentration of the star polymer is less than about 150 ppm. In certain embodiments, the ruthenium concentration of the star polymer is less than about 100 ppm. In certain embodiments, the ruthenium concentration of the star polymer is less than about 50 ppm. In certain embodiments, the ruthenium concentration of the star polymer is below the detectable limit measurable by inductively coupled plasma mass spectrometry (ICP-MS).

In certain embodiments, the transition metal is osmium. In certain embodiments, the osmium concentration of the star polymer is less than about 450 ppm. In certain embodiments, the osmium concentration of the star polymer is less than about 400 ppm. In certain embodiments, the osmium concentration of the star polymer is less than about 350 ppm. In certain embodiments, the osmium concentration of the star polymer is less than about 300 ppm. In certain embodiments, the osmium concentration of the star polymer is less than about 250 ppm. In certain embodiments, the osmium concentration of the star polymer is less than about 200 ppm. In certain embodiments, the osmium concentration of the star polymer is less than about 150 ppm. In certain embodiments, the osmium concentration of the star polymer is less than about 100 ppm. In certain embodiments, the osmium concentration of the star polymer is less than about 50 ppm. In certain embodiments, the osmium concentration of the star polymer is below the detectable limit measurable by inductively coupled plasma mass spectrometry (ICP-MS).

In certain embodiments, the transition metal is molybdenum. In certain embodiments, the molybdenum concentration of the star polymer is less than about 450 ppm. In certain embodiments, the molybdenum concentration of the star polymer is less than about 400 ppm. In certain embodiments, the molybdenum concentration of the star polymer is less than about 350 ppm. In certain embodiments, the molybdenum concentration of the star polymer is less than about 300 ppm. In certain embodiments, the molybdenum concentration of the star polymer is less than about 250 ppm. In certain embodiments, the molybdenum concentration of the star polymer is less than about 200 ppm. In certain embodiments, the molybdenum concentration of the star polymer is less than about 150 ppm. In certain embodiments, the molybdenum concentration of the star polymer is less than about 100 ppm. In certain embodiments, the molybdenum concentration of the star polymer is less than about 50 ppm. In certain embodiments, the molybdenum concentration of the star polymer is below the detectable limit measurable by inductively coupled plasma mass spectrometry (ICP-MS).

In certain embodiments, the transition metal is tungsten. In certain embodiments, the tungsten concentration of the star polymer is less than about 450 ppm. In certain embodiments, the tungsten concentration of the star polymer is less than about 400 ppm. In certain embodiments, the tungsten concentration of the star polymer is less than about 350 ppm. In certain embodiments, the tungsten concentration of the star polymer is less than about 300 ppm. In certain embodiments, the tungsten concentration of the star polymer is less than about 250 ppm. In certain embodiments, the tungsten concentration of the star polymer is less than about 200 ppm. In certain embodiments, the tungsten concentration of the star polymer is less than about 150 ppm. In certain embodiments, the tungsten concentration of the star polymer is less than about 100 ppm. In certain embodiments, the tungsten concentration of the star polymer is less than about 50 ppm. In certain embodiments, the tungsten concentration of the star polymer is below the detectable limit measurable by inductively coupled plasma mass spectrometry (ICP-MS).

In certain embodiments, the transition metal is cobalt. In certain embodiments, the cobalt concentration of the star polymer is less than about 450 ppm. In certain embodiments, the cobalt concentration of the star polymer is less than about 400 ppm. In certain embodiments, the cobalt concentration of the star polymer is less than about 350 ppm. In certain embodiments, the cobalt concentration of the star polymer is less than about 300 ppm. In certain embodiments, the cobalt concentration of the star polymer is less than about 250 ppm. In certain embodiments, the cobalt concentration of the star polymer is less than about 200 ppm. In certain embodiments, the cobalt concentration of the star polymer is less than about 150 ppm. In certain embodiments, the cobalt concentration of the star polymer is less than about 100 ppm. In certain embodiments, the cobalt concentration of the star polymer is less than about 50 ppm. In certain embodiments, the cobalt concentration of the star polymer is below the detectable limit measurable by inductively coupled plasma mass spectrometry (ICP-MS).

In certain embodiments, the transition metal is vanadium. In certain embodiments, the vanadium concentration of the star polymer is less than about 450 ppm. In certain embodiments, the vanadium concentration of the star polymer is less than about 400 ppm. In certain embodiments, the vanadium concentration of the star polymer is less than about 350 ppm. In certain embodiments, the vanadium concentration of the star polymer is less than about 300 ppm. In certain embodiments, the vanadium concentration of the star polymer is less than about 250 ppm. In certain embodiments, the vanadium concentration of the star polymer is less than about 200 ppm. In certain embodiments, the vanadium concentration of the star polymer is less than about 150 ppm. In certain embodiments, the vanadium concentration of the star polymer is less than about 100 ppm. In certain embodiments, the vanadium concentration of the star polymer is less than about 50 ppm. In certain embodiments, the vanadium concentration of the star polymer is below the detectable limit measurable by inductively coupled plasma mass spectrometry (ICP-MS).

In certain embodiments, the star polymer comprises a polymeric core of repeating units covalently linked to backbone polymeric arms of repeating units each covalently linked to polymeric sidechains. In certain embodiments, the star polymer contains one type of polymeric sidechain. In certain embodiments, the star polymer contains different types of polymeric sidechains. In certain embodiments, the polymeric sidechains can be a natural or synthetic polymer. In certain embodiments, the polymeric sidechains are each independently selected from the group consisting of polyethers, polyesters, polyacrylamides, polycarbonates, polysiloxanes, polyfluorocarbons, polysulfones, and polystyrenes.

In certain embodiments, the star polymer contains one type of polymeric sidechain. In certain embodiments, the star polymer contains two types of polymeric sidechains. In certain embodiments, the star polymer contains three types of polymeric sidechains. In certain embodiments, the star polymer contains four types of polymeric sidechains. In certain embodiments, the star polymer contains five types of polymeric sidechains. In certain embodiments, the star polymer contains six types of polymeric sidechains. In certain embodiments, the star polymer contains seven types of polymeric sidechains. In certain embodiments, the star polymer contains eight types of polymeric sidechains. In certain embodiments, the star polymer contains nine types of polymeric sidechains. In certain embodiments, the star polymer contains ten types of polymeric sidechains.

In certain embodiments, the polymeric sidechain is a polyether sidechain. In certain embodiments, the polyether sidechains are selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline). In certain embodiments, the polyether sidechains are polyethylene glycol (PEG). In certain embodiments, the polyethylene glycol sidechains have a molecular weight ranging from about 200 g/mol to about 6000 g/mol. In certain embodiments, the polyethylene glycol sidechains have a molecular weight about 200 g/mol. In certain embodiments, the polyethylene glycol sidechains have a molecular weight about 500 g/mol. In certain embodiments, the polyethylene glycol sidechains have a molecular weight about 1000 g/mol. In certain embodiments, the polyethylene glycol sidechains have a molecular weight about 1500 g/mol. In certain embodiments, the polyethylene glycol sidechains have a molecular weight about 2000 g/mol. In certain embodiments, the polyethylene glycol sidechains have a molecular weight about 2500 g/mol. In certain embodiments, the polyethylene glycol sidechains have a molecular weight about 3000 g/mol. In certain embodiments, the polyethylene glycol sidechains have a molecular weight about 3500 g/mol. In certain embodiments, the polyethylene glycol sidechains have a molecular weight about 4000 g/mol. In certain embodiments, the polyethylene glycol sidechains have a molecular weight about 4500 g/mol. In certain embodiments, the polyethylene glycol sidechains have a molecular weight about 5000 g/mol. In certain embodiments, the polyethylene glycol sidechains have a molecular weight about 5500 g/mol. In certain embodiments, the polyethylene glycol sidechains have a molecular weight about 6000 g/mol.

In certain embodiments, the polymeric sidechain is a polyester sidechain. In certain embodiments, the polyester sidechains are selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutryate (PHB), polyethylene adipate (PEA), polybutylene succinate (PBS), and poly(3-hydroxybutyrate-co-3-hydroxyvalerate) (PHBV).

In certain embodiments, the polymeric sidechain is a polyacrylamide sidechain. In certain embodiments, the polyacrylamide sidechains are poly(N-alkylacrylamide) sidechains.

In certain embodiments, the polymeric sidechain is a polycarbonate sidechain. In certain embodiments, the polycarbonate sidechains are selected from the group consisting of poly(bisphenol A carbonate), poly[bisphenol A carbonate-co-4,4'-(3,3,5-trimethylcyclohexylidene)diphenol carbonate], and poly(propylene carbonate).

In certain embodiments, the polymeric sidechain is a polysiloxane sidechain. In certain embodiments, the polysiloxane sidechain is of the formula:

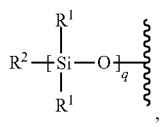

wherein:

$R^1$ is optionally substituted alkyl, optionally substituted alkenyl, optionally substituted aryl, or optionally substituted alkoxy;

$R^2$ is optionally substituted alkyl, optionally substituted alkenyl, optionally substituted aryl, or optionally substituted alkoxy; and q is an integer between 1 and 1000, inclusive.

In certain embodiments, $R^1$ is optionally substituted alkyl. In certain embodiments, $R^2$ is optionally substituted alkyl. In certain embodiments, q is an integer between 1 and 100, inclusive. In certain embodiments, the polysiloxane is polydimethylsiloxane (PDMS). In certain embodiments, the polydimethylsiloxane sidechains have a molecular weight ranging from about 200 g/mol to about 6000 g/mol. In certain embodiments, the polydimethylsiloxane sidechains have a molecular weight about 200 g/mol. In certain embodiments, the polydimethylsiloxane sidechains have a molecular weight about 500 g/mol. In certain embodiments, the polydimethylsiloxane sidechains have a molecular weight about 1000 g/mol. In certain embodiments, the polydimethylsiloxane sidechains have a molecular weight about 1500 g/mol. In certain embodiments, the polydimethylsiloxane sidechains have a molecular weight about 2000 g/mol. In certain embodiments, the polydimethylsiloxane sidechains have a molecular weight about 2500 g/mol. In certain embodiments, the polydimethylsiloxane sidechains have a molecular weight about 3000 g/mol. In certain embodiments, the polydimethylsiloxane sidechains have a molecular weight about 3500 g/mol. In certain embodiments, the polydimethylsiloxane sidechains have a molecular weight about 4000 g/mol. In certain embodiments, the polydimethylsiloxane sidechains have a molecular weight about 4500 g/mol. In certain embodiments, the polydimethylsiloxane sidechains have a molecular weight about 5000 g/mol. In certain embodiments, the polydimethylsiloxane sidechains have a molecular weight about 5500 g/mol. In certain embodiments, the polydimethylsiloxane sidechains have a molecular weight about 6000 g/mol.

In certain embodiments, the polymeric sidechain is a polyfluorocarbon sidechain. In certain embodiments, the polyfluorocarbon sidechains are selected from the group consisting of poly(chlorotrifluoroethylene), poly(ethylene-co-tetrafluoroethylene), poly(tetrafluoroethylene), poly(tetrafluoroethylene-co-perfluoro(propylvinyl ether)), poly(vinylidene fluoride), and poly(vinylidene fluoride-co-hexafluoropropylene).

In certain embodiments, the polymeric sidechain is a polysulfone sidechain. In certain embodiments, the polysulfone sidechains are selected from the group consisting of poly[1-[4-(3-carboxy-4-hydroxyphenylazo)benzenesulfonamido]-1,2-ethanediyl, sodium salt], poly(1-hexadecenesulfone), poly(oxy-1,4-phenylenesulfonyl-1,4-phenylene), poly(oxy-1,4-phenylenesulfonyl-1,4-phenylene), and polyphenylsulfone.

In certain embodiments, the polymeric sidechain is a polystyrene sidechain. In certain embodiments, the polystyrene sidechain is polystyrene (PS). In certain embodiments, the polystyrene sidechains have a molecular weight ranging from about 200 g/mol to about 6000 g/mol. In certain embodiments, the polystyrene sidechains have a molecular weight about 200 g/mol. In certain embodiments, the polystyrene sidechains have a molecular weight about 500 g/mol. In certain embodiments, the polystyrene sidechains have a molecular weight about 1000 g/mol. In certain embodiments, the polystyrene sidechains have a molecular weight about 1500 g/mol. In certain embodiments, the polystyrene sidechains have a molecular weight about 2000 g/mol. In certain embodiments, the polystyrene sidechains have a molecular weight about 2500 g/mol. In certain embodiments, the polystyrene sidechains have a molecular weight about 3000 g/mol. In certain embodiments, the polystyrene sidechains have a molecular weight about 3500 g/mol. In certain embodiments, the polystyrene sidechains have a molecular weight about 4000 g/mol. In certain embodiments, the polystyrene sidechains have a molecular weight about 4500 g/mol. In certain embodiments, the polystyrene sidechains have a molecular weight about 5000 g/mol. In certain embodiments, the polystyrene sidechains have a molecular weight about 5500 g/mol. In certain embodiments, the polystyrene sidechains have a molecular weight about 6000 g/mol.

In certain embodiments, the backbone polymeric arms of Formula (I-b):

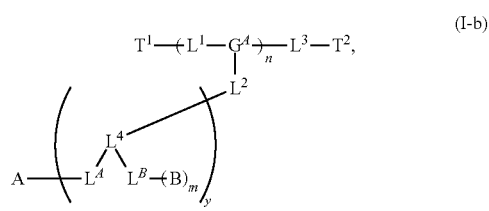

or a salt thereof, wherein:

$G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;

each of $L^1$, $L^2$, $L^3$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$ and $T^2$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio, a structure of Formula (I), and a bond to the polymeric core as described herein;

n is an integer between 5 and 10000, inclusive;

y is an integer between 1 and 20, inclusive;

A is a polymeric sidechain having a number average molecular weight of about 1000 Da to about 100000 Da, and selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio;

each B independently is hydrogen, an agent as described herein, or a polymeric sidechain having a number average molecular weight of about 1000 Da to about 100000 Da; and m is an integer between 2 and 10, inclusive.

In certain embodiments, the backbone polymeric arms are of Formula (I-ab):

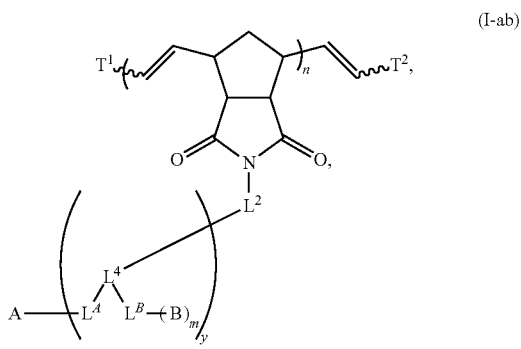

(I-ab)

or a salt thereof.

In certain embodiments, the backbone polymeric arms are of Formula (I):

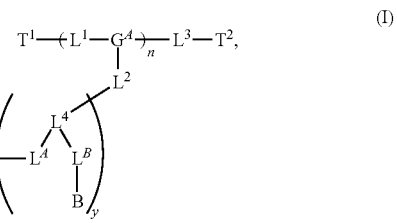

(I)

or a salt thereof, wherein:

$G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;

each of $L^1$, $L^2$, $L^3$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$ and $T^2$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio, a structure of Formula (I), or a bond to the polymeric core as described herein;

n is an integer between 5 and 10000, inclusive;

y is an integer between 1 and 20, inclusive;

A is a polymeric sidechain having a number average molecular weight of about 1000 Da to about 100000 Da, and is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio; and B is hydrogen, an agent as described herein, or a polymeric sidechain having a number average molecular weight of about 1000 Da to about 100000 Da. In certain embodiments, y is 1. In certain embodiments, y is an integer between 2 and 20, inclusive. In certain embodiments, $G^A$ is optionally substituted carbocyclylene, optionally substituted heterocyclylene, or a combination thereof. In certain embodiments, each of $L^1$ and $L^3$ is optionally substituted alkenylene.

In certain embodiments, the backbone polymeric arm is of Formula (I-a):

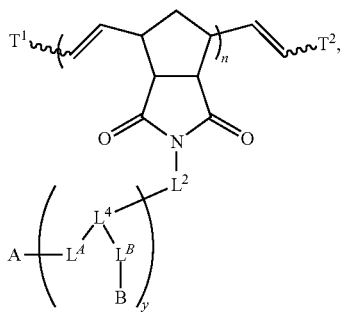

(I-a)

or a salt thereof. In certain embodiments, $L^2$ is optionally substituted alkylene or optionally substituted heteroalkylene. In certain embodiments, $L^A$ is optionally substituted alkylene, optionally substituted heteroalkylene, optionally substituted heteroarylene, or optionally substituted heteroarylalkylene. In certain embodiments, $L^B$ is optionally substituted alkylene, optionally substituted heteroalkylene, optionally substituted heteroarylene, or optionally substituted heteroarylalkylene. In certain embodiments, $L^2$ is optionally substituted heteroalkylene; $L^A$ is optionally substituted heteroarylalkylene; and $L^B$ is optionally substituted heteroalkylene. In certain embodiments, $L^4$ is of formula:

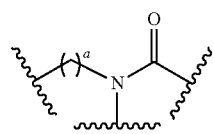

wherein: a is an integer between 1 and 100, inclusive. In certain embodiments, $L^4$ is of formula:

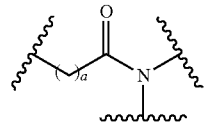

wherein: a is an integer between 1 and 100, inclusive. In certain embodiments, n is an integer between 10 and 1000, inclusive. In certain embodiments, n is an integer between 10 and 100, inclusive. In certain embodiments, n is an integer between 20 and 60, inclusive. In certain embodiments, each of $T^1$ and $T^2$ is independently hydrogen, optionally substituted aryl, a structure of Formula (I), or a bond to the polymeric core as described herein. In certain embodiments, B is a hydrogen. In certain embodiments, B is an agent selected from the group consisting of a pharmaceutical agent (e.g., a therapeutic agent, a diagnostic agent, or a prophylactic agent), drug, protein, polynucleotide, imaging agent, biopolymer, polymer, small molecule, large molecule, amino acid, polysaccharide, or lipid.

In certain embodiments, the backbone polymeric arm is of formula:

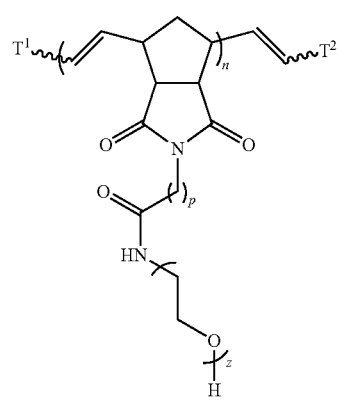

wherein:
p is an integer between 1 and 10, inclusive;
n is an integer between 5 and 10000, inclusive; and
z is an integer between 1 and 100, inclusive.

In certain embodiments, the backbone polymeric arm is of formula:

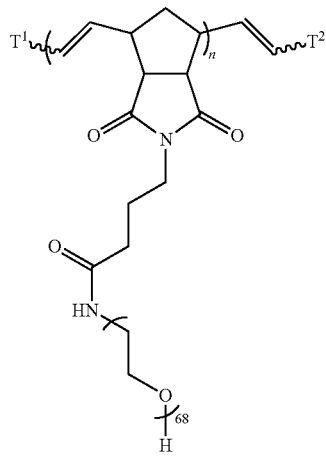

wherein n is an integer between 5 and 10000, inclusive.

In certain embodiments, the backbone polymeric arm is of formula:

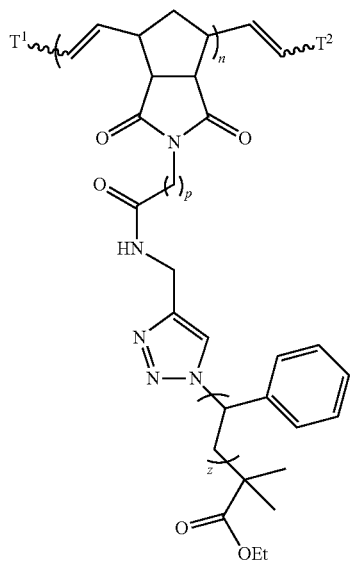

wherein:
  p is an integer between 1 and 10, inclusive;
  n is an integer between 5 and 10000, inclusive; and
  z is an integer between 1 and 100, inclusive.

In certain embodiments, the backbone polymeric arm is of formula:

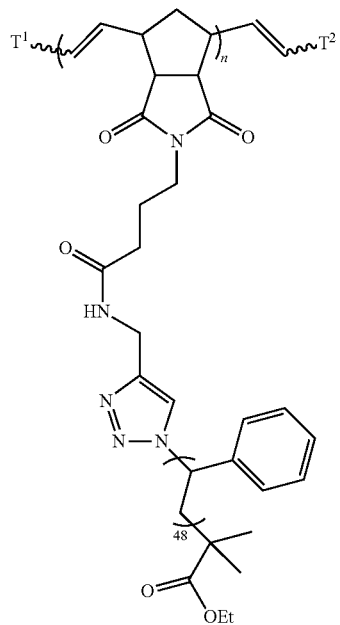

wherein n is an integer between 5 and 10000, inclusive.

In certain embodiments, the backbone polymeric arm is of formula:

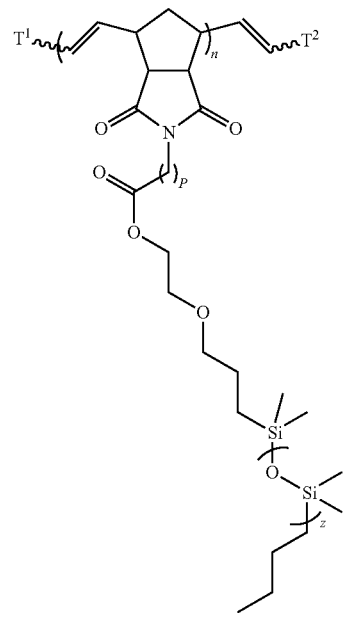

wherein:
  p is an integer between 1 and 10, inclusive;
  n is an integer between 5 and 10000, inclusive; and
  z is an integer between 1 and 100, inclusive.

In certain embodiments, the backbone polymeric arm is of formula:

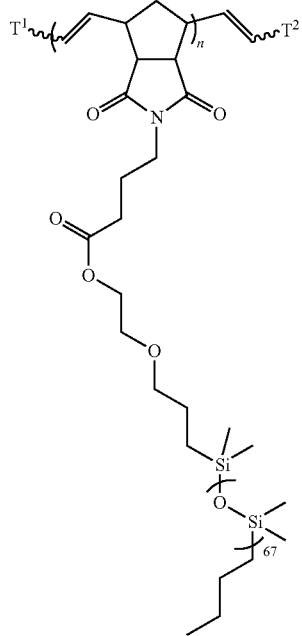

wherein n is an integer between 5 and 10000, inclusive.

In certain embodiments, the polymeric core is of Formula (II):

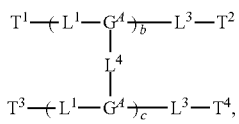

(II)

or a salt thereof, wherein:

$G^4$ is optionally substituted alkylene, optionally substituted heteroalkylene, optionally substituted carbocyclylene, optionally substituted heterocyclylene, optionally substituted arylene, optionally substituted heteroarylene, or a combination thereof;

each of $L^1$, $L^3$, and $L^4$, is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

each of $T^1$, $T^2$, $T^3$, and $T^4$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thio, a structure of Formula (I), or a structure of Formula (II); and b and c are independently an integer between 1 and 10000, inclusive. In certain embodiments, each of $T^1$, $T^2$, $T^3$ and $T^4$ is independently a structure of Formula (I) or a structure of Formula (II).

In certain embodiments, the polymer core is of formula:

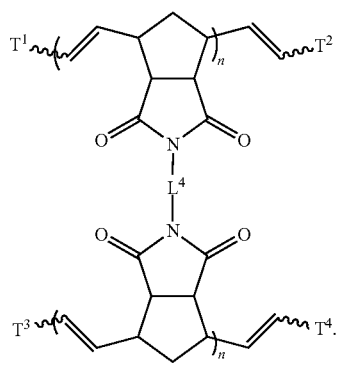

In certain embodiments, each instance of n can be independently an integer between 1 and 10000, inclusive.

In certain embodiments, the polymeric core is of formula:

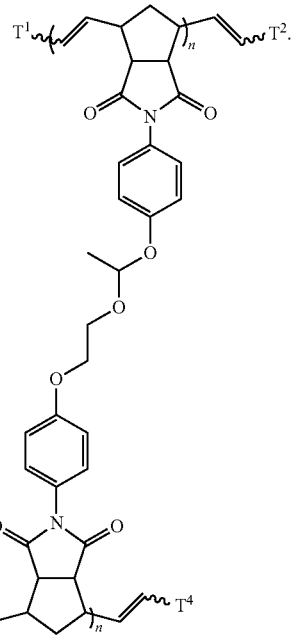

In certain embodiments, each instance of n can be independently an integer between 1 and 10000, inclusive.

In certain embodiments, at least one backbone polymeric arm contains B, wherein B is an agent selected from the group consisting of a pharmaceutical agent (e.g., a therapeutic agent, a diagnostic agent, or a prophylactic agent), drug, protein, polynucleotide, imaging agent, biopolymer, polymer, small molecule, large molecule, amino acid, polysaccharide, or lipid. In certain embodiments, B is a small molecule, wherein the small molecule is a boronic acid.

In certain embodiments, an agent is a pharmaceutical agent (e.g., a therapeutic agent, a diagnostic agent, or a prophylactic agent), diagnostic agent, prophylactic agent, drug, protein, peptide, polynucleotide, imaging agent, biopolymer, polymer, small molecule, large molecule, amino acid, polysaccharide, or lipid.

In certain embodiments, the agent is a pharmaceutical agent. In certain embodiments the pharmaceutical agent is a therapeutic agent, a diagnostic agent, or a prophylactic agent. In certain embodiments, the therapeutic agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is paclitaxel.

In certain embodiments, the agent is an anti-hypertension agent. Exemplary anti-hypertension agents include, but are not limited to, amiloride, amlodipine, atenolol, azilsartan, benazepril, bendroflumethiazide, betaxolol, bisoprolol, bucindolol, bumetanide, candesartan, captopril, carteolol, carvedilol, chlorothiazide, chlorthalidone, cilnidipine, clevidipine, diltiazem, doxazosin, enalapril, epitizide, eplerenone, eprosartan, ethacrynic acid, felodipine, Fimasartan, fosinopril, furosemide, hydrochlorothiazide, indapamide, indoramin, irbesartan, isradipine, labetalol, lercanidipine, levamlodipine, lisinopril, losartan, methyclothiazide, metolazone, metoprolol, moexipril, nadolol, nebivolol, nicardipine, nifedipine, nimodipine, nisoldipine, nitrendipine, olmesartan, oxprenolol, penbutolol, perindopril, pindolol, phenoxybenzamine, phentolamine, polythiazide, prazosin, propranolol, quinapril, ramipril, spironolactone, telmisartan, terazosin, timolol, tolazoline, torsemide, trandolapril, triamterene, valsartan, and verapamil. In certain embodiments, the anti-hypertension agent is telmisartan.

Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents, such as magnetic-resonance signal enhancing agents, X-ray attentuatung agents, ultrasound scattering agent, and ultrasound frequency shifting agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent. In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}$Cu diacetyl-bis(N$^4$-methylthiosemicarbazone) ($^{64}$Cu-ASTM), $^{18}$F-fluorodeoxyglucose (FDG), $^{18}$F-fluoride, 3'-deoxy-3'-$^{18}$F-fluorothymidine (FLT), $^{18}$F-fluoromisonidazole (FMISO), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent is a radical-containing compound. In certain embodiments, the imaging agent is a nitroxide radical-containing compound. In certain embodiments, the imaging agent or diagnostic agent is of the formula:

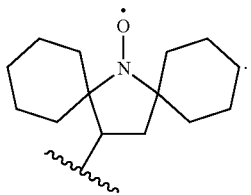 [SMILES: *C1CC2(CCCCC2)N(O)C12CCCCC2]

In certain embodiments, the imaging agent or diagnostic agent is an organic compound. In certain embodiments, the imaging agent is a salt of an organic compound. In certain embodiments, the imaging agent or diagnostic agent is of the formula:

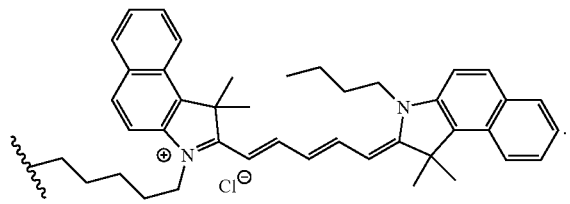 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-]]

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent). Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopoes $^{18}$F, $^{15}$O, $^{13}$N, $^{11}$C, $^{82}$Rb, $^{64}$Cu, and $^{68}$Ga, e.g., fludeoxyglucose ($^{18}$F-FDG), $^{68}$Ga-DOTA-psuedopeptides (e.g., $^{68}$Ga-DOTA-TOC), $^{11}$C-metomidate, $^{11}$C-acetate, $^{11}$C-methionine, $^{11}$C-choline, $^{18}$F-fluciclovine, $^{18}$F-fluorocholine, $^{18}$F-fluorodeoxysorbitol, $^{18}$F-3'-fluoro-3'-deoxythymidine, $^{11}$C-raclopride, and $^{18}$F-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X-SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present disclosure include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F.

Prophylactic agents that can be included in the conjugates of the disclosure include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

Methods for Preparing Brush-Arm Star Polymers (BASPs)

Another aspect of the present disclosure relates to methods of preparing a star polymer comprising forming a star polymer via polymerization reactions and a step to remove the metal complex performing the polymerization reaction. In certain embodiments, the methods are utilized to prepare ROMP-in BASPs. In certain embodiments, the methods are utilized to prepare ROMP-out BASPs. In certain embodiments, the methods are utilized to prepare BASP gels. In certain embodiments, the polymerization reactions are olefin metathesis polymerization reactions. In certain embodiments, the polymerization reactions are ring-opening metathesis polymerization (ROMP).

In general, the methods of preparing a star polymer comprise the step of forming the star polymer via polymerization reactions. In certain embodiments, the method further comprises the step of purifying the star polymer via addition of an additive, dialysis, and/or lyophilization to produce a BASP with a metal concentration less than about 450 ppm.

In certain embodiments, the star polymers are formed from two or more of olefin metathesis polymerization reactions. In certain embodiments, the star polymers are formed form two olefin metathesis polymerization reactions. In certain embodiments, the star polymers are formed form three olefin metathesis polymerization reactions. In certain embodiments, the star polymers are formed form four olefin metathesis polymerization reactions. In certain embodiments, the star polymers are formed form five olefin metathesis polymerization reactions. In certain embodiments, the star polymers are formed form six olefin metathesis polymerization reactions. In certain embodiments, the star polymers are formed form seven olefin metathesis polymerization reactions. In certain embodiments, the star polymers are formed form eight olefin metathesis polymerization reactions. In certain embodiments, the star polymers are formed form nine olefin metathesis polymerization reactions. In certain embodiments, the star polymers are formed form ten olefin metathesis polymerization reactions. In certain embodiments, the olefin metathesis polymerization reaction is a ring-opening metathesis polymerization reaction.

In certain embodiments, the polymerization reaction comprises the steps of: (a) providing a macromonomer comprising one or more polymeric sidechains and one or more reactive moieties; and (b) reacting the macromonomer provided in step (a) under conditions suitable to effect a polymerization reaction and yield a star polymer. In certain embodiments, the reactive moieties are olefins. In certain embodiments, the polymerization reactions comprise reacting the macromonomers in the presence of a metal complex. In certain embodiments, the metal complex is a transition metal complex. In certain embodiments, the transition metal is selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, and meitnerium. In certain embodiments, the transition metal complex is a ruthenium complex. In certain embodiments, the transition metal complex is a molybdenum complex. In certain embodiments, the transition metal complex is a zirconium complex. In certain embodiments, the transition metal complex is selected from the group consisting of ruthenium salts, bis(cyclopentadienyl)dimethylzirconium(IV), dichloro[1,3-bis(2,6-isopropylphenyl)-2-imidazolidinylidene](benzylidene)(tricyclohexylphosphine) ruthenium(II), dichloro[1,3-bis(2-methylphenyl)-2-imidazolidinylidene](benzylidene) (tricyclohexylphosphine)ruthenium(II), dichloro[1,3-bis(2,4,6-trimethylphenyl)-2-imidazolidinylidene][3-(2-pyridinyl)propylidene]ruthenium (II), dichloro(3-methyl-2-butenylidene)bis(tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium (II) (Grubbs II), and dichloro[1,3-bis(2,4,6-trimethylphenyl)-2-imidazolidinylidene](benzylidene)bis(3-bromopyridine)ruthenium(II) (Grubbs III). In certain embodiments, the polymerization initiator is of the formula:

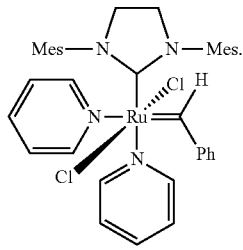

In certain embodiments, the additive allows for the removal of metal byproducts. In certain embodiments, the additive is selected from a group consisting of DMSO, triphenylphosine oxide, lead tetraacetate (Pb(OAc)$_4$), activated carbon, mesoporous silicates, isocyanides, and trishydroxymethylphosphine. In certain embodiments, the additive is trishydroxymethylphosphine. In certain embodiments, the reactions to form BASPs were quenched with an organic compound. In certain embodiments, the organic compound is ethyl vinyl ether. In certain embodiments, the reactions were quenched with a drop of ethyl vinyl ether and then were dialyzed against water for 1 day before lyophilization after addition of trishydroxymethylphosphine and DMSO. After the preparation of BASP gels, the gels were swollen in ethyl vinyl ether, trishydroxymethylphosphine, and water before lyophilization. Ruthenium concentrations were determined by inductively coupled mass spectrometry (ICP-MS) using a calibration curve derived from Grubbs III.

In certain embodiments, the present disclosure describes a method of preparing a ring-opening metathesis polymerization-in brush-arm star polymer (ROMP-in BASP), the method comprising the steps of: (a) providing a macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; and (e) reacting the polymer provided in step (c) and the crosslinker provided in step (d) under conditions suitable to effect a polymerization reaction and yield a ROMP-in BASP. In certain embodiments, the method further comprises the step of purifying the ROMP-in BASP via addition of an additive, dialysis, and/or lyophilization to produce a BASP with a metal concentration less than about 450 ppm.

In certain embodiments, the present disclosure describes a method of preparing a ring-opening metathesis polymerization-out brush-arm star polymer (ROMP-out BASP), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; (e) reacting the polymer provided in step (c) and the crosslinker provided in step (d) under conditions suitable to effect a polymerization reaction and yield a ROMP-in BASP; (f) providing a second macromonomer comprising one or more polymeric sidechains and one or more reactive moieties; and (g) reacting the ROMP-in BASP provided in step (e) and the macromonomer provided in step (f) under conditions suitable to effect a polymerization reaction and yield a ROMP-out BASP. In certain embodiments, the method further comprises the step of purifying the ROMP-out BASP via addition of an additive, dialysis, and/or lyophilization to produce a BASP with a metal concentration less than about 450 ppm.

In certain embodiments, the present disclosure describes a method of preparing a brush-arm star polymer gel (BASP gel), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a first crosslinker comprising one or more reactive moieties; (e) reacting the polymer provided in step (c) and the crosslinker provided in step (d) under conditions suitable to effect a polymerization reaction and yield a ROMP-in BASP; (f)

providing a second macromonomer comprising one or more polymeric sidechains and one or more reactive moieties; (g) reacting the ROMP-in BASP provided in step (e) and the macromonomer provided in step (f) under conditions suitable to effect a polymerization reaction and yield a ROMP-out BASP; (h) providing a second crosslinker comprising one or more reactive moieties; and (i) reacting the ROMP-out BASP provided in step (g) and the crosslinker provided in step (h) under conditions suitable to effect a polymerization reaction and yield a BASP gel. In certain embodiments, the method further comprises the step of purifying the BASP gel via addition of an additive, dialysis, and/or lyophilization to produce a BASP with a metal concentration less than about 450 ppm.

In certain embodiments, the present disclosure describes a method of preparing a surface-functionalized ring-opening metathesis polymerization-out brush-arm star polymer (ROMP-out BASP), the method comprising the steps of: (a) providing a first macromonomer comprising one or more polymeric sidechains and one or more reactive moieties; (b) providing a metal complex; (c) reacting the macromonomer provided in step (a) and the metal complex provided in step (b) under conditions suitable to yield a polymer; (d) providing a crosslinker comprising one or more reactive moieties; (e) reacting the polymer provided in step (c) and the crosslinker provided in step (d) under conditions suitable to effect a polymerization reaction and yield a ROMP-in BASP; (f) providing a second macromonomer comprising one or more polymeric sidechains and one or more reactive moieties; (g) reacting the ROMP-in BASP provided in step (e) and the macromonomer provided in step (f) under conditions suitable to effect a polymerization reaction and yield a ROMP-out BASP; and (h) providing a surface capping reagent comprising one or more reactive moieties; and (i) reacting the ROMP-out BASP with the surface capping reagent in step (h) under conditions suitable to effect a polymerization reaction and yield a surface-functionalized ROMP-out BASP. In certain embodiments, the method further comprises the step of purifying the surface-functionalized ROMP-out BASP via addition of an additive, dialysis, and/or lyophilization to produce a BASP with a metal concentration less than about 450 ppm.

In certain embodiments, the method of preparing a surface-functionalized ROMP-out BASP further comprises a step of performing a nucleophilic substitution reaction. In certain embodiments, surface-functionalized ROMP-out BASP is prepared by reacting a nucleophile with a surface-functionalized ROMP-out BASP containing activated esters or activated carbonates.

In certain embodiments, the nucleophile is selected from the group consisting of halides, Grignard reagents, organolithium reagents, acetylides, enols, enolates, water, hydroxide anion, alkoxide anions, hydrogen peroxide, molecules containing an alcohol group, molecules containing a carboxylate anion, hydrogen sulfide, salts of hydrogen sulfide, thiols, thiolate anions, anions of thiolcarboxylic acids, anions of dithiocarbonates, anions of dithiocarbamates, ammonia, azide, amines, molecules containing an amino group, nitriles, hydroxylamine, hydrazine, carbazide, phenylhydrazine, semicarbazide, and amides. In certain embodiments, the nucleophile is a molecule containing an amino group.

In certain embodiments, the methods of preparing a star polymer include the use of a solvent. In certain embodiments, the solvent used to prepare the star polymer can be polar or non-polar, and/or protic or aprotic. In certain embodiments, the methods of preparing a star polymer include the use of more than one solvent. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahydrofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene. In certain embodiments, the solvent used to prepare the star polymer is tetrahydrofuran. In certain embodiments, the solvent used to prepare the star polymer is dichloromethane.

In certain embodiments, the methods of preparing a star polymer require at least one macromonomer. In certain embodiments, the methods of preparing a star polymer utilize the same macromonomer. In certain embodiments, the methods of preparing a star polymer utilize at least two different macromonomers. In certain embodiments, the methods of preparing a star polymer utilize the macromonomer of Formula (III):

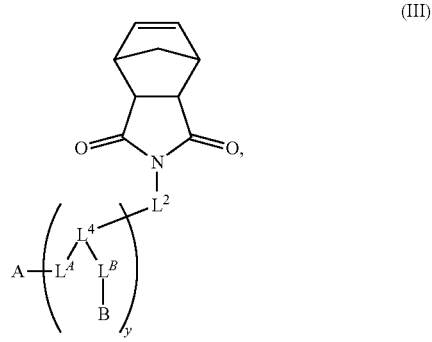

(III)

or a salt thereof, wherein:

each of $L^2$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

y is an integer between 1 and 20, inclusive;

A is a polymeric sidechain having a number average molecular weight of about 1000 Da to about 100000 Da, and selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio; and B is a hydrogen, pharmaceutical agent (e.g., a therapeutic agent, a diagnostic agent, or a prophylactic agent), a drug, a protein, a polynucleotide, an imaging agent, a biopolymer, a polymer, a small molecule, a large molecule, an amino acid, a polysaccharide, a lipid, or a polymeric sidechain having a number average molecular weight of about 1000 Da to about 100000 Da.

In certain embodiments, the methods of preparing a star polymer utilize the macromonomer of Formula (III-b):

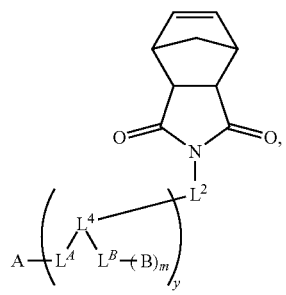

(III-b)

or a salt thereof, wherein:

each of $L^2$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;

y is an integer between 1 and 20, inclusive;

A is a polymeric sidechain having a number average molecular weight of about 1000 Da to about 100000 Da, or selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio;

each B is independently hydrogen, pharmaceutical agent, a drug, a protein, a polynucleotide, an imaging agent, a biopolymer, a polymer, a small molecule, a large molecule, an amino acid, a polysaccharide, a lipid, or polymeric sidechain having a number average molecular weight of about 1000 Da to about 100000 Da; and m is an integer between 2 and 10, inclusive.

In certain embodiments, the methods of preparing a star polymer utilize the macromonomer of formula:

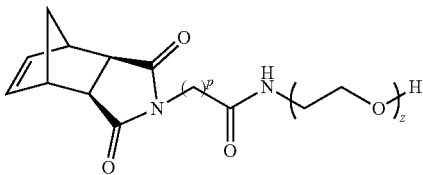

wherein: p is an integer between 1 and 10 inclusive; and z is an integer between 1 and 100, inclusive. In certain embodiments, the methods of preparing a star polymer utilize the macromonomer of formula:

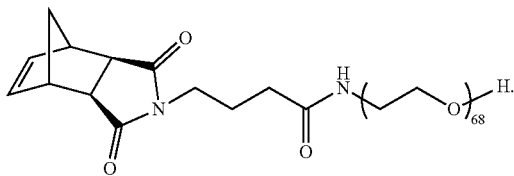

In certain embodiments, the methods of preparing a star polymer utilize the macromonomer of formula:

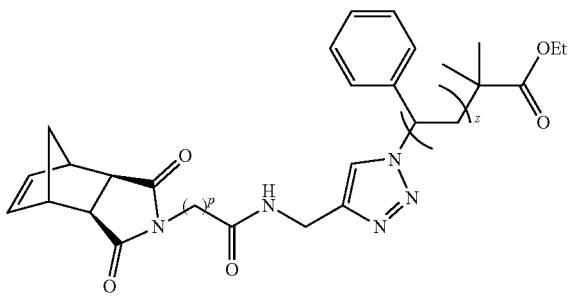

wherein: p is an integer between 1 and 10, inclusive; and z is an integer between 1 and 100, inclusive. In certain embodiments, the methods of preparing a star polymer utilize the macromonomer of formula:

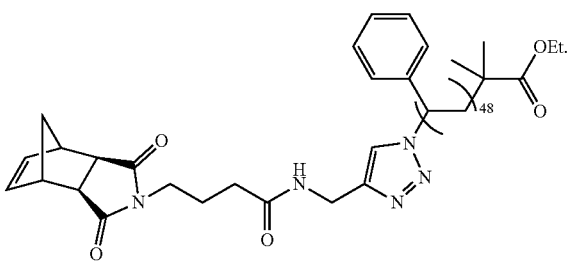

In certain embodiments, the methods of preparing a star polymer utilize the macromonomer of formula:

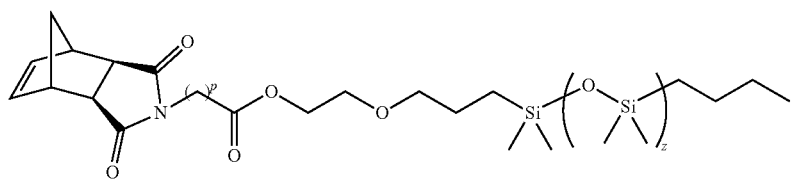

wherein: p is an integer between 1 and 10, inclusive; and z is an integer between 1 and 100, inclusive. In certain embodiments, the methods of preparing a star polymer utilize the macromonomer of formula:

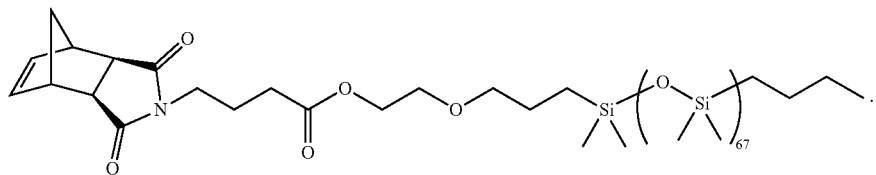

In certain embodiments, the methods of preparing a star polymer require at least one crosslinker. In certain embodiments, the crosslinker is of Formula (IV):

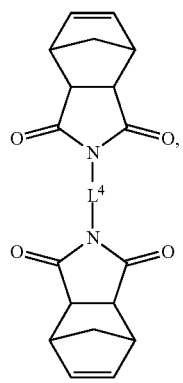 (IV)

or a salt thereof, wherein

L⁴ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof. In certain embodiments, the crosslinker is of formula:

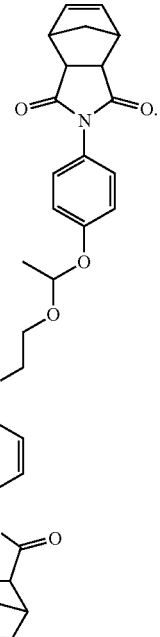

In certain embodiments, the methods of preparing a star polymer require at least one surface capping reagent. In certain embodiments, the surface capping reagent contains an activated ester or activated carbonate. In certain embodiments, the surface capping reagent is of the formula:

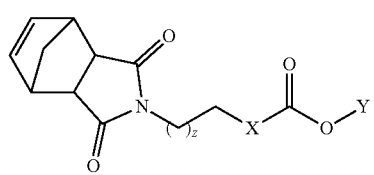

or a salt thereof, wherein: X is $CH_2$, $NR^3$, or O; wherein $R^3$ is hydrogen, optionally substituted alkyl, optionally substituted alkenyl, optionally substituted alkynyl, optionally substituted aryl, optionally substituted heteroaryl, or a nitrogen protecting group; Y is activating group; and z is an integer between 1 and 100, inclusive. In certain embodiments, the surface capping reagent is of the formula:

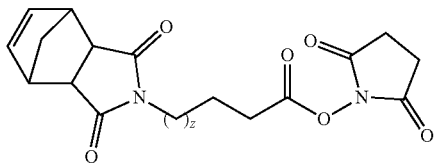

or a salt thereof. In certain embodiments, the surface capping reagent is of the formula:

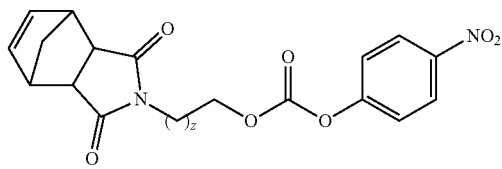

or a salt thereof. In certain embodiments, z is 1. In certain embodiments, z is 2. In certain embodiments, z is 3. In certain embodiments, z is 4. In certain embodiments, z is 5. In certain embodiments, z is 6. In certain embodiments, z is 7. In certain embodiments, z is 8. In certain embodiments, z is 9. In certain embodiments, z is 10. In certain embodiments, z is an integer between 11 and 100, inclusive.

Compositions and Kits

Another aspect of the present disclosure relates to compositions and kits containing a star polymer. In certain embodiments, the present disclosure describes a pharmaceutical composition comprising a star polymer, wherein the metal concentration is less than about 450 ppm, and a pharmaceutically acceptable excipient. In certain embodiments, the present disclosure describes a pharmaceutical composition comprising a therapeutically effective amount of a star polymer. In certain embodiments, the present disclosure describes a kit comprising a star polymer, wherein the metal concentration is less than about 450 ppm, or a composition described herein, and instructions for use.

Compositions described herein can be prepared by any method known in the art. In general, such preparatory methods include bringing the star polymer described herein into association with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Although the descriptions of compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The star polymers and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the polymer or pharmaceutical composition described herein is suitable for topical administration to the eye of a subject.

The exact amount of a polymer required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound or polymer described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The star polymer or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the star polymer or composition described herein in a single dose or administered separately in different doses. The particular combination to employ in a regimen will take into account compatibility of the star combination described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits. The kits provided may comprise a star polymer or pharmaceutical composition described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or star polymer described herein. In some embodiments, the pharmaceutical composition or compound described herein provided in the first container and the second container are combined to form one unit dosage form.

In certain embodiments, the kits are comprised of a star polymer described herein and instructions for use. In certain embodiments, the kits are comprised of a composition described herein and instructions for use. In certain embodiments, a kit described herein further includes instructions for using the kit. A kit described herein may also include information as required by a regulatory agency such as the U.S. Food and Drug Administration (FDA). In certain embodiments, the information included in the kits is prescribing information. A kit described herein may include one or more additional pharmaceutical agents described herein as a separate composition.

Methods of Treatment

Another aspect of the present disclosure relates to methods of treating or preventing a disorder, disease, or condition comprising administering to a subject in need thereof a therapeutically effective amount of a star polymer or a composition described herein. In particular, the star polymers and compostions described herein are useful for in vivo applications because the metal concentration has been reduced to a safe range to be used in a subject.

In certain embodiments, a method of treating or preventing a disorder, disease, or condition comprising administering to a subject in need thereof a therapeutically effective amount of a star polymer or a composition described herein.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In some embodiments, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs).

In certain embodiments, the disorder, disease, or condition is selected from a group consisting of genetic diseases, dermatological conditions, proliferative diseases (e.g., cancer), liver diseases, spleen diseases, gastrointestinal diseases, lung diseases, hematological diseases, neurological diseases, painful conditions, psychiatric disorders, metabolic disorders, cardiovascular diseases, infectious diseases (e.g., bacterial infections, viral infections), and fibrotic conditions.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1: General Procedure for Synthesis of ROMP-Out BASP

Step 1: ROMP-in

To 2×1 mL vials charged with a Teflon-lined white cap was added PEG 3k MM (12.9 mg, 10 equiv). Care was taken to ensure the solid white PEG 3k MM (3244 g/mol) was added to the bottom of the vial and did not stick to the side and/or top of the vial. A stirbar was added to one of the two vials. Another 1 mL vial charged with a Teflon-lined white cap was charged with Acetal XL (35.7 mg; MW=580.6 g/mol). The vials were then brought into a $N_2$ filled glovebox, whereupon anhydrous 1,4-dioxane (65 uL) was added via a micropipetter. Care was taken to ensure the solvent was added directly to the bottom of the vial on top of the white solid rather than down the side of the vial. The vial was capped and stirred gently (100-150 rpm) until the resulting viscous solution was homogenous. The vial can also be gently rolled between ones fingers to help facilitate dissolution of PEG 3k MM. Next, a stock solution of Grubbs III (20 mg/mL in anhydrous 1,4-dioxane) was generated by adding 1,4-dioxane (320 uL) to a 4 mL vial containing Grubbs III (6.4 mg; 726 g/mol). A portion of the dark green Grubbs III stock solution was added to a gently stirred (100-150 ppm) solution of PEG 3k MM (14.4 uL, final concentration PEG 3k MM=0.05 M) via micropipetter; the tip of the pipette was placed below the surface of the viscous reaction medium. The solution immediately turned from colorless to dark green (very briefly after addition of Grubbs III) to brown. The reaction was capped and stirred for 20 min before beginning Step 2. Meanwhile, a stock solution (0.1 M) of Acetal XL was made by dissolving the solid in anhydrous 1,4-dioxane (614 uL). Vortexing is required to fully dissolve Acetal XL, however the solution will eventually become homogenous.

Step 2: Crosslinking

After the reaction time of the first polymerization (Step 1) reached 20 min, the cap of the reaction vial was removed. A 250 uL microsyringe was charged with a solution of Acetal XL (40 uL). The microsyringe was positioned just above the top of the gently stirring (100-150 rpm) reaction medium; one drop was dispensed directly into the reaction every ca. 5-6 sec. Once all of the crosslinker has been added, the reaction vial was capped and stirring continued for ca. 100 min before beginning Step 3. Meanwhile, the second vial of PEG 3k MM was dissolved in anhydrous 1,4-dioxane (40 uL, 0.1 M).

Step 3: ROMP-Out

After the crosslinking step reached ca. 100 min, the next portion of PEG 3k MM solution was added as a single stream via microsyringe (placed below the level of the reaction solution) from a stock solution of MM (at a concentration between 0.05M-0.1M). The density of the MM must be taken into account to track the volume change, which can by measured by observing the volume change of a stock solution. The reaction was allowed to proceed for 1 h, and quenched with a drop or two of ethyl vinyl ether. The quenched reaction mixture was capped and stirred for ca. 15-20 min.

Step 4: Workup and Purification

Before purification, the tip of a pipette was used to remove a small portion of the reaction mixture for GPC and DLS analysis (one pipette for GPC and one pipette for DLS). The pipette was either rinsed with either 0.025 M LiBr in DMF (GPC: 400-500 uL, filtered through 0.45 um PTFE filter) or nanopure milliQ water (DLS: 1 mL) into clean vials. Before dialysis, if scavenging additives are to be added to the reaction, add 250 uL of tetramethylhydroxyphospine (THMP) (M in milliQ $H_2O$) and 250 uL of DMSO to the reaction mixture. If scavenging additives are not going to be used, add 500 uL of milliQ water. Transfer the mixture to regenerated cellulose dialysis tubing (Spectrum Labs, 8 kDa MWCO). Dialyze against milliQ water for 1 d; add fresh water after ca. 1-2 h, after ca. 12 h, and after another ca. 8-10 h. Once the dialysis is complete, transfer the contents of the dialysis tubing into a clean vial and lyophilize for at least 1 d.

Example 2: Surface Functionalization for the Synthesis of ROMP-Out BASP

Perform Step 1 and Step 2 as described in Example 1.

Step 3: ROMP-Out and Capping

After the crosslinking step reached ca. 100 min, the next portion of PEG 3k MM solution was added as a single stream via microsyringe (placed below the level of the reaction solution) from a stock solution of MM (at a concentration between 0.05M-0.1M). The density of the MM must be taken into account to track the volume change, which can by measured by observing the volume change of a stock solution. The reaction was allowed to proceed for 1 h. Nb-PNP (2 equiv, 0.05-0.1 M) was added in 1,4 dioxane and the mixture was stirred for ca. 20 min. The vial was then removed from the glovebox, uncapped, and 2 drops of ethyl vinyl ether were added. The reaction was capped and stirred for ca. 15-20 min. A suitable benzylic amine (i.e. benzyl amine or another benzylic amine with a functionalized aryl ring, 5 equiv) was added in equal volume DMSO. The reaction was stirred for 48 h at r.t. Progress was monitored by measuring the amount of p-nitrophenol in the reaction mixture and quantifying by LC/MS against a standard calibration curve. After completion of the reaction, a drop or two of ethyl vinyl ether are added to quench the reaction. The quenched reaction mixture was capped and stirred for ca. 15-20 min.

Perform Step 4 as described in Example 1.

Discussion

Figure 17:
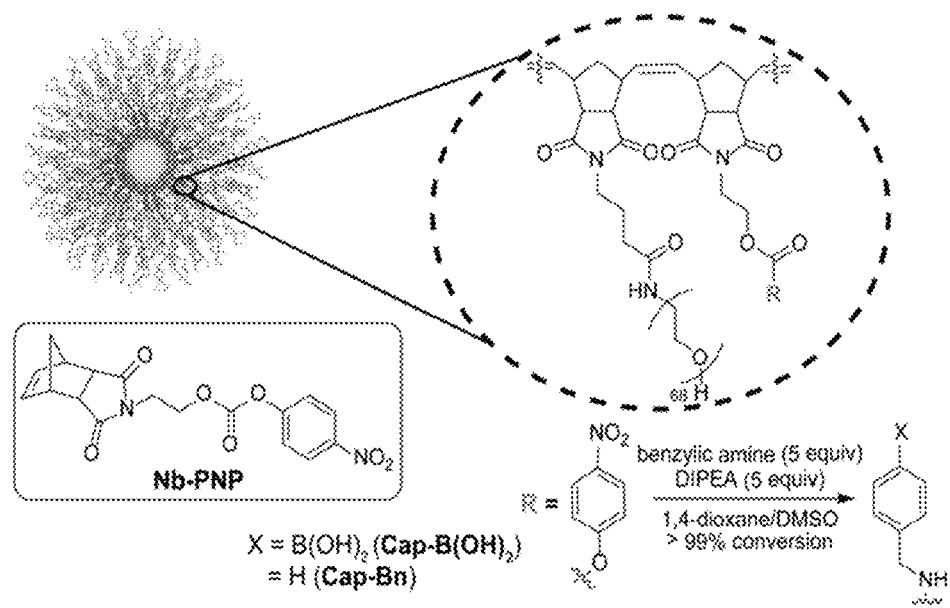
FIG. 17: Functionalization of surface capped BASPs with benzylic amines.
Figure 18A:
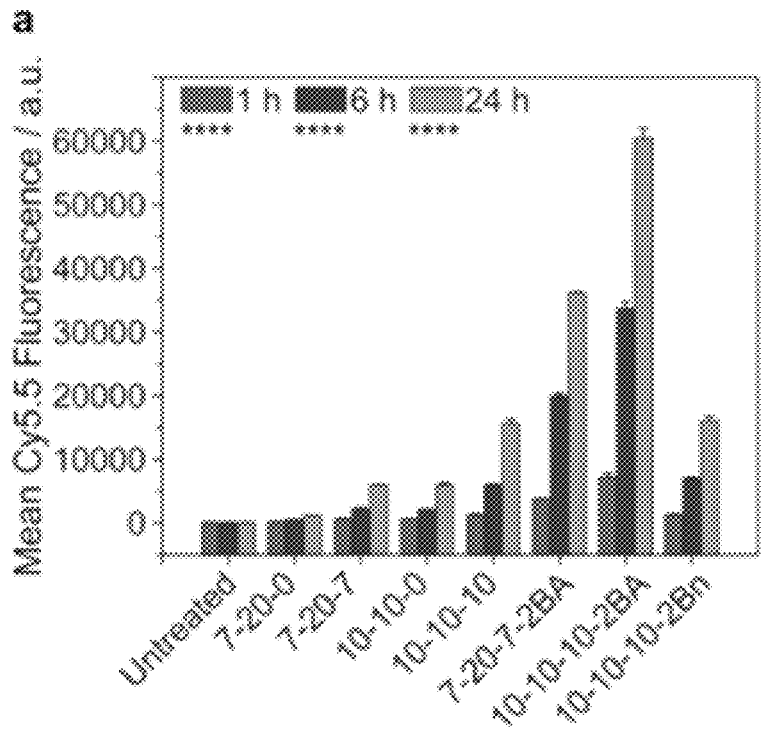
FIGS. 18A to 18E: Statistical analyses of 7-20-7-2BA relative to 7-20-7 and 10-10-10-2BA relative to 10-10-10.
Figure 18B:
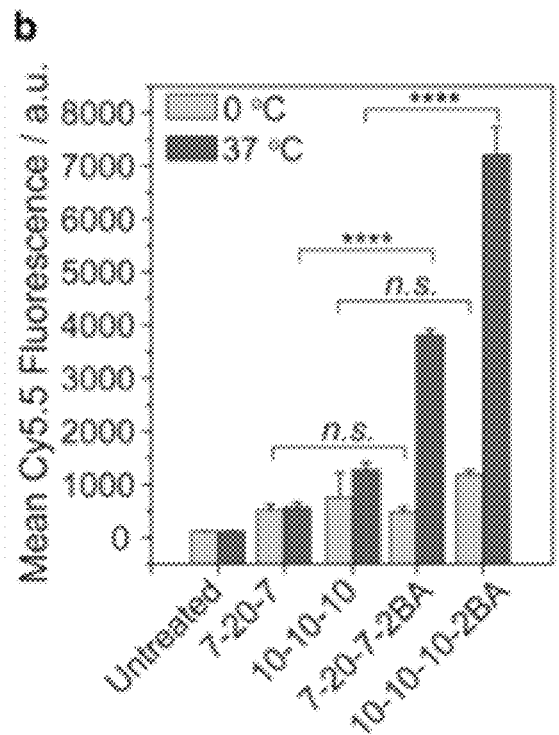
Figure 18C:
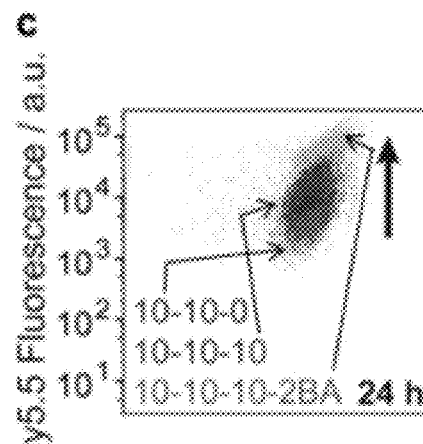
Figure 18D:
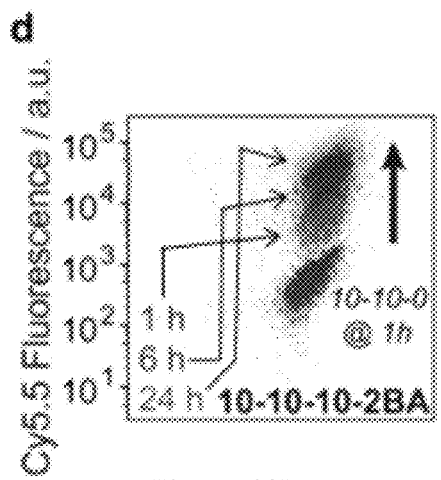
Figure 18E:
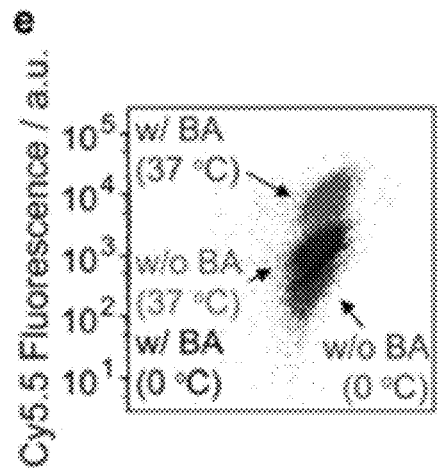

In order to investigate selective BASP uptake by cells, 7-20-X-PNP and/or 10-10-X-PNP BASPs were treated with a suitable nucleophile that could mediate cell uptake (i.e. a targeting ligand) (The notation used in the figures is $m_1$-n-$m_2$, where $m_1$ is equivalents of "ROMP-in" macromonomer relative to the metal complex capable of initiating ROMP (Grubbs III), n is equivalents of crosslinker, and $m_2$ equivalents of "ROMP-out" macromonomer). Prior work from the Kataoka laboratory on nanostructures containing phenyl boronic acids showed their propensity for highly selective sialic acid binding. Sialic acid, the fundamental unit of sialylated glycans, is commonplace on the surface of cancerous tissues. Therefore, BASPs labeled with phenyl boronic acids would be expected to be up-taken more readily than their unlabeled RO-BASP analogs in cancer cells. Nickel-catalyzed Miyura borylation of readily accessible 4-chlorobenzyl(N-Boc-amine) with tetrahydroxydiboron afforded the putative aryl boronic acid, which was deprotected with TFA to afford Cap-B(OH)$_2$ in 34% yield over three steps. Treatment of crude 7-20-7-2PNP and 10-10-10-2PNP with excess Cap-B(OH)$_2$ (5 equiv relative to Nb-PNP used) and DIPEA (5 equiv) in DMSO (equal volume based on reaction mixture volume) afforded boronic acid functionalized BASPs 7-20-7-2BA and 10-10-10-2BA with ≥99% conversion based on p-nitrophenol production measured by HPLC analysis (FIG. 17) within 48 h. To definitively prove that any experimental outcomes are due to the introduction of an aryl boronic acid as opposed to the presence of an aryl carbamate, similar macromolecule 10-10-10-2Bn was made using benzyl amine (Cap-Bn) as the nucleophile. Importantly, in the absence of a benzylic amine nucleophile under otherwise identical reaction conditions, detectable levels of p-nitrophenol were not produced; all p-nitrophenol produced during the reactions arose from introduction of our desired benzylic amine (FIG. 17).

In addition to the functionalized 7-20-7-2BA and 10-10-10-2BA polymers, 7-20-0, 10-10-0, 7-20-7, and 10-10-10 architectures were also synthesized; all polymers incorporated 1 mol % Cy5.5-MM to facilitate in vitro analysis. Importantly, no differences in hydrodynamic diameter ($D_h$) were observed between any of the structures as determined by dynamic light scattering. To begin to assess the effects of BASP architecture on cell uptake, A549 cells were incubated in DMEM (37° C., 5% $CO_2$) with the various polymers for 1 h, 6 h, or 24 h. Subsequent analysis by flow cytometry revealed striking differences in cell uptake at each time point that depended on architecture, stoichiometry, and functionality. In all cases, 10-10-X BASPs were uptaken more readily than 7-20-X BASPs, presumably due to the more hydrophilic nature of the former structures that contain a larger PEG/crosslinker ratio (FIGS. 18A to 18E).

RO-BASPs (i.e. 7-20-7 and 10-10-10) were uptaken more readily than normal BASPs (i.e. 7-20-0 and 10-10-0), again most likely due to increased hydrophilicity in the first set of polymers. Impressively, inclusion of phenyl boronic acids (7-20-7-2BA and 10-10-10-2BA) resulted in up to a 9-fold increase in A549 uptake within 24 h relative to the structural analogs 7-20-7 and 10-10-10. At all times points, 7-20-7-2BA and 10-10-10-2BA were uptaken extremely fast compared to 7-20-7 and 10-10-10, respectively ($P<0.0001$).

Figure 19:
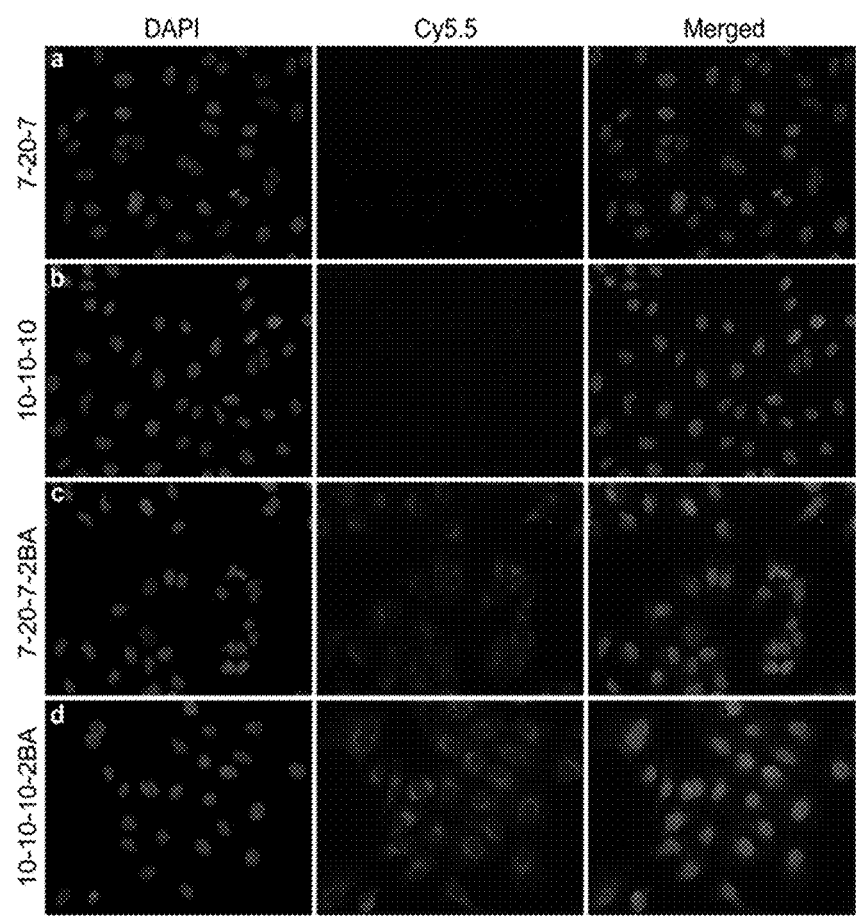
FIG. 19: Fluorescence microscopy images of nuclei (DAPI stained, left), BASP (Cy5.5, middle) and merged DAPI/Cy5.5 (right). For BASPs without boronic acid (BA) tagging (7-20-0 and 10-10-10, i.e. A and B) virtually no Cy5.5 signal is detectable under these imaging conditions. Increasing amounts of Cy5.5 are seen for 7-20-7-2BA and 10-10-10-2BA (C and D). Exposures: 69 ms (DAPI) sand 440 ms (Cy5.5).

Flow cytometry results were also corroborated by fluorescence microscopy (FIG. 19). A549 cells were incubated as described above for 24 h prior to washing and fixing the cells for imaging. Based on the merged DAPI/Cy5.5 images, it is obvious that, under identical imaging conditions, boronic acid labeled BASPs 7-20-7-2BA and 10-10-10-2BA are extremely visible throughout the cytosol while unlabled BASPs 7-20-7 and 10-10-10 are barely detectable. These data also confirm that 7-20-7-2BA and 10-10-10-2BA are not simply non-covalently interacting with cell surface.

While the effects of aryl boronic acids on receptor-mediated cellular uptake in polymers are well studied, this phenomenon required confirmation. To start, there was no significant difference in uptake between 10-10-10 and 10-10-10-2Bn; the presence of functionalized aryl carbamates did not lead to increased uptake over the course of 24 h. Furthermore, active transport of 7-20-7-2BA and 10-10-10-2BA was probed by incubation of all polymers for 1 h at 0° C. Significant differences in uptake were not observed between 7-20-7 and 7-20-7-2BA or 10-10-10 and 10-10-10-2BA at 0° C. On the other hand, statistically significant differences ($P<0.0001$) in uptake were seen for both pairs at 37° C. Compared to uptake levels at 0° C., the increase in uptake for the unfunctionalized polymers at 37° C. was significantly less (ca. 2-3×) than that of the boronic acid-functionalized polymers (ca. 6-7×); decreased rates of active transport (compared to passive transport) at colder temperatures further corroborated our other evidence for receptor-mediated transport of 7-20-7-2BA and 10-10-10-2BA.

Figure 20A:
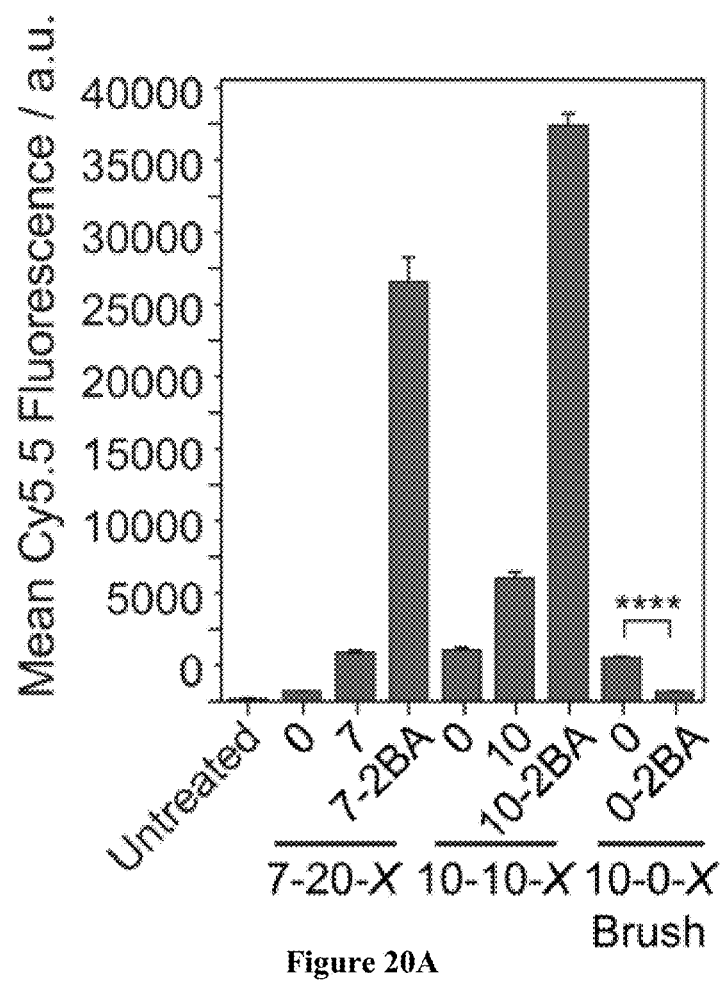
FIGS. 20A to 20C: These data show that the bottlebrushes (10-0-0) (with or without boronic acid tags) are taken up in cells significantly less than the BASPs (with or without boronic acid tags).
Figure 20B:
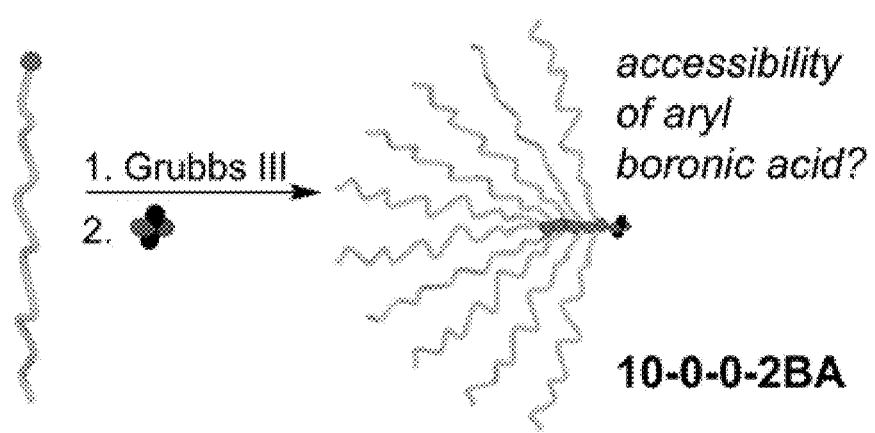
Figure 20C:
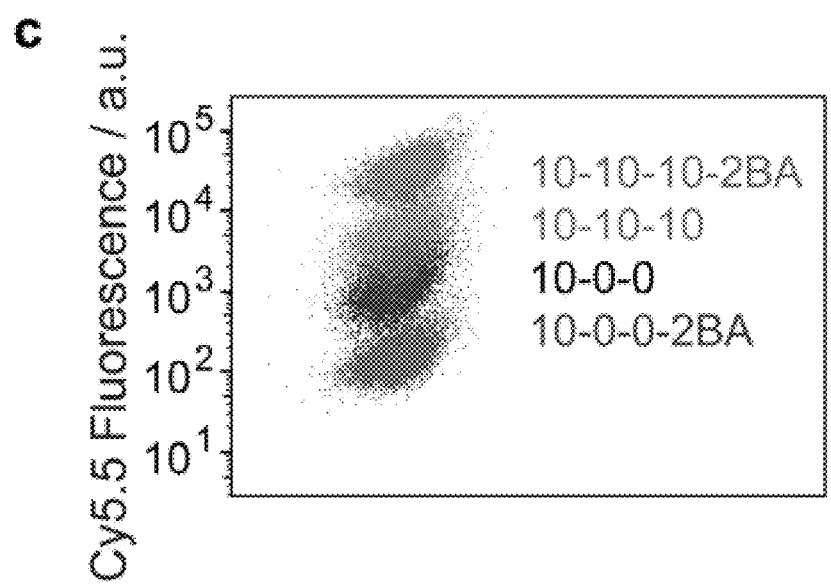

With numerous BASPs in hand, the effects of polymer architecture (i.e. bottlebrush polymer vs. BASP) on cell uptake were investigated. One could imagine functionalizing a bottlebrush with aryl boronic acids in a fashion analogous to the BASP functionalizing described in FIG. 17. Hence, two bottlebrush polymers (m=10) derived from PEG-MM were synthesized, both incorporating 1 mol % Cy5.5-MM: 10-0-0 (i.e. the macroinitiator for all 10-10-X BASPs) and 10-0-0-2BA. After incubating A549 cells with the two bottlebrushes alongside all of the BASP samples, it was discovered that both bottlebrush samples showed minimal uptake; they performed no better than any of the unlabeled BASPs. In fact, 10-0-0-2BA had a significantly lower uptake than its unlabeled counterpart ($P<0.0001$). These findings were quite unexpected; not only did the boronic acid tag not influence uptake, it actually performed worse than when the label was omitted (10-0-0) (FIGS. 20A to 20C). It is surmised that the less dense bottlebrush structure (relative to the denser BASP architecture) allows for the formation of self-assembled structure that not only shields the boronic acid moieties, but also makes the structure less favorable for passive transport across the cell membrane. Counterintuitively, the labels on the end of 10-0-0-2BA are actually less accessible than the labels on 7-20-7-2BA and 10-10-10-2BA, despite all of the potential steric bulk around the boronic acids in the latter examples.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Blencowe, A.; Tan, J. F.; Goh, T. K.; Qiao, G. G. Core Cross-Linked Star Polymers Via Controlled Radical Polymerisation. Polymer 2009, 50 (1), 5-32.

2. Gao, H.; Matyjaszewski, K. Synthesis of Functional Polymers with Controlled Architecture by Crp of Monomers in the Presence of Cross-Linkers: From Stars to Gels. *Prog. Polym. Sci.* 2009, 34 (4), 317.
3. McKenzie, T. G.; Wong, E. H. H.; Fu, Q.; Sulistio, A.; Dunstan, D. E.; Qiao, G. G. Controlled Formation of Star Polymer Nanoparticles Via Visible Light Photopolymerization. ACS Macro Lett. 2015, 4, 1012-1016.
4. Park, S.; Cho, H. Y.; Wegner, K. B.; Burdynska, J.; Magenau, A. J.; Paik, H.-j.; Jurga, S.; Matyjaszewski, K. Star Synthesis Using Macroinitiators Via Electrochemically Mediated Atom Transfer Radical Polymerization. Macromolecules 2013, 46 (15), 5856-5860.
5. Liu, G.; Qiu, Q.; Shen, W.; An, Z. Aqueous Dispersion Polymerization of 2-Methoxyethyl Acrylate for the Synthesis of Biocompatible Nanoparticles Using a Hydrophilic Raft Polymer and a Redox Initiator. Macromolecules 2011, 44 (13), 5237-5245.
6. Qiu, Q.; Liu, G.; An, Z. Efficient and Versatile Synthesis of Star Polymers in Water and Their Use as Emulsifiers. Chem. Commun. 2011, 47 (47), 12685-12687.
7. Zhang, C.; Miao, M.; Cao, X.; An, Z. One-Pot Raft Synthesis of Core Cross-Linked Star Polymers of Polypegma in Water by Sequential Homogeneous and Heterogeneous Polymerizations. Polym. Chem. 2012, 3 (9), 2656-2664.
8. Shi, X.; Miao, M.; An, Z. Core Cross-Linked Star (Ccs) Polymers with Tunable Polarity: Synthesis by Raft Dispersion Polymerization, Self-Assembly and Emulsification. Polym. Chem. 2013, 4 (6), 1950-1959.
9. McKenzie, T. G.; Wong, E. H. H.; Fu, Q.; Lam, S. J.; Dunstan, D. E.; Qiao, G. G. Highly Efficient and Versatile Formation of Biocompatible Star Polymers in Pure Water and Their Stimuli-Responsive Self-Assembly. Macromolecules 2014, 47 (22), 7869-7877.
10. Iha, R. K.; Wooley, K. L.; Nystrom, A. M.; Burke, D. J.; Kade, M. J.; Hawker, C. J. Applications of Orthogonal "Click" Chemistries in the Synthesis of Functional Soft Materials. Chem. Rev. 2009, 109 (11), 5620-5686.
11. Liu, J.; Duong, H.; Whittaker, M. R.; Davis, T. P.; Boyer, C. Synthesis of Functional Core, Star Polymers Via Raft Polymerization for Drug Delivery Applications. Macromol. Rapid Commun. 2012, 33 (9), 760-766.
12. Gao, H. Development of Star Polymers as Unimolecular Containers for Nanomaterials. Macromol. Rapid Commun. 2012, 33 (9), 722-734.
13. Jesberger, M.; Barner, L.; Stenzel, M. H.; Malmström, E.; Davis, T. P.; Barner-Kowollik, C. Hyperbranched Polymers as Scaffolds for Multifunctional Reversible Addition-Fragmentation Chain-Transfer Agents: A Route to Polystyrene-Core-Polyesters and Polystyrene-Block-Poly(Butyl Acrylate)-Core-Polyesters. J. Polym. Sci., Part A: Polym. Chem. 2003, 41 (23), 3847-3861.
14. Kreutzer, G.; Ternat, C.; Nguyen, T. Q.; Plummer, C. J. G.; Manson, J.-A. E.; Castelletto, V.; Hamley, I. W.; Sun, F.; Sheiko, S. S.; Herrmann, A.; et al. Water-Soluble, Unimolecular Containers Based on Amphiphilic Multiarm Star Block Copolymers. Macromolecules 2006, 39 (13), 4507-4516.
15. Hao, X.; Nilsson, C.; Jesberger, M.; Stenzel, M. H.; Malmstrom, E.; Davis, T. P.; O'stmark, E.; Barner-Kowollik, C. Dendrimers as Scaffolds for Multifunctional Reversible Addition-Fragmentation Chain Transfer Agents: Syntheses and Polymerization. J. Polym. Sci., Part A: Polym. Chem. 2004, 42 (23), 5877-5890.
16. Hedrick, J. L.; Trollsis, M.; Hawker, C. J.; Atthoff, B.; Claesson, H.; Heise, A.; Miller, R. D.; Mecerreyes, D.; Jerome, R.; Dubois, P. Dendrimer-Like Star Block and Amphiphilic Copolymers by Combination of Ring Opening and Atom Transfer Radical Polymerization. Macromolecules 1998, 31 (25), 8691-8705.
17. Haddleton, D. M.; Ohno, K. Well-Defined Oligosaccharide-Terminated Polymers from Living Radical Polymerization. Biomacromolecules 2000, 1 (2), 152-156.
18. Stenzel-Rosenbaum, M. H.; Davis, T. P.; Chen, V.; Fane, A. G. Synthesis of Poly(Styrene) Star Polymers Grown from Sucrose, Glucose, and Cyclodextrin Cores Via Living Radical Polymerization Mediated by a Half-Metallocene Iron Carbonyl Complex. Macromolecules 2001, 34 (16), 5433-5438.
19. Angot, S.; Ayres, N.; Bon, S. A. F.; Haddleton, D. M. Living Radical Polymerization Immobilized on Wang Resins: Synthesis and Harvest of Narrow Polydispersity Poly(Methacrylate)S. Macromolecules 2001, 34 (4), 768-774.
20. Barner, L.; Li, C. E.; Hao, X.; Stenzel, M. H.; Barner-Kowollik, C.; Davis, T. P. Synthesis of Core-Shell Poly (Divinylbenzene) Microspheres Via Reversible Addition Fragmentation Chain Transfer Graft Polymerization of Styrene. J. Polym. Sci., Part A: Polym. Chem. 2004, 42 (20), 5067-5076.
21. Muthukrishnan, S.; Plamper, F.; Mori, H.; Müller, A. H. E. Synthesis and Characterization of Glycomethacrylate Hybrid Stars from Silsesquioxane Nanoparticles. Macromolecules 2005, 38 (26), 10631-10642.
22. Gao, H.; Matyjaszewski, K. Synthesis of Star Polymers by a New "Core-First" Method: Sequential Polymerization of Cross-Linker and Monomer. Macromolecules 2008, 41 (4), 1118-1125.
23. Tunca, U.; Ozyurek, Z.; Erdogan, T.; Hizal, G. Novel Miktofunctional Initiator for the Preparation of an Abc-Type Miktoarm Star Polymer Via a Combination of Controlled Polymerization Techniques. J. Polym. Sci., Part A: Polym. Chem. 2004, 42 (17), 4228-4236.
24. Ohno, K.; Wong, B.; Haddleton, D. M. Synthesis of Well-Defined Cyclodextrin-Core Star Polymers. J. Polym. Sci., Part A: Polym. Chem. 2001, 39 (13), 2206-2214.
25. Li, W.; Matyjaszewski, K. Star Polymers Via Cross-Linking Amphiphilic Macroinitiators by Aget Atrp in Aqueous Media. J. Am. Chem. Soc. 2009, 131 (30), 10378-10379.
26. Bapat, A. P.; Ray, J. G.; Savin, D. A.; Hoff, E. A.; Patton, D. L.; Sumerlin, B. S. Dynamic-Covalent Nanostructures Prepared by Diels-Alder Reactions of Styrene-Maleic Anhydride-Derived Copolymers Obtained by One-Step Cascade Block Copolymerization. Polym. Chem. 2012, 3 (11), 3112-3120.
27. Brummelhuis, N. t.; Schlaad, H. Stimuli-Responsive Star Polymers through Thiol-Yne Core Functionalization/Crosslinking of Block Copolymer Micelles. Polym. Chem. 2011, 2 (5), 1180-1184.
28. Mukherjee, S.; Bapat, A. P.; Hill, M. R.; Sumerlin, B. S. Oximes as Reversible Links in Polymer Chemistry: Dynamic Macromolecular Stars. Polym. Chem. 2014, 5 (24), 6923-6931.
29. Zhang, Z. H.; Yin, L. C.; Tu, C. L.; Song, Z. Y.; Zhang, Y. F.; Xu, Y. X.; Tong, R.; Zhou, Q.; Ren, J.; Cheng, J. J. Redox-Responsive, Core Cross-Linked Polyester Micelles. ACS Macro Lett. 2013, 2 (1), 40-44.
30. Bapat, A. P.; Ray, J. G.; Savin, D. A.; Sumerlin, B. S. Redox-Responsive Dynamic-Covalent Assemblies: Stars and Miktoarm Stars. Macromolecules 2013, 46 (6), 2188-2198.

31. Jackson, A. W.; Fulton, D. A. Ph Triggered Self-Assembly of Core Cross-Linked Star Polymers Possessing Thermoresponsive Cores. Chem. Commun. 2011, 47 (24), 6807-6809.
32. Shibata, T.; Kanaoka, S.; Aoshima, S. Quantitative Synthesis of Star-Shaped Poly(Vinyl Ether)S with a Narrow Molecular Weight Distribution by Living Cationic Polymerization. J. Am. Chem. Soc. 2006, 128 (23), 7497-7504.
33. Burdynska, J.; Cho, H. Y.; Mueller, L.; Matyjaszewski, K. Synthesis of Star Polymers Using Arget Atrp. Macromolecules 2010, 43 (22), 9227-9229.
34. Goh, T. K.; Yamashita, S.; Satoh, K.; Blencowe, A.; Kamigaito, M.; Qiao, G. G. Highly Efficient Synthesis of Low Polydispersity Core Cross-Linked Star Polymers by Ru-Catalyzed Living Radical Polymerization. Macromol. Rapid Commun. 2011, 32 (5), 456-461.
35. Wong, E. H. H.; Blencowe, A.; Qiao, G. G. Quantitative Formation of Core Cross-Linked Star Polymers Via a One-Pot Two-Step Single Electron Transfer-Living Radical Polymerization. Polym. Chem. 2013, 4 (17), 4562-4565.
36. Ren, J. M.; Fu, Q.; Blencowe, A.; Qiao, G. G. Organic Catalyst-Mediated Ring-Opening Polymerization for the Highly Efficient Synthesis of Polyester-Based Star Polymers. ACS Macro Lett. 2012, 1 (6), 681-686.
37. Spiniello, M.; Blencowe, A.; Qiao, G. G. Synthesis and Characterization of Fluorescently Labeled Core Cross-Linked Star Polymers. J. Polym. Sci., Part A: Polym. Chem. 2008, 46 (7), 2422-2432.
38. Sulistio, A.; Widjaya, A.; Blencowe, A.; Zhang, X.; Qiao, G. Star Polymers Composed Entirely of Amino Acid Building Blocks: A Route Towards Stereospecific, Biodegradable and Hierarchically Functionalized Stars. Chem. Commun. 2011, 47 (4), 1151-1153.
39. Terashima, T.; Nomura, A.; Ito, M.; Ouchi, M.; Sawamoto, M. Star-Polymer-Catalyzed Living Radical Polymerization: Microgel-Core Reaction Vessel by Tandem Catalyst Interchange. Angew. Chem. 2011, 123 (34), 8038-8041.
40. Helms, B.; Guillaudeu, S. J.; Xie, Y.; McMurdo, M.; Hawker, C. J.; Frechet, J. M. J. One-Pot Reaction Cascades Using Star Polymers with Core-Confined Catalysts. Angew. Chem. 2005, 117 (39), 6542-6545.
41. Schmidt, B. V. K. J.; Rudolph, T.; Hetzer, M.; Ritter, H.; Schacher, F. H.; Barner-Kowollik, C. Supramolecular Three-Armed Star Polymers Via Cyclodextrin Host-Guest Self-Assembly. Polym. Chem. 2012, 3 (11), 3139-3145.
42. Zhang, Q.; Li, G.-Z.; Becer, C. R.; Haddleton, D. M. Cyclodextrin-Centred Star Polymers Synthesized Via a Combination of Thiol-Ene Click and Ring Opening Polymerization. Chem. Commun. 2012, 48 (65), 8063-8065.
43. Bender, J. L.; Corbin, P. S.; Fraser, C. L.; Metcalf, D. H.; Richardson, F. S.; Thomas, E. L.; Urbas, A. M. Site-Isolated Luminescent Europium Complexes with Polyester Macroligands: Metal-Centered Heteroarm Stars and Nanoscale Assemblies with Labile Block Junctions. J. Am. Chem. Soc. 2002, 124 (29), 8526-8527.
44. Altintas, O.; Vogt, A. P.; Barner-Kowollik, C.; Tunca, U. Constructing Star Polymersvia Modular Ligation Strategies. Polym. Chem. 2012, 3 (1), 34-45.
45. Khanna, K.; Varshney, S.; Kakkar, A. Designing Miktoarm Polymers Using a Combination of "Click" Reactions in Sequence with Ring-Opening Polymerization. Macromolecules 2010, 43 (13), 5688-5698.
46. Inglis, A. J.; Pierrat, P.; Muller, T.; Brase, S.; Barner-Kowollik, C. Well-Defined Star Shaped Polymer-Fullerene Hybrids Via Click Chemistry. Soft Matter 2010, 6 (1), 82-84.
47. Dirr, C. J.; Hlalele, L.; Kaiser, A.; Brandau, S.; Barner-Kowollik, C. Mild and Efficient Modular Synthesis of Poly(Acrylonitrile-Co-Butadiene) Block and Miktoarm Star Copolymer Architectures. Macromolecules 2013, 46 (1), 49-62.
48. Gao, H.; Matyjaszewski, K. Modular Approaches to Star and Miktoarm Star Polymers by Atrp of Cross-Linkers. Macromol. Symp. 2010, 291-292 (1), 12-16.
49. Ren, J. M.; Qiao, G. G. Synthetic Strategies Towards Well-Defined Complex Polymeric Architectures through Covalent Chemistry. Chem. Ing. Tech. 2014, 86 (12), 2195-2214.
50. Ren, J. M.; McKenzie, T. G.; Fu, Q.; Wong, E. H. H.; Xu, J.; An, Z.; Shanmugam, S.; Davis; T. P.; Boyer, C.; Qiao; G. G. Star Polymers. Chem. Rev. 2016, 116, 6743-6836.
51. Saunders, R. S.; Cohen, R. E.; Wong, S. J.; Schrock, R. R. Synthesis of Amphiphilic Star Block Copolymers Using Ring-Opening Metathesis Polymerization. Macromolecules 1992, 25 (7), 2055-2057.
52. Nomura, K.; Watanabe, Y.; Fujita, S.; Fujiki, M.; Otani, H. Facile Controlled Synthesis of Soluble Star Shape Polymers by Ring-Opening Metathesis Polymerization (Romp). Macromolecules 2009, 42, 899-901.
53. Otani, H.; Fujita, S.; Watanabe, Y.; Fujiki, M.; Nomura, K. In Olefin Metathesis; Buchmeiser, M. R., Ed.; Wiley-VCH Verlag Gmbh: Weinheim, 2010; Vol. 293.
54. Nomura, K.; Tanaka, K.; Fujita, S. Use of Pyridine-Coated Star-Shaped Romp Polymer as the Supporting Ligand for Ruthenium-Catalyzed Chemoselective Hydrogen Transfer Reduction of Ketones. Organometallics 2012, 31 (14), 5074-5080.
55. Takamizu, K.; Nomura, K. Synthesis of Oligo(Thiophene)-Coated Star-Shaped Romp Polymers: Unique Emission Properties by the Precise Integration of Functionality. J. Am. Chem. Soc. 2012, 134 (18), 7892-7895.
56. Liu, J.; Burts, A. O.; Li, Y. J.; Zhukhovitskiy, A. V.; Ottaviani, M. F.; Turro, N. J.; Johnson, J. A. "Brush-First" Method for the Parallel Synthesis of Photocleavable, Nitroxide-Labeled Poly(Ethylene Glycol) Star Polymers. J. Am. Chem. Soc. 2012, 134 (39), 16337-16344.
57. Burts, A. O.; Gao, A. X.; Johnson, J. A. Brush-First Synthesis of Core-Photodegradable Miktoarm Star Polymers Via Romp: Towards Photoresponsive Self-Assemblies. Macromol. Rapid Commun. 2014, 35 (2), 168-173.
58. Burts, A. O.; Liao, L.; Lu, Y. Y.; Tirrell, D. A.; Johnson, J. A. Brush-First and Click: Efficient Synthesis of Nanoparticles That Degrade and Release Doxorubicin in Response to Light. Photochem. Photobiol. 2014, 90 (2), 380-385.
59. Gao, A. X.; Liao, L. Y.; Johnson, J. A. Synthesis of Acid-Labile Peg and Peg-Doxorubicin-Conjugate Nanoparticles Via Brush-First Romp. ACS Macro Lett. 2014, 3 (9), 854-857.
60. Liao, L.; Liu, J.; Dreaden, E. C.; Morton, S. W.; Shopsowitz, K. E.; Hammond, P. T.; Johnson, J. A. A Convergent Synthetic Platform for Single-Nanoparticle Combination Cancer Therapy: Ratiometric Loading and Controlled Release of Cisplatin, Doxorubicin, and Camptothecin. J. Am. Chem. Soc. 2014, 136 (16), 5896-5899.
61. Dag, A.; Durmaz, H.; Sirkecioglu, O.; Hizal, G.; Tunca, U. Three-Arm Star Ring Opening Metathesis Polymers Via Alkyne-Azide Click Reaction. J. Polym. Sci., Part A: Polym. Chem. 2009, 47 (9), 2344-2351.

What is claimed is:
1. A ring-opening-metathesis-polymerization-out brush-arm star polymer (ROMP-out BASP) formed by a method comprising the steps of:
(a) providing a first macromonomer comprising one or more polymeric sidechains and one or more olefin moieties;
(b) providing a metal complex;
(c) reacting the first macromonomer and the metal complex under conditions suitable to effect ring-opening metathesis polymerization (ROMP) to yield a polymer;
(d) providing a crosslinker, wherein the crosslinker comprises more than one olefin moiety;
(e) reacting the polymer and the crosslinker under conditions suitable to effect ROMP to yield a ring-opening-metathesis-polymerization-in brush-arm star polymer (ROMP-in BASP);
(f) providing a second macromonomer comprising one or more polymeric sidechains and one or more olefin moieties; and
(g) reacting the ROMP-in BASP and the second macromonomer under conditions suitable to effect ROMP to yield a ROMP-out BASP;
provided that the metal concentration of the ROMP-out BASP is less than about 450 ppm by weight.

2. A pharmaceutical composition comprising a ring-opening-metathesis-polymerization-out brush-arm star polymer (ROMP-out BASP) of claim 1, and a pharmaceutically acceptable excipient.

3. A kit comprising a ring-opening-metathesis-polymerization-out brush-arm star polymer of claim 1, and instructions for use.

4. The ROMP-out BASP of claim 1, wherein the metal is ruthenium, and the metal complex is a ruthenium complex.

5. The pharmaceutical composition of claim 2, wherein the ROMP-out BASP comprises one or more therapeutic agents.

6. The ROMP-out BASP of claim 1, wherein the metal complex is dichloro[1,3-bis(2,6-isopropylphenyl)-2-imidazolidinylidene](benzylidene)(tricyclohexylphosphine) ruthenium(II), dichloro[1,3-bis(2-methylphenyl)-2-imidazolidinylidene](benzylidene) (tricyclohexylphosphine)ruthenium(II), dichloro[1,3-bis(2,4,6-trimethylphenyl)-2-imidazolidinylidene][3-(2-pyridinyl)propylidene]ruthenium (II), dichloro(3-methyl-2-butenylidene)bis(tricyclopentylphosphine)ruthenium(II), dichloro[1,3-bis(2-methylphenyl)-2-imidazolidinylidene](2-isopropoxyphenylmethylene)ruthenium(II), dichloro(benzylidene)bis(tricyclohexylphosphine)ruthenium(II), dichloro[1,3-bis(2,4,6-trimethylphenyl)-2-imidazolidinylidene](benzylidene) (tricyclohexylphosphine) ruthenium(II), or dichloro[1,3-bis(2,4,6-trimethylphenyl)-2-imidazolidinylidene](benzylidene)bis(3-bromopyridine)ruthenium(II), or is of the formula:

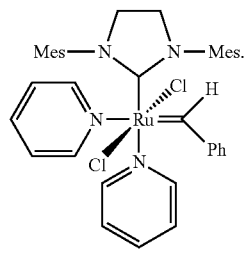

7. The ROMP-out BASP of claim 1, wherein the method further comprises the step of purifying the ROMP-out BASP via addition of an additive, dialysis, and/or lyophilization.

8. The ROMP-out BASP of claim 1, wherein the method further comprises the step of purifying the ROMP-out BASP via addition of an additive, wherein the additive is dimethyl sulfoxide, triphenylphosine oxide, lead tetraacetate, activated carbon, mesoporous silicate, isocyanide, or trishydroxymethylphosphine.

9. The ROMP-out BASP of claim 1, wherein the ROMP-out BASP comprises a polymeric core of repeating units covalently linked to backbone polymeric arms of repeating units each covalently linked to polymeric sidechains.

10. The ROMP-out BASP of claim 9, wherein the polymeric sidechains are each independently selected from polyethers, polyesters, polyacrylamides, polycarbonates, polysiloxanes, polyfluorocarbons, polysulfones, and polystyrenes.

11. The ROMP-out BASP of claim 9, wherein the backbone polymeric arms are of Formula (I):

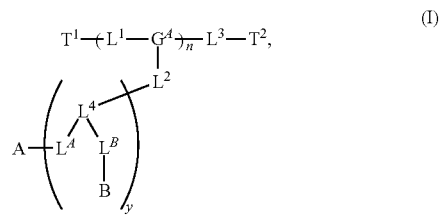

or a salt thereof, wherein:
$G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;
each of $L^1$, $L^2$, $L^3$, $L^4$, $L^A$, and $L^B$ is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;
each of $T^1$ and $T^2$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thiol, a structure of Formula (I), and a bond to the polymeric core;
n is an integer between 5 and 10000, inclusive;
y is an integer between 1 and 20, inclusive;
A is a polymeric sidechain having a number average molecular weight of about 1000 Da to about 100000 Da, and selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thiol; and B is hydrogen, an agent, or a polymeric sidechain having a number average molecular weight of about 1000 Da to about 100000 Da.

12. The ROMP-out BASP of claim 9, wherein the polymeric core is of Formula (II):

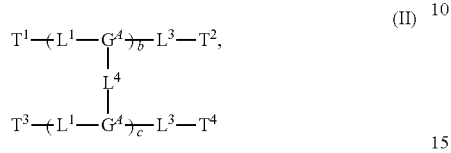

or a salt thereof, wherein:

- $G^A$ is optionally substituted alkylene, optionally substituted heteroalkylene, optionally substituted carbocyclylene, optionally substituted heterocyclylene, optionally substituted arylene, optionally substituted heteroarylene, or a combination thereof;
- each of $L^1$, $L^3$, and $L^4$, is independently a linker selected from the group consisting of a bond, optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, and combinations thereof;
- each of $T^1$, $T^2$, $T^3$, and $T^4$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, optionally substituted thiol, a structure of Formula (I), and a structure of Formula (II); and
- b and c are independently an integer between 1 and 10000, inclusive.

13. The ROMP-out BASP of claim 11, wherein the backbone polymeric arms are of Formula (I-a):

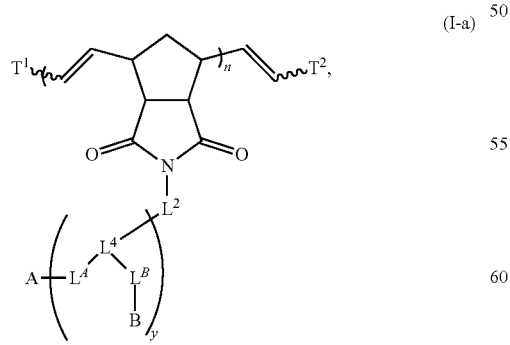

or a salt thereof.

14. The ROMP-out BASP of claim 11, wherein the backbone polymeric arms are of formula:

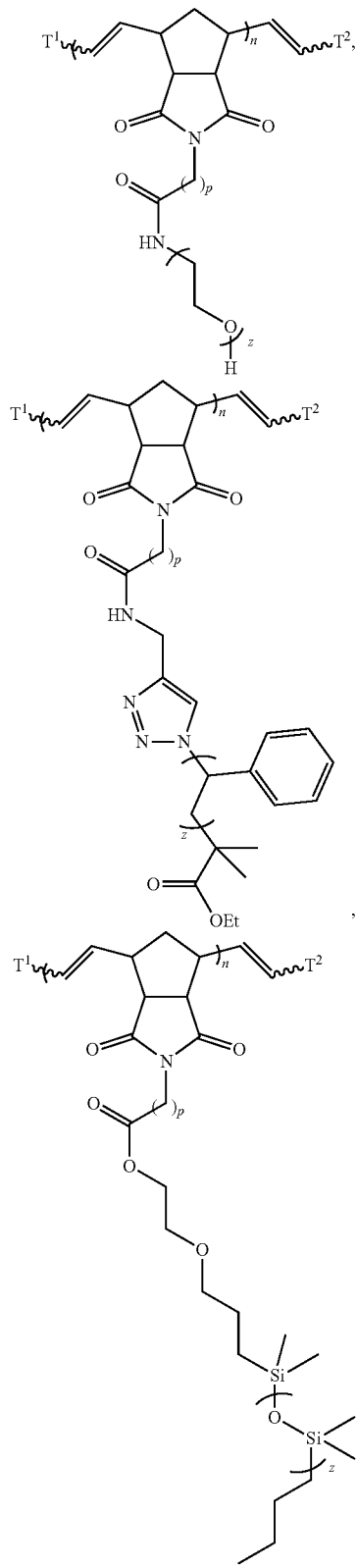

wherein:
p is an integer between 1 and 10, inclusive;
n is an integer between 5 and 10000, inclusive; and
z is an integer between 1 and 100, inclusive.

15. The ROMP-out BASP of claim 12, wherein the polymeric core of Formula (II) is of formula:

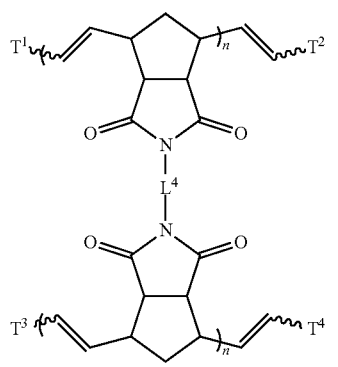

16. The ROMP-out BASP of claim 13, wherein B is a therapeutic agent or diagnostic agent.

17. The ROMP-out BASP of claim 13, wherein $L^2$ is optionally substituted alkylene or optionally substituted heteroalkylene.

18. The ROMP-out BASP of claim 13, wherein $L^4$ is of formula:

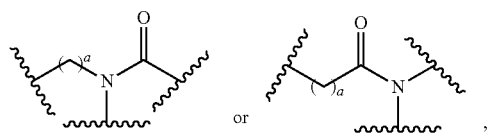

wherein a is an integer between 1 and 100, inclusive.

19. The ROMP-out BASP of claim 13, wherein $L^A$ is optionally substituted alkylene or optionally substituted heteroalkylene.

20. The ROMP-out BASP of claim 13, wherein $L^B$ is optionally substituted alkylene, optionally substituted heteroalkylene, optionally substituted arylene, or optionally substituted heteroarylene, or a combination thereof.

21. The ROMP-out BASP of claim 13, wherein A is a polydimethylsiloxane, polystyrene, polyethylene glycol, polyester, polyacrylamide, polycarbonate, polyfluorocarbon, or polysulfone.

22. The ROMP-out BASP of claim 15, wherein $L^4$ is optionally substituted heteroalkylene or optionally substituted arylene, or a combination thereof.

23. A method of preparing a ring-opening metathesis polymerization-out brush-arm star polymer (ROMP-out BASP), the method comprising the steps of:
(a) providing a first macromonomer comprising one or more polymeric sidechains and one or more olefin moieties;
(b) providing a metal complex;
(c) reacting the first macromonomer and the metal complex under conditions suitable to effect ring-opening metathesis polymerization (ROMP) to yield a polymer;
(d) providing a crosslinker, wherein the crosslinker comprises more than one olefin moiety;
(e) reacting the polymer and the crosslinker under conditions suitable to effect ROMP to yield a ring-opening-metathesis-polymerization-in brush-arm star polymer (ROMP-in BASP);
(f) providing a second macromonomer comprising one or more polymeric sidechains and one or more olefin moieties; and
(g) reacting the ROMP-in BASP and the second macromonomer under conditions suitable to effect ROMP to yield a ROMP-out BASP.

24. A method of preparing a brush-arm star polymer gel (BASP gel), the method comprising the steps of:
(a) providing a first macromonomer comprising one or more polymeric sidechains and one or more olefin moieties;
(b) providing a metal complex;
(c) reacting the first macromonomer and the metal complex under conditions suitable to effect ring-opening metathesis polymerization (ROMP) to yield a polymer;
(d) providing a first crosslinker, wherein the first crosslinker comprises more than one olefin moiety;
(e) reacting the polymer and the first crosslinker under conditions suitable to effect ROMP to yield a ring-opening-metathesis-polymerization-in brush-arm star polymer (ROMP-in BASP);
(f) providing a second macromonomer comprising one or more polymeric sidechains and one or more olefin moieties;
(g) reacting the ROMP-in BASP and the second macromonomer under conditions suitable to effect ROMP to yield a ROMP-out BASP;
(h) providing a second crosslinker, wherein the second crosslinker comprises more than one olefin moiety; and
(i) reacting the ROMP-out BASP and the second crosslinker under conditions suitable to effect ROMP to yield a BASP gel.

25. A pharmaceutical composition comprising:
a brush-arm star polymer gel, wherein the brush-arm star polymer gel is prepared by a method of claim 24; and
a pharmaceutically acceptable excipient.

26. The pharmaceutical composition of claim 25, wherein the brush-arm star polymer gel comprises one or more therapeutic agents.

27. A method of preparing a surface-functionalized ring-opening metathesis polymerization-out brush-arm star polymer (ROMP-out BASP), the method comprising the steps of:
(a) providing a first macromonomer comprising one or more polymeric sidechains and one or more olefin moieties;
(b) providing a metal complex;
(c) reacting the first macromonomer and the metal complex under conditions suitable to effect ring-opening metathesis polymerization (ROMP) to yield a polymer;
(d) providing a crosslinker, wherein the crosslinker comprises more than one olefin moiety;
(e) reacting the polymer and the crosslinker under conditions suitable to effect ROMP to yield a ring-opening-metathesis-polymerization-in brush-arm star polymer (ROMP-in BASP);
(f) providing a second macromonomer comprising one or more polymeric sidechains and one or more olefin moieties;
(g) reacting the ROMP-in BASP and the second macromonomer under conditions suitable to effect ROMP to yield a ROMP-out BASP;
(h) providing a surface capping reagent comprising one or more olefin moieties; and (i) reacting the ROMP-out BASP with the surface capping reagent under conditions suitable to effect ROMP to yield a surface-functionalized ROMP-out BASP.

\* \* \* \* \*